(12) United States Patent
van den Boom et al.

(10) Patent No.: US 7,608,394 B2
(45) Date of Patent: Oct. 27, 2009

(54) METHODS AND COMPOSITIONS FOR PHENOTYPE IDENTIFICATION BASED ON NUCLEIC ACID METHYLATION

(75) Inventors: Dirk Johannes van den Boom, La Jolla, CA (US); Mathias Ehrich, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 10/888,359

(22) Filed: Jul. 9, 2004

(65) Prior Publication Data

US 2006/0210992 A1     Sep. 21, 2006

Related U.S. Application Data

(60) Provisional application No. 60/556,632, filed on Mar. 26, 2004.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,826,360 A | 5/1989 | Iwasawa et al. |
| 4,851,018 A | 7/1989 | Lazzari et al. |
| 5,003,059 A | 3/1991 | Brennan |
| 5,079,342 A | 1/1992 | Alizon et al. |
| 5,118,937 A | 6/1992 | Hillenkamp et al. |
| 5,173,418 A | 12/1992 | Molin et al. |
| 5,252,478 A | 10/1993 | Margarit Y Ros et al. |
| 5,264,563 A | 11/1993 | Huse |
| 5,387,518 A | 2/1995 | Sawayanagi et al. |
| 5,391,490 A | 2/1995 | Varshavsky et al. |
| 5,427,927 A | 6/1995 | Meyer et al. |
| 5,436,150 A | 7/1995 | Chandrasegaran |
| 5,440,119 A | 8/1995 | Labowsky |
| 5,453,247 A | 9/1995 | Beavis et al. |
| 5,453,613 A | 9/1995 | Gray et al. |
| 5,498,545 A | 3/1996 | Vestal |
| 5,503,980 A | 4/1996 | Cantor |
| 5,506,137 A | 4/1996 | Mathur et al. |
| 5,536,649 A | 7/1996 | Fraiser et al. |
| 5,547,835 A | 8/1996 | Köster |
| 5,578,443 A | 11/1996 | Santamaria et al. |
| 5,604,098 A | 2/1997 | Mead et al. |
| 5,605,798 A | 2/1997 | Köster |
| 5,622,824 A | 4/1997 | Köster |
| 5,631,134 A | 5/1997 | Cantor |
| 5,635,713 A | 6/1997 | Labowsky |
| 5,646,020 A | 7/1997 | Swiggen et al. |
| 5,686,656 A | 11/1997 | Amirav et al. |
| 5,691,141 A | 11/1997 | Köster |
| 5,700,672 A | 12/1997 | Mathur et al. |
| 5,714,330 A | 2/1998 | Brenner et al. |
| 5,777,324 A | 7/1998 | Hillenkamp |
| 5,786,146 A | 7/1998 | Herman et al. |
| 5,792,664 A | 8/1998 | Chait et al. |
| 5,795,714 A | 8/1998 | Cantor et al. |
| 5,807,522 A | 9/1998 | Brown et al. |
| 5,830,712 A | 11/1998 | Rampersad et al. |
| 5,837,832 A | 11/1998 | Chee et al. |
| 5,843,669 A | 12/1998 | Kaiser et al. |
| 5,851,765 A | 12/1998 | Köster |
| 5,853,979 A | 12/1998 | Green et al. |
| 5,858,705 A | 1/1999 | Wei et al. |
| 5,864,137 A | 1/1999 | Becker et al. |
| 5,869,242 A | 2/1999 | Kamb |
| 5,871,911 A | 2/1999 | Dahlberg et al. |

(Continued)

FOREIGN PATENT DOCUMENTS

EP          0269520          1/1988

(Continued)

OTHER PUBLICATIONS

Xiong et al. ("Cobra: a sensitive and quantitative DNA methylation assay" Nucleic Acids Res. Jun. 15, 1997;25(12):2532-4).*

(Continued)

*Primary Examiner*—Kenneth R. Horlick
*Assistant Examiner*—Christopher M. Babic
(74) *Attorney, Agent, or Firm*—Grant Anderson LLP

(57) ABSTRACT

Methods and compositions for identifying an unknown phenotype of a tissue that correlates with changes in the methylation state of the tissue comprising, nucleic acid sample from the tissue with a reagent that modifies unmethylated cytosine to produce uracil, amplifying the nucleic acid target gene region using at least one primer that hybridizes to a strand of said nucleic acid target gene region to produce amplified nucleic acids, determining the characteristic methylation state of the nucleic acid target gene region by base specific cleavage and identification of methylation sites and comparing the ratio of methylated cytosine to unmethylated cytosine for each methylation site of the nucleic acid target gene region to the ratio of methylated cytosine to unmethylated cytosine for each methylation site of a tissue nucleic acid sample of the same type having a known phenotype thereby identifying the unknown phenotype.

12 Claims, 10 Drawing Sheets

U.S. PATENT DOCUMENTS

Figure 1A:
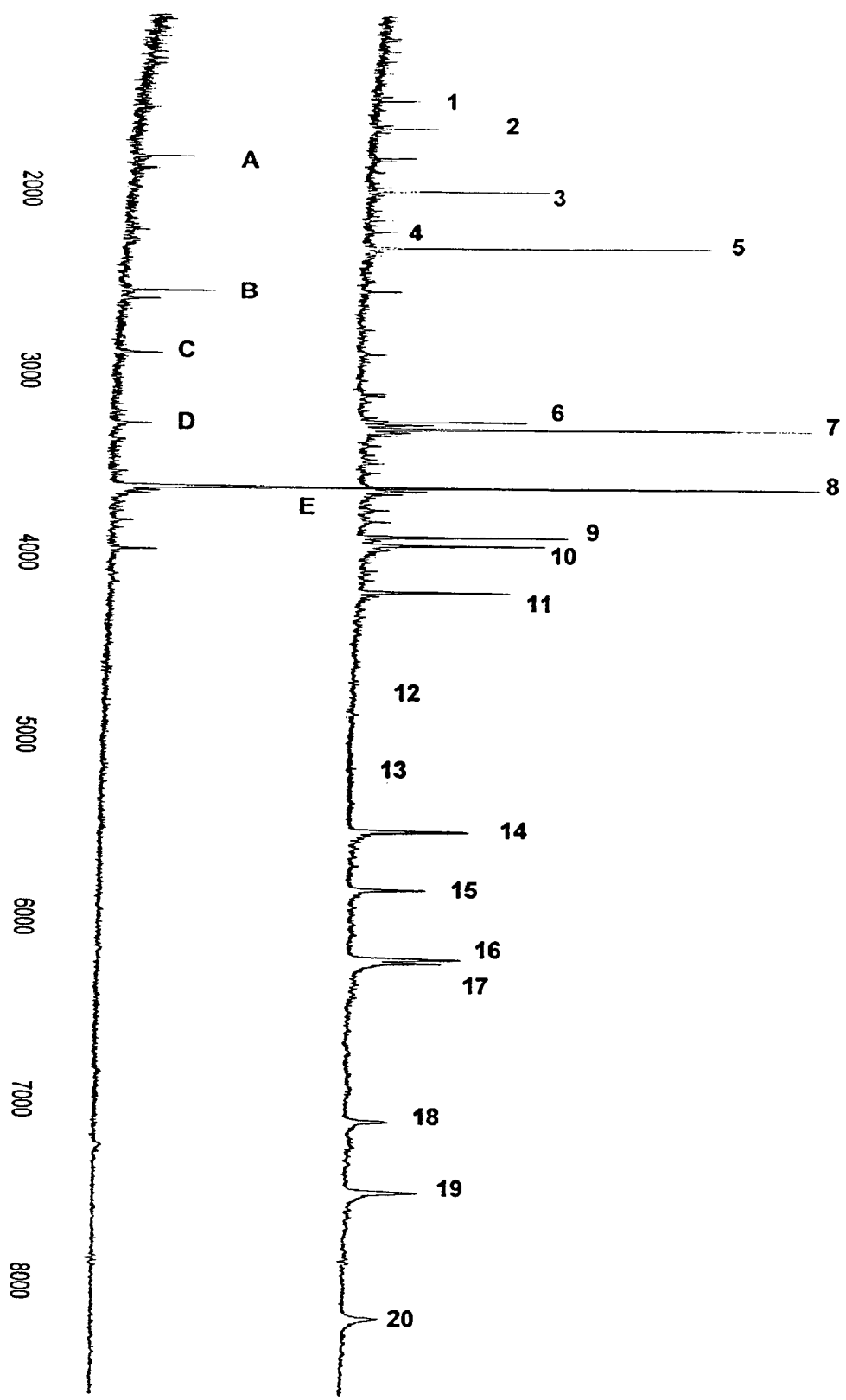

| | | | |
|---|---|---|---|
| 5,872,003 A | 2/1999 | Köster | |
| 5,874,283 A | 2/1999 | Harrington et al. | |
| 5,885,841 A | 3/1999 | Higgs, Jr. et al. | |
| 5,888,795 A | 3/1999 | Hamilton | |
| 5,900,481 A | 5/1999 | Lough et al. | |
| 5,928,870 A | 7/1999 | Lapid et al. | |
| 5,928,906 A | 7/1999 | Köster et al. | |
| 5,932,451 A * | 8/1999 | Wang et al. | 435/91.21 |
| 5,948,902 A | 9/1999 | Schembri et al. | |
| 5,952,176 A | 9/1999 | McCarthy et al. | |
| 5,965,363 A | 10/1999 | Monforte et al. | |
| 5,975,492 A | 11/1999 | Brenes | |
| 5,976,806 A | 11/1999 | Mahajan et al. | |
| 6,017,704 A | 1/2000 | Herman et al. | |
| 6,022,688 A | 2/2000 | Jurinke et al. | |
| 6,024,925 A | 2/2000 | Little et al. | |
| 6,043,031 A | 3/2000 | Koster et al. | |
| 6,051,378 A | 4/2000 | Monforte et al. | |
| 6,054,276 A | 4/2000 | Macevicz | |
| 6,059,724 A | 5/2000 | Campell et al. | |
| 6,074,823 A | 6/2000 | Köster | |
| 6,090,549 A | 7/2000 | Honkanen et al. | |
| 6,090,558 A | 7/2000 | Butler et al. | |
| 6,090,606 A | 7/2000 | Köster et al. | |
| 6,099,553 A | 8/2000 | Hart et al. | |
| 6,104,028 A | 8/2000 | Hunter et al. | |
| 6,110,426 A | 8/2000 | Shalon et al. | |
| 6,111,251 A | 8/2000 | Hillenkamp | |
| 6,112,161 A | 8/2000 | Dryden et al. | |
| 6,113,436 A | 9/2000 | Kuwahara et al. | |
| 6,133,436 A | 10/2000 | Köster et al. | |
| 6,140,053 A | 10/2000 | Köster | |
| 6,146,854 A | 11/2000 | Köster et al. | |
| 6,188,064 B1 | 2/2001 | Koster | |
| 6,190,865 B1 | 2/2001 | Jendrisak et al. | |
| 6,194,144 B1 | 2/2001 | Koster | |
| 6,194,180 B1 | 2/2001 | Joyce | |
| 6,197,498 B1 | 3/2001 | Koster | |
| 6,200,756 B1 | 3/2001 | Herman et al. | |
| 6,207,370 B1 | 3/2001 | Little et al. | |
| 6,214,556 B1 | 4/2001 | Olek et al. | |
| 6,221,605 B1 | 4/2001 | Koster | |
| 6,235,478 B1 | 5/2001 | Koster | |
| 6,238,871 B1 | 5/2001 | Koster | |
| 6,258,538 B1 | 7/2001 | Koster et al. | |
| 6,265,167 B1 | 7/2001 | Carmichael et al. | |
| 6,265,171 B1 | 7/2001 | Herman et al. | |
| 6,265,716 B1 | 7/2001 | Hunter et al. | |
| 6,268,131 B1 | 7/2001 | Kang et al. | |
| 6,270,835 B1 | 8/2001 | Hunt et al. | |
| 6,271,037 B1 | 8/2001 | Chait et al. | |
| 6,277,573 B1 | 8/2001 | Koster et al. | |
| 6,297,006 B1 | 10/2001 | Drmanac et al. | |
| 6,300,076 B1 | 10/2001 | Koster | |
| 6,309,833 B1 | 10/2001 | Edman et al. | |
| 6,322,970 B1 | 11/2001 | Little et al. | |
| 6,326,174 B1 | 12/2001 | Joyce et al. | |
| 6,331,427 B1 | 12/2001 | Robison | |
| 6,383,775 B1 | 5/2002 | Duff et al. | |
| 6,423,966 B2 | 7/2002 | Hillenkamp et al. | |
| 6,428,955 B1 | 8/2002 | Koster et al. | |
| 6,436,635 B1 | 8/2002 | Fu et al. | |
| 6,440,705 B1 | 8/2002 | Stanton, Jr. et al. | |
| 6,475,736 B1 | 11/2002 | Stanton, Jr. | |
| 6,500,621 B2 | 12/2002 | Koster | |
| 6,522,477 B2 | 2/2003 | Anhalt | |
| 6,537,746 B2 | 3/2003 | Arnold et al. | |
| 6,558,902 B1 | 5/2003 | Hillenkemp | |
| 6,566,055 B1 | 5/2003 | Monforte et al. | |
| 6,569,385 B1 | 5/2003 | Little et al. | |
| 6,589,485 B2 | 7/2003 | Koster | |
| 6,602,662 B1 | 8/2003 | Koster et al. | |
| 6,884,586 B2 | 4/2005 | Van Ness | |
| 6,994,960 B1 | 2/2006 | Foote et al. | |
| 6,994,969 B1 | 2/2006 | Zabeau et al. | |
| 2001/0008615 A1 | 7/2001 | Little et al. | |
| 2002/0009394 A1 | 1/2002 | Koster et al. | |
| 2002/0042112 A1 | 4/2002 | Koster et al. | |
| 2002/0120127 A1 | 8/2002 | Church et al. | |
| 2002/0155587 A1 | 10/2002 | Opalsky et al. | |
| 2003/0013099 A1 | 1/2003 | Lasek et al. | |
| 2003/0027169 A1 | 2/2003 | Zhang et al. | |
| 2003/0082600 A1 | 5/2003 | Olek et al. | |
| 2003/0087235 A1 * | 5/2003 | Dairkee et al. | 435/6 |
| 2003/0129589 A1 | 7/2003 | Koster et al. | |
| 2003/0180748 A1 | 9/2003 | Braun et al. | |
| 2003/0180749 A1 | 9/2003 | Braun et al. | |
| 2003/0180779 A1 | 9/2003 | Lofton-Day et al. | |
| 2003/0190644 A1 | 10/2003 | Braun et al. | |
| 2004/0014101 A1 | 1/2004 | Liu et al. | |
| 2004/0029258 A1 | 2/2004 | Heaney et al. | |
| 2004/0253141 A1 | 12/2004 | Schembri et al. | |
| 2005/0009053 A1 | 1/2005 | Boecker et al. | |
| 2005/0009059 A1 | 1/2005 | Shapero | |
| 2005/0019762 A1 | 1/2005 | Olek | |
| 2005/0026183 A1 * | 2/2005 | Fan et al. | 435/6 |
| 2005/0064406 A1 | 3/2005 | Zabarovsky | |
| 2005/0064428 A1 | 3/2005 | Berlin | |
| 2005/0069879 A1 | 3/2005 | Berlin | |
| 2005/0089904 A1 | 4/2005 | Beaulieu et al. | |
| 2005/0112590 A1 | 5/2005 | van den Boom et al. | |
| 2005/0153316 A1 | 7/2005 | Jeddeloh | |
| 2005/0153347 A1 | 7/2005 | Shapero | |
| 2005/0164246 A1 * | 7/2005 | Fan et al. | 435/6 |
| 2005/0272070 A1 | 12/2005 | Ehrich et al. | |
| 2006/0073501 A1 | 4/2006 | van den Boom et al. | |

FOREIGN PATENT DOCUMENTS

| | | |
|---|---|---|
| EP | 0296781 | 6/1988 |
| EP | 0299652 | 7/1988 |
| EP | 0332435 | 9/1989 |
| EP | 0395481 | 4/1990 |
| EP | 0596205 | 5/1994 |
| EP | 0655501 | 5/1995 |
| EP | 1 179 589 A1 | 2/2002 |
| EP | 1197567 A2 * | 4/2002 |
| FR | 2749662 | 6/1996 |
| GB | 2329475 | 8/1998 |
| JP | 2003-245087 | 9/2003 |
| WO | WO 92/13969 | 8/1992 |
| WO | WO 93/15407 | 8/1993 |
| WO | WO 93/21592 | 10/1993 |
| WO | WO 94/00562 | 1/1994 |
| WO | WO 94/15219 | 7/1994 |
| WO | WO 94/16101 | 7/1994 |
| WO | WO 94/21663 | 9/1994 |
| WO | WO 94/21822 | 9/1994 |
| WO | WO 95/25281 | 9/1995 |
| WO | WO 96/29431 | 9/1996 |
| WO | WO 96/32504 | 10/1996 |
| WO | WO 96/36732 | 11/1996 |
| WO | WO 96/36986 | 11/1996 |
| WO | WO 97/03210 | 1/1997 |
| WO | WO 97/08306 | 3/1997 |
| WO | WO 97/08308 | 3/1997 |
| WO | WO 97/33000 | 9/1997 |
| WO | WO 97/37041 | 10/1997 |
| WO | WO 97/40462 | 10/1997 |
| WO | WO 97/42348 | 11/1997 |
| WO | WO 97/43617 | 11/1997 |
| WO | WO 98/12355 | 3/1998 |
| WO | WO 98/12734 | 3/1998 |
| WO | WO 98/20019 | 5/1998 |

| | | |
|---|---|---|
| WO | WO 98/20020 | 5/1998 |
| WO | WO 98/20166 | 5/1998 |
| WO | WO 98/24935 | 6/1998 |
| WO | WO 98/33808 | 8/1998 |
| WO | WO 98/35609 | 8/1998 |
| WO | WO 98/54571 | 12/1998 |
| WO | WO 99/05323 | 2/1999 |
| WO | WO 99/12040 | 3/1999 |
| WO | WO 99/31278 | 6/1999 |
| WO | WO 99/50447 | 10/1999 |
| WO | WO 99/54501 | 10/1999 |
| WO | WO 99/57318 | 11/1999 |
| WO | WO 00/18967 | 4/2000 |
| WO | WO 00/22130 | 4/2000 |
| WO | WO 00/31300 | 6/2000 |
| WO | WO 00/51053 | 8/2000 |
| WO | WO 00/56446 | 9/2000 |
| WO | WO 00/60361 | 10/2000 |
| WO | WO 00/66771 | 11/2000 |
| WO | WO 01/27857 | 4/2001 |
| WO | WO 01/55455 A2 | 8/2001 |
| WO | WO 02/13122 | 2/2002 |
| WO | WO 02/25567 | 3/2002 |
| WO | WO 02/086163 | 10/2002 |
| WO | WO 02/086794 | 10/2002 |
| WO | WO 02/101353 | 12/2002 |
| WO | WO 03/000926 | 1/2003 |
| WO | WO 03/002760 | 1/2003 |
| WO | WO 03/031649 | 4/2003 |
| WO | WO 03/038121 | 5/2003 |
| WO | WO 03/080863 | 10/2003 |
| WO | WO 2004/013284 | 2/2004 |
| WO | WO 2004/050839 | 6/2004 |
| WO | WO 2004/097369 | 11/2004 |
| WO | WO 2005/040399 | 5/2005 |

OTHER PUBLICATIONS

Baylin and Bestor ("Altered methylation patterns in cancer cell genomes: cause or consequence?" Cancer Cell. May 2000;1(4):299-305).*

Chen et al. ("Detection in fecal DNA of colon cancer-specific methylation of the nonexpressed vimentin gene" J Natl Cancer Inst. Aug. 3, 2005;97(15):1124-32).*

Zhu et al. ("Use of DNA methylation for cancer detection and molecular classification" J Biochem Mol Biol. Mar. 31, 2007;40(2):135-41).*

Futscher et al. ("Role for DNA methylation in the control of cell type specific maspin expression" Nat Genet. Jun. 2002;31(2):175-9. Epub May 20, 2002). Futscher examines the methylation status of the SerpinB5 promoter region.*

Zou et al. ("Maspin, a serpin with tumor-suppressing activity in human mammary epithelial cells" Science. Jan. 28, 1994;263(5146):526-9).*

NCBI (GenBank Accession No. NM_002639).*

Buck et al. ("Design Strategies and Performance of Custom DNA Sequencing Primers") BioTechniques. Sep. 1999. 27: pp. 528-536).*

Futscher et al. ("Role for DNA methylation in the control of cell type specific maspin expression" Nat Genet. Jun. 2002;31(2):175-9. Epub May 20, 2002).*

Moon, C. et al. "Aquaporin Expression in Human Lymphocytes and Dentritic Cells" American Journal of Hematology, 2004, 128-133, 75, USA.

Sato, N. et al. "Identification of maspin and S100P as novel hypomethylation targets in pancreatic cancer using global gene expression profiling", 2004, 1531-1538, 23, USA.

Ogasawara, S. et al., "Disruption of cell-type-specific methylation at the Maspin gene promoter is frequently involved in . . ." Oncogene, 2004, 1117-1124, 23, Japan.

Murakami, J. et al., "Effects of demethylating agent 5-aza-2'-deoxycytidine and histone deacetylase inhibitor FR901228 on maspin . . ." Oral Oncology 2004, 597-603, 40, Japan.

Hurtubise, A. et al., "Evaluation of antineoplastic action of 5-aza-2'-deoxycytidine (Dacogen) and docetaxel (Taxotere) on . . . " Anti-Cancer Drugs, 2004, 161-167,15, Canada.

Wada, K. et al., "Aberrant Expression of the Maspin Gene Associated with Epigenetic Modification . . ." J Invest Dermatol, 2004, 805-811, 122, Japan.

Futscher, B. et al., "Aberrant Methylation of the Maspin Promoter is an Early Event in Human Breast Cancer" Neoplasia, 2004, 380-389, 6, USA.

Kim, S. et al., "Maspin Expression Is Transactivated by P63 and Is Critical for the Modulation of Lung Cancer Progression" Cancer Research, 2004, 6900-6905, 64, Korea.

Yatabe, Y. et al., "Maspin expression in normal lung and non-small-cell lung cancers: cellular property . . ." Oncogene, 2004, 4041-4049, 23, Japan.

Moon, C. et al., "Involvement of aquaporins in colorectal carcinogenesis" Oncogene, 2003, 6699-6703, 22, USA.

Oshio, K. et al., "Aquaporin-1 expression in human glial tumors suggests a potential novel therapeutic target for tumor-associated . . . " Acta Neurochir, 2003, 499-502, 86, USA.

Akiyama, Y. et al., "Cell-Type-Specific Repression of the Maspin Gene Is Disrupted Frequently by Demethylation at the . . . " Amer. J. Of Pathology, 2003, 1911-1919,163, Japan.

Smith, S. et al., "Maspin—the most commonly-expresssed gene of the 18q21.3 serpin cluster in lung cancer . . . " Oncogene, 2003, 8677-8687, 22, UK.

Ling, X. et al., "Proteomics-Based Identification of Maspin Differential Expression in Bronchial Epithelia Immortalized . . ." Chinese J. of Cancer, 2003, 463-466, 22, China.

Sigalotti, L. et al., "Cancer testis antigens expression in mesothelioma:role of DNA methylation . . . " British J. of Cancer, 2002, 979-982, 86, UK.

Egland, K. et al., "Characterization of Overlapping XAGE-1 Transcripts Encoding a Cancer Testis Antigen Expressed in . . . " Molecular Cancer Therapeutics, 2002, 441-450, USA.

Zendman, A. et al., "The XAGE Family of Cancer/Testis-Associated Genes: Alignment and Expression Profile in Normal Tissues . . . " Int. J. Cancer, 2002, 361-369, 99 Netherlands.

Saadoun, S. et al., "Increased aquaporin I water channel expression in human brain tumours", British J. of Cancer, 2002, 621-623, 87, UK.

Maass, N., et al., "Hyipermethylation and histone deacetylation lead to silencing of the maspin gene in human breast cancer . . . " BBRC, 2002, 125-128, 297, USA.

Futscher, B., et al., "Role for DNA methylation in the control of cell type-specific maspin expression", Nature Genetics, 2002, 175-179, 31, USA.

Costello, J. et al., "Methylation matters: a new spin on maspin" Nature Genetics, 2002, 123-124, 31 USA.

Heighway, J. et al., "Expression profiling of primary non-small cell lung cancer for target identification", Oncogene, 2002, 7749-7763, 21, UK.

Vacca, A. et al., "Microvessel overexprssion of aquaporin 1 parallels bone marrow angiogenesis in patients with active . . . " British J. of Haematology, 2001, 415-421,113, Italy.

Maass, N. et al., "Decline in the expression of the serine proteinase inhibitor maspin is associated with tumour progression . . . " J. of Pathology, 2001, 321-326,195, Germany.

Liu, X. et al., "XAGE-1, A New Gene That Is Frequently Expressed in Ewing's Sarcoma" Cancer Research, 2000, 4752-4755, 60, USA.

Takenawa, J. et al., "Transccript Levels of Aquaporin 1 and Carbonic Anhydrase IV as Predictive Indicators for Prognosis of Renel Cell . . . " Int. J. Cancer, 1998, 1-7, 79, Japan.

Aebersold and Mann, Nature, 422:198-207 (2003).

Amir et al., Nature Genet. 23:1d85-188 (1999).

Anderson, S., Nucleic Acids Res., 9(13): 3015-3027 (1981).

Anker, R. et al., Hum. Mol. Genet., 1(2): 137 (1992).

Arnheim et al., Proc. Natl. Acad. Sci. USA, 82:6970-6974 (1985).

Arrand et al., "Different Substrate Specificities of the Two DNA Ligases of Mammalian Cells", J. Biol. Chem., 261(20):9079-9082, (1986).

Bader and Hogue, BMC Bioinformatics. Jan 13, 2003;4:2, Epub Jan 13, 2003, http://biomedcentral.com/1471-2105/4/2.

Badger et al., "New features and enhancements in the X-PLOR computer program", Proteins: Structure, Function, and Genetics, 35(1):25-33, (1999).
Bains and Smith, J. Theoret. Biol., 135:303-307 (1988).
Banerjee, A. et al., Science, 263(5144): 227-230 (1994).
Barlow, D.P. and H. Leach, Trends Genet., 3: 167-171(1987).
Beaulieu et al., Am. J. Hum. Genet., 73(5):441- (2003).
Beck et al., "Chemiluminescent detection of DNA: application for DNA sequencing and hybridization", Nucl. Acids Res., 17(13):5115-5123, (1989).
Beckmann, J.S. and J.L. Weber, 12: 627-631 (1992).
Berkenkamp, S. et al., Proc. Natl.Acad. Sci. U.S.A., 93(14): 7003-7007 (1996).
Bertina et al., "Mutation in blood coagulation factor V associated with resistance to activated protein C", Nature, 369:64-67, (1994).
Bessho et al., "Nucleotide excision repair 3' endonuclease XPG stimulates the activity of base excision repair enzyme thymine glycol Dna glycosylase", Nucl. Acids Res., 27(4):79-83, (1999).
Biemann, K., Methods in Enzymol., 193: 455-479(1990).
Bird, A., Genes and Development, 16(1): 6-21 (2002).
Blazewicz et al., "On some properties on DNA graphics," Discrete Applied Mathematics, vol. 98, 1999, pp. 1-19.
Blazewicz et al., "On the recognition of de Bruijn graphs and their induced subgraphs," Discrete Applied Mathematics, vol. 245, 81-92 Feb. 28, 2002.
Bleczinski, C. and Richert, C., "Monitoring the Hybridization of the Components of Oligonucleotide Mixtures to Immobilized DNA via Matrix-assisted Laser Desorption/Ionization Time-of-flight Mass Spectrometry", Rapid Communications in Mass Spectrometry, 12:1737-1743, (1998).
Bocker, S., Bioinformatics 19(Suppl. 1):i44-i53 (2003).
Bocker, Lect. Notes Comp. Sci. 2818:476-487 (2003) (http://gi.cebitec.uni-bielefeld.de/people/boecker/download/Preprint_2003-04_Sequencing_SBoecker.pdf).
Bocker, Technical Report(http://gi.cebitec.uni-bielefeld.de/people/boecker/download/Preprint_2003-07_WeightedSC_SBoecker.pdf).
Boguski, M.S. et al., J. Biol. Chem., 255(5): 2160-2163 (1980).
Braun et al., "Detecting CFTR gene mutations by using primer oligo base extension and mass spectrometry", Clin. Chem., 43(7):1151-1158, (1997).
Braun et al., "Improved Analysis of Microsatellites Using Mass Spectrometry", Genomics, 46:18-23, (1997).
Breen, G., et al., Determining SNP Allele Frequencies in DNA Pools, Biotechniques, (2000). 464-470, 28(3).
Bregman et al., "Molecular Characterization of Bovine Brain P75, a High Affinity Binding Protein for the Regulatory Subunit of cAMP-dependent", J. Biol. Chem., 266(11):7207-7213 (1991).
Browne, K. A., J.Am. Chem. Soc., 124(27): 7950-7962 (2002).
Buetow et al., "High-throughput development and characterization of a genomewide collection of gene-based single nucleotide polymorphism markers by chip-based matrix-assisted laser desorption/ionization time-of-flight mass spectrometry", Proc. Natl. Acad. Sci. USA, 98(2):581-584, (2001).
Burton et al., "Type II regulatory subunits are not required for the anchoring-dependent modulation of Ca2+ channel activity by cAMP-dependent protein kinase", Proc. Natl. Acad. Sci. USA 94:11067-11072 (1997).
Cai et al., "Different Discrete Wavelet Transforms Applied to Denoising Analytical Data," J. Chem. Inf. Comput. Sci. 38: 1161-1170 (1998).
Caldwell and Joyce, PCR Methods and Applications 2:28-33 (1992).
Cannistraro, V.J. And D. Kennell, Eur. J. Biochem., 181(2): 363-370 (1989 ).
Carr et al., "Interaction of the Regulatory Subunit (RII) of cAMP-dependent Protein Kinase with RII-anchoring Proteins occurs through an Amphipathic Helix Binding Motif", J. Biol. Chem., 266(22): 14188-14192 (1991).
Carr et al., "Association of the Type II cAMP-dependent Protein Kinase with a Human Thyroid RII-anchoring protein", J. Biol Chem., 267(19):13376-13382 (1992).
Caskey, C. T. et al., Science 256(5058): 784-789 (1992).

Cavalli-Sforza, L.I., "The DNA revolution in population genetics," Trends in Genetics 14(2): 60-65 (1998).
Chait, B.T. and S.B.H. Kent, Science, 257(5078): 1885-1894(1992).
Chakrabarti, L. et al., Nature, 328(6130): 543-547 (1987).
Chechetkin et al., Biomol. Struct. Dyn., 18(1):83-101 (2000).
Chiu et al., "Mass Spectrometry of Nucleic Acids", Clin. Chem., 45:1578, (1999).
Chiu et al., "Mass Spectrometry of single-stranded restriction fragments captured by an undigested complementary sequence", Nucl. Acids. Res., 28(8):e31(i-iv), (2000).
Chung, M.H. et al., Mutat. Res., 254(1): 1-12, (1991).
Clausen et al., J. Clinical Investigation, 98(5):1195-1209 (1996).
Clegg et al., "Genetic characterization of a brain-specific form of the type I regulatory subunit of cAMP-dependent protein kinase", Proc. Natl. Acad. Sci USA, 85:3703-3707 (1988).
Cleveland, D.W. et al., J. Biol. Chem., 252(3): 1102-1106 (1977).
Coghlan et at., "Association of Protein Kinase A and Protein Phosphatase 2B with a Common Anchoring Protein", Science, 267: 108-111 (1995).
Cohen et al., "Emerging Technologies for Sequencing Antisense Oligonucleotides: Capillary Electrophoresis and Mass Spectrometry," Advanced Chromatography, 36:127-162, (1996).
Colledge, M. and Scott, J.D., "AKAPs: from structure to function", Trends in Cell Biology, 9:216-221, (1999).
Collins et al., "A DNA Polymorphism Discovery Resource for Resource for Research on Human Genitic Variation", Genome Research, 8:1229-1231 (1998).
Corder et al., "Gene Dose of Apolipoprotein E Type 4 Allele and the Risk of Alzheimer's Disease in Late Onset Families", Science, 261:921-923, (1993).
Costello et al., Nature Genet., 24:132-138 (2000).
Dahl, et al., "DNA methylation analysis techniques," Biogerontology, 2003, vol., 4 pp. 233-250; especially pp. 242-245.
Database WPI, Derwent publication # 011635345 citing International Patent Application WO 9747974 of the parent French Patent Application FR 2,749,662.
Database WPI, Derwent publication #007515331 Jul. 11, 2006.
Dausset, J. et al., Genomics, 6(3): 575-577(1990).
De Noronha et al., (1992) PCR Methods and Applications, 2(2), p. 131-136.
Delagrave et al., Protein Engineering, 6:327-331 (1993).
Deng et al., Cancer Research, 1999, vol. 59, pp. 2029-2033.
Ding and Cantor, Proc. Natl. Acad. Sci. USA, 100(12):7449-7453 (2003).
Dittmar, M., "Review of studies of polymorphic blood systems in the Ayrnara indigenous population from Bolivia, Peru, and Chile," Anthropol. Anz. 53(4): 289-315 (1995).
Dodgson et al., "DNA Marker Technology: A Revolution in Animal Genetics," PoultryScience 76:1108-1114 (1997).
Donis-Keller, H. et al., Nucleic Acids Res., 4(8): 2527-2537 (1977).
Donis-Keller, H., Nucleic Acids Res., 8(14): 3133-3142 (1980).
Downes, Kate, et al., SNP allele frequency estimation in DNA pool and variance components analysis, BioTechniques, (2004), 840-846, 36(6), The Wellcome Trust Sanger Institute.
Dunham, I. et al., Nature 402(6761): 489-495 (1999).
Edwards, M.C. et al.Nucleic Acids Res., 19(17): 4791 (1991).
Eftedal et al., "Consensus sequences for good and poor removal or uracil from double stranded DNA by uracil-DNA glycosylase", Nucl. Acids Res., 21(9):2095-2101, (1993).
Eggertsen et al., Clinical Chemistry 30(10):2125-2129 (1993).
Ehrlich, S.D. et al., Biochemistry 10(11):2000-2009 (1971).
Eitan et al., Nucleic Acids Res. 30(12):E62.1-E62.8 (2002).
Elso et al., Genome Res. 12(9):1428-1433 (2002).
Faux, M.C. and Scott, J.D., "More on target with protein phosphorylation: conferring specificity by location", Trends Biochem., 21:312-315, (1996).
Fei and Smith., Rapid Commun. Mass. Spectrom., 14(11):950-959 (2000).
Fischer, "Red Tape: It's in You to Give: Last year the Canadian Blood Services' security measures weeded out 200,000 would-be donors. Doug Fischer looks at the reasons behind the red tape." Ottawa Citizen Saturday Final Edition Oct. 5, 2002.

Foster et al., "Naming Names in Human Genetic Variation Research", Genome Research, 8:755-757 (1998).
Fu et al., "A DNA sequencing strategy that requires only five bases of known terminal sequence for priming", Proc. Natl. Acad. Sci. USA, 92:10162-10166, (1995).
Fu et al., "Efficient preparation of short DNA sequence ladders potentially suitable for MALDI-TOF DNA sequencing", Genetic Analysis: Biomolecular Engineering, 12:137-142, (1996).
Fu et al., "Sequencing double-stranded DNA by strand displacement", Nucl. Acids Res., 25(3):677-679, (1997).
Fu et al., "Sequencing Exons 5 to 8 of the p53 Gene by MALDI-TOF Mass Spectrometry", Nature Biotechnol., 16:381-384, (1998).
Gabbita et al., "Decrease in Peptide Methionine Sulfoxide Reductase in Alzheimer's Disease Brain", J. Neurochemistry, 73(4):1660-1666, (1999).
Gardiner-Gordon et al., J. Mol. Biol. 196:261-281 (1987).
Genbank Accession AC005730.
Genbank Accession AF021833.
Genbank Accession AF096289.
Genbank Accession AJ242973.
Genbank Accession AW195104.
Genbank Accession AW874187.
Genbank Accession NM007202.
Genbank Accession No. AF037439, Chatterjee et al. Dec. 1997.
Genbank Accession X86173.
German, J. and E. Passarge, Clin. Genet., 35: 57-69 (1989).
Germer, Saren, et al, High-throughput SNP Allele-Frequency Determination In Pooled DNA Samples by Kinetic PCR, Methods, Genome Research, (2000). 258-266, 10, Cold Spring Harbor Laboratory Press.
Germino, J. and D. Bastis, Proc. Natl. Acad. Sci. U.S.A., 81(15):4692-(1984).
Glantz et al., "Characterization of Distinct Tethering and Intracellular Targeting Domains in AKAP75, a Protein That Links cAMP-dependent Protein Kinase IIβ to the Cytoskeleton", J. Biol. Chem., 268(17):12796-12804, (1993).
Gogos, J.A. et al., Nucleic Acids Res., 18(23): 6807-6817 (1990).
Goldmacher et al., Photoactivation of toxin conjugates, Bioconj. Chem. 3:104-107 (1992).
Goldman and Youvan, Biotechnology 10:1557-1561 (1992).
Graber et al., Genetic Analysis: Biomolecular Engineering, 14:215-219 (1999).
Griffin et al., "Genetic analysis by peptide nucleic acid affinity MALDI-TOF mass spectrometry," Nature Biotechnology, 15:1368-1372, (1997).
Grunau et al., Nucl. Acid Res., 29:C65 (2001).
Guatelli et al., "Isothermal, in vitro amplification of nucleic acids by a muttienzyme reaction modeled after retroviral replication", Proc. Natl. Acad. Sci. USA, 87:1874-1878, (1990).
Gunderson et al., "Mutation detection by ligation to complete n-mer DNA Arrays," Genome Res. Nov. 1998;8(11):1142-1153.
Gupta, R.C. and K. Randerath, Nucleic Acids Res., 4(6)1957-1978 (1977).
Gust, I.D. et al., Intervirology, 20: 1-7 (1983).
Gut, I. G. and S. Beck, Nucleic Acids Res., 23(8): 1367-1373 (1995).
Guyader, M. et al., Nature, 326(6114): 662-669 (1987).
Haff and Smirnov, Genome Research, 7:378-388 (1997).
Haffey, M. L. et al., DNA,6(6): 565-571 (1987).
Hahner, S. et al., Nucleic Acids Res., 25(10): 1957-1964 (1997).
Hanish, J. and M. McClelland, Gene, Gene. Anal. Tech., 5: 105-107 (1988).
Harrington, J.J. and M.R. Lieber, Genes and Develop., 8(11): 1344-1355 (1994).
Hartmer et al., Nucleic Acids Res., 31(9):E47.1-E47.10 (2003).
Hausken et al., "Mutational Analysis of the A-Kinase Anchoring Protein (AKAP)-binding Site on RII", J. Biol. Chem., 271 (46):29016-29022 (1996).
Hazum et al., "A Photocleavable Protecting Group For The Thiol Function of Cysteine", Pept., Proc. Eur. Pept. Symp., 16th Brunfeldt, K. (Ed.), pp. 105-110, (1981).
Herman et al., "Methylation-specific PCR: A Novel PCR Assay for Methylation Status of CpG Islands," PNAS 93:9821-9826 (1996).

Hey, J., "Population genetics and human origins haplotypes are key," Trends in Genetics 14(8): 303-305 (1998) (with reply by L. Cavalli-Sforza).
Heym, B. et al., Lancet, 344(8918): 293-298 (1994).
Higgins et al., "Competitive Oligonucleotide Single-Base Extension Combined with Mass Spectrometric Detection for Mutation Screening", BioTechniques, 23(4):710-714, (1997).
Higgins et al., "DNA-Joining Enzymes: A Review", Methods in Enzymology, 68:50-71, (1979).
Higley, M. and Lloyd, R.S., "Processivity of uracil DNA glycosylase", Mutation Research, DNA Repair, 294:109-116, (1993).
Hillenkamp, F. and M. Karas, Anal. Chem., 63(24): 1193A-1202A (1991).
Hinton, Jr. et al., "The application of robotics to fluorometric and isotopic analyses of uranium", Laboratory Automation & Information Management., 21:223-227, (1993).
Hoogendoorn, Bastiaan, et al, Cheap, accurate and rapid allele frequency estimation of single nucleotide polymorphism by primer extension and DHPLC in DNA pools, Hum Genet (2000) 488-493,107, Pringer-Verlag.
Hsu, I-C. et al., Carcinogenesis, 15(8): 1657-1662 (1994).
Huang et al., "D-AKAP2, a novel protein kinase A anchoring protein with a putative RGS domain", Proc. Natl. Acad. Sci USA, 94:11184-11189 (1997).
Huang et al., "Identification of a Novel Protein Kinase A Anchoring Protein That Binds Both Type I and Type II Regulatory Subunits", J. Biol. Chem., 272:8057-8064 (1997).
Huang, Z.-H. et al., Anal. Biochem., 268(2):305-317 (1999).
Hubbard, M.J. and Cohen, P., "On target with a new mechanism for the regulation of protein phosphorylation", Trends Biochem, Sci., 18:172-177, (1993).
Ikemoto, S., "Searching for Genetic Markers In the Fields of Forensic Medicine and Human Genetics," N,bpon Hoigaku Zasshi 49(6): 41 9-431 (1 995).
Instrumentation; "Genesis 200/8" (200 cm with including an 8-tip arm) liquid handling systems; Tecan AG of Switzerland ("Tecan"), Tecan Products for Diagnostics and Life Science, located at http://www.tecan.ch/index.htm.
Instrumentation; "Model CRS A 255" robot"Digital Servo Gripper""Plate Cube" system."lid parking station""shaker"Robocon Labor-und Industrieroboter Ges.m.b.H of Austria ("Robocon").
Instrumentation; "Multimek 96" automated pipettor; Beckman Coulter, Inc. located at http://www.coulter.com, Sep. 8, 1999.
Instrumentation; "Nano-Plotter" from GeSiM, Germany, located at http:/www.gesim.de/np-intro.htm.
Instrumentation; Bar code systems, including one and two dimensional bar codes, readable and readable/writable codes and systems; Datalogic S.p.A. of Italy ("Datalogic") located at http://www.datalogic.com.
Instrumentation; Dynabeads, streptavidin-coated magnetic beads; from Dynal, Inc. Great Neck, NY and Oslo Norway.
Instrumentation;"MJ Microseal" plate sealer; Thermal Cycler Accessories: Sealing Options, Sealing Products, MJ Research, located at http://www.mjresearch.com/html/consumables/ealing/sealing_products.html.
International Search Report for International Application No. PCT/US00/08111, Date of Mailing Nov. 13, 2000.
International Search Report for International Application No. PCT/US005/32441 Oct. 2, 2006.
Jahnen et al., Biochem. Biophys. Res. Commun.,166(1): 139-145 (1990).
Jahnsen et al., "Molecular Cloning, CDNA Structure, and Regulation of the Regulatory Subunit of Type II CAMP-dependent Protein Kinase from Rat Ovarian Granulosa Cells", J. Biol. Chem., 261 (26):12352-12361 (1986).
Jeffreys et al., Nature, 314:67-73 (1985).
Jiang-Baucom et al., "DNA Typing of Human Leukocyte Antigen Sequence Polymorphisms Nucleic Acid Probes and MALDI-TOF Mass Spectrometry," Analytical Chemistry, 69:4894-4898, (1997).
Johnson, R. S. et al., Intl. J. Mass Spectrom. Ion Processes,86: 137-154 (1988).
Ju, L.-Y., et al., Electrophoresis 12(4):270-273 (1991).

Jurinke et al., "Analysis of Ligase Chain Reaction products via Matrix-Assisted Laser Desorption/Ionization Time-of-Flight-Mass Spectrometry", Anal. Biochem., 237:174-181, (1996).
Jurinke et al., "Application of nested PCR and mass spectrometry for DNA-based virus detection: HBV-DNA detected in the majority of isolated anti-HBc positive sera", Genetic Analysis: Biomolecular Engineering, 14:97-102, (1998).
Jurinke et al., "Detection of hepatitis B virus DNA in serum samples via nested PCR and MALDI-TOF mass spectrometry," Genetic Analysis: Biomolecular Engineering, 13:67-71, (1996).
Jurinke et al., "Detection of RET proto-oncogene codon 634 mutations using mass spectrometry", J. Mol. Med., 75:745-750, (1997).
Jurinke et al., "Recovery of Nucleic Acids from Immobilized Biotin-Streptavidin Complexes Using Ammonium Hydroxide and Applications in MALDI-TOF Mass Spectrometry", Anal. Chem., 69:904-910, (1997).
Jurinke et al., (1998) Rapid Comm in Mass Spec., vol. 12, p. 50-52.
Jurinke, C. et al., Adv. Biochem. Eng. Biotechnol., 77: 57-74 (2002).
Jurinke, C. et al., Methods Mol. Biol., 187: 179-192 (2002).
Kario et al., "Genetic Determinants of Plasma Factor VII Activity in the Japanese", Thromb. Haemost., 73:617-622, (1995).
Kirk, et al., "Single Mucleotide polymorphism seeking long term association with complex disease," Nucleic Acids Res. 2002, vol. 30, No. 5, pp. 3295-3311.
Klauck et at., "Coordination of Three Signaling Enzymes by AKAP79, a Mammalian Scaffold Protein", Science, 271:1589-1592 (1996).
Köster et al., "A strategy for rapid and efficient DNA sequencing by mass spectrometry", Nature Biotechnology, 14:1123-1128, (1996).
Köster et al., "Oligonucleotide synthesis and multiples DNA sequencing using chemiluminescent detection", Nucl. Acids Res., Symposium Series No. 24, pp. 318-321, (1991).
Krebs et al., Nucleic Acids Res., 31(7):E37.1-E37.8 (2003).
Kruglyak and Nickerson., Nature Genetics, 27-234-236 (2001).
Kuchino, Y. and S. Nishimura, 180: 154-163 (1989).
Kwoh et al., "Transcription-based amplification system and detection of amplified human immunodeficiency virus type 1 with a bead-based sandwich hybridization format", Proc. Natl. Acad. Sci. USA, 86:1173-1177, (1989).
Kwok et al., Nucl. Acids Res., 18(4): 999-1005 (1990).
Lai, E. et al., Genomics, 54(1): 31-38 (1998).
Laken et al., "Familial colorectal cancer in Ashkenazim due to a hypermutable tract in APC", Nature Genetics, 17:79-83, (1995).
Laken et al., "Genotyping by mass spectrometric analysis of short DNA fragments", Nature Biotechnology, 16:1352-1356 (1998).
Lam et al., "Genetic influence of the R/Q353 genotype on factor VII activity is overwhelmed by environmental factors in Chinese patients with Type II (non-insulin-dependent) dianetes mellitus", Diabetologia, 41:760-766, (1998).
Landegren et al., Genome Res., 8:769-776 (1998).
Lasko et al., "Eukaryotic DNA Ligases", Mutation Research, 236:277-287, (1990).
Le Hellard, Stephanie, et al., SNP genotyping on pooled DNA's: comparison of genotyping technologies and a semi automated method for data storage and analysis, Nucleic Acids Research, (2002) 1-10, 30(15), Oxford University Press.
Lee et al., "Isolation of a cDNA clone for the type I regulatory subunit of bovine cAMP-dependent protein kinase", Proc. Natl. Acad. Sci USA, 80:3608-3612 (1983).
Lehman, I.R., "DNA Ligase: Structure, Mechanism, and Function", Science, 186:790-797, (1974).
Li et al., "DNA ligase 1 is associated with the 21 S complex of enzymes for DNA synthesis in HeLa cells", Nucl. Acids Res., 22(4):632-638, (1994).
Li et al., "High-Resolution MALDI Fourier Transform Mass Spectrometry of Oligonucleotides", Anal. Chem., 68(13):2090-2096, (1996).
Li et al., Cell, 69:915-926 (1992).
Li, J., De-Noising ENMR Spectra by Wavelet Shringkage, Abstract—Eleventh IEEE Symposium on Computer-Based Medical Systems, pp. 252-255 (1998).
Lindahl et al., Annu. Rev Biochem., 61:251-281 (1992).
Litt, M. and J.A. Luty, Nucleic Acids Res., 18(14): 4301 (1990).

Litt, M. et al., NucleicAcids Res., 18(19): 5921 (1990).
Little et al., "Detection of RET proto-oncogene codon 634 mutations using mass spectrometry," J. Mol. Med., 75:745-750, (1997).
Little et al., "Direct detection of synthetic and biologically generated double-stranded DNA by MALDI-TOF MS," International Journal of Mass Spectrometry and IOn Processes, 169-170:323-330, (1997).
Little et al., "Identification of Apolipoprotein E Polymorphisms Using Temperature Cycled Primer Oligo Base Extension and Mass Spectrometry", Eur. J. Clin. Chem. Clin. Biochem., 35(7):545-548, (1997).
Little et al., "Mass spectrometry from miniaturized arrays for full comparative DNA analysis," Nature Medicine, 3(12):1413-1416, (1997).
Little et al., MALDI on a Chip: Analysis of Arrays of Low-Femtomole to Subfemtomole Quantities of Synthetic Oligonucleotides and DNA Diagnostic Products Dispensed by a Piezoelectric Pipet, Anal. Chem., 69:4540-4546, (1997).
Lizardi et al., "Exponential Amplification of Recombinant-RNA Hybridization Probes", Bio/Technology, 6:1197-1202, (1988).
Lu, A.-L. and I.-C. Hsu, "Detection of Single DNA Base Mutations with MismatchRepair Enzymes", Genomics, 14(1): 249-255 (1992).
Luty, J.A. and M. Litt, "Dinucleotide repeat polymorphism at the D 14S45 locus",Nucleic Acids Res., 19(15): 4308 (1991).
Luty, J.A. et al., "Five Polymorphic Microsatellite VNTRs on the Human XChromosome", Am. J. Hum. Genet., 46: 776-783 (1990).
Marotta, C.A. et al., "Preferred sites of digestion of a ribonuclease fromEnterobacter species in the sequence analysis of *Bacillus stearothermophilus* 5Sribonucleic acid", Biochemistry, 12(15): 2901-2904 (1973).
Maxam, A.M. and W. Gilbert, "A new method for sequencing DNA", Proc. Natl.Acad. Sci. U.S.A., 74(2): 560-564 (1977).
McClelland, M. et al., "A single buffer for all restriction endonucleases", NucleicAcid Res., 16(3): 364 (1988).
McKinnon, P.J., Hum. Genet., 75(3): 197-208 (1987).
McKinzie et al., Mutation Research, 517(1-2):209-220 (2002).
McLafferty, F.W., ,Acc. Chem. Res., 27(11): 379-386 (1994).
Miki, K. and Eddy, E.M., "Identification of Tethering Domains for Protein Kinase A Type Ia Regulatory Subunits on Sperm Fibrous Sheath Protein FSC1", J. Biol. Chem., 273(51): 34384-34390, (1996).
Miki, K. and Eddy, E.M., "Single Amino Acids Determine Specificity of Binding Protein Kinase A Regulatory Subunits by Protein Kinase A Anchoring Proteins", J. Biol. Chem., 274(41):29057-29062, (1999).
Minshull and Stemmer Curr. Opin. Chem. Biol., 3(3):284-290 (1999).
Mochly-Rosen et al., "Localization of Protein Kinases by Anchoring Proteins: a Theme in Signal Transduction", Science, 268:247-251 (1 995).
Morris et al., J. Infect. Dis., 171: 954-960 (1995).
Moskovitz et al., "Overexpression of peptide-methionine sulfoxide reductase in *Saccharomyces cerevisiae* and human T cells provides them with high resistance to oxidative stress", Proc. Natl. Acad. Sci. USA, 95:14071-14075, (1998).
Muller et al., "Retention of imprinting of the human apoptosis-related gene TSSC3 in human brain tumors," Human Molecular Genetics, 9(5):757-763, 2000.
Murante, R. S. et al., J. Biol. Chem., 269(2): 1191-1196 (1994).
Nagai, K. and H. C.Thogersen, Nature, 309: 810-812(1984).
Nagamura et al., "Rice molecular genetic map using RFLPs and its applications," Plant Molecular Biology 35: 79-87 (1997).
Nakamura, Y. et al., Science, 235: 1616-1622 (1987).
Nelson et al., "The Accuracy of Quantification from 1D NMR Spectra Using the PIQABLE Algorithm," Journal of Magnetic Resonance 84: 95-109 (1989).
Nikodem, V. and J.R. Fresco, "Protein Fingerprinting by SDS-Gel Electrophoresisafter Partial Fragmentation with CNBr", Anal. Biochem., 97(2): 382-386 (1979).
Nilges et al., "Automated NOESY interpretation with ambiguous distance restraints: the refined NMR solution structure of the pleckstrin homology domain from β-spectrin", J. Mol. Biol., 269:408-422, (1997).

Nishimura, D.Y. and J.C. Murray, "A tetranucleotide repeat for the F13B locus",Nucleic Acids Res., 20(5): 1167 (1992).
Nordhoff, E. et al., "Ion stability of nucleic acids in infrared matrix-assisted laserdesorption/ionization mass spectrometry", Nucleic Acids Res., 21(15): 3347-3357(1993).
Nucleases, Book: 2nd Edition, Linn, S.M. et al. (Eds.), Cold Spring Harbor Laboratory Press (1993).
Okano et al., Cell, 99: 247-257 (1999).
Olek et al., Nucl. Acid Res., 24:5064-5066 (1996).
Paterson, A.H., "Molecular Dissection of Quantitative Traits: Progress and Prospects," Genome Research 321-333 (1995).
Pena et al., "DNA diagnosis of human genetic individuality," J. Mol. Med. 73: 555-564 (1995).
Perlman, P.S. and R.A. Butow, "Mobile Introns and Intron-Encoded Proteins",Science, 246(4934): 1106-1109 (1989).
Pevzner, J. Biomol. Struct. Dyn., 7:63-73 (1989).
Pevzner, PNAS USA, 98(17):9748-9753 (2001).
Ploos et al., "Tetranucleotide repeat polymorphism in the vWF gene", NucleicAcids Res., 18(16): 4957 (1990).
Podhajska, A.J. and Szybalski, W., "Conversion of the FokI endonuclease to a universal restriction enzyme: cleavage of phage M13mp7 DNA at predetermined sites", Gene, 40:175-182, (1985).
Polettini et al., "Fully-automated systematic toxicological analysis of drugs, poisons, and metabolites in whole blood, urine, and plasma by gas chromatography—full scan mass spectrometry," Journal of Chromatography B 713:265-279 (1998).
Polymeropoulos et al., "Tetranucleotide repeat polymorphism at the humanaromatase cytochrome P-450 gene (CYP19)", Nucl. Acids Res., 19(1): 195 (1991).
Polymeropoulos, M.H. et al., "Tetranucleotide repeat polymorphism at the humanc-fes/fps proto-oncogene (FES)", Nucleic Acids Res., 19(14): 4018 (1991).
Polymeropoulos, M.H. et al., Nucl. Acids Res., 19(15): 4306 (1991).
Polymeropoulos, M.H. et al.,, Nucl. Acids Res., 18(24): 7468 (1990).
Ratner, L. et al., "Complete nucleotide sequence of the AIDS virus, HTLV-III",Nature, 313: 227-284 (1985).
Reymer et al., "A lipoprotein lipase mutation (Asn291Ser) is associated with reduced HDL cholesterol levels in premature atherosclerosis", Nature Genetics, 10:28-34, (1995).
Risch, Neil, et al., The Relative Power of Family-Based and Case Control Design for Linkage Disequilibrium Studies of Complex Human Diseases I. DNA Pooling. Genome Research, (1998), 1273-1288, 8, Cold Spring Harbor Laboratory Press.
Robertson et al., Nature Rev. Genet. 1:11-19 (2000).
Rodi et al., Biotechniques 32(Suppl):S62-S69 (2002).
Rojo, M.A. et al., "Cusativin, a new cytidine-specific ribonuclease accumulated inseeds of *Cucumis sativus* L"; Planta, 194: 328-338 (1994).
Ross et al., "Analysis of Short Tandem Repeat Polymorphisms in Human DNA by Matrix-Assisted Laser Desorption/IOnization Mass Spectrometry," Analytical Chemistry, 69:3966-3972, (1997).
Ross et al., "Discrimination of Single-Nucleotide Polymorphisms in Human DNA Using Peptide Nucleic Acid Probes Detected by MALDI-TOF Mass Spectrometry," Analytical Chemistry, 69:4197-4202, (1997).
Ross et al., Nature Biotechnology 16:1347-1351 (1998).
Ross, Phillp, et al., Quantitative Approach to Single Nucleotide Polymorphism Analysis Using MALDI-TOF Mass Spectrometry, BioTechniques, (2000) 620-629, 29(3).
Ruppert et al., "A Filtration Method for Plasmid Isolation Using Microtiter Filter Plates", Anal. Biochem., 230:130-134, (1995).
Sakai et al., American Journal of Human Genetic, 1991 vol. 48, pp, 880-888.
Samson et al., "Resistance to HIV-1 infection in caucasian individuals bearing mutant alleles of the CCR-5 chemokine receptor gene", Nature, 382:722-725, (1996).
Santoro, S. W. and G. F. Joyce, "A general purpose RNA-cleaving DNA enzyme",Proc. Natl. Acad. Sci. U.S.A., 94(9): 4262-4266 (1997).
Saparbaev et al., "*Escherichia coli, Saccharomyces cerevisiae*, rat and human 3-methyladenine DNA glycosylases repair 1, N6-ethenoadenine when present in DNA", Nucl. Acids Res., 23(18):3750-3755, (1995).

Sargent, T.D. et al., "Isolation of Differentially Expressed Genes", MethodsEnzymol., 152: 423-432 (1987).
Saris, C.J.M. et al., "Hydroxylamine Cleavage of Proteins in Polyacrylamide Gels",Anal. Biochem., 132(1): 54-67 (1983).
Sarkar et al., Analytical Biochemistry 186:64-68 (1990).
Sarkar et al., Biotechniques 10(4):436-440 (1991).
Sarkar et al., Moire Inst Owaldo Cruz, 93(51):693-694 (1998).
Sasaki, Tomonari, et al., Precise Estimation of Allele Frequencies of Single Nucleotide Polymorphisms by a Quantitative SSCP Analysis of Pooled DNA, Am. J. Hum, Genet (2001), 214-218, 68, The American Society of Human Genetics.
Schächter et al., "Genetic associations with human longevity at the APOE and ACE loci", Nature Genetics, 6:29-32, (1994).
Scott et al., "Cyclic Nucleotide-Dependent Protein Kinases," Pharmac. Ther. 50:123-145 (1991).
Scott et al., "Type II Regulatory Subunit Dimerization Determines the Subcellular Localization of the CAMP-dependent Protein Kinases," The Journal of Biological Chemistry 265:21561-21566 (1990).
Seela, F. and A. Kehne, "Palindromic octa- and dodecanucleotides containing 2'-deoxytubercidin: synthesis, hairpin formation, and recognition by the endodeoxyribonuclease EcoRI", Biochemistry, 26(8): 2232-2238 (1987).
Senko et al., "Automated Assignment of Charge States from Resolved Isotopic Peaks for Multiply Charged Ions", J. Am. Soc. Mass Spectrom, 6:52-56, (1995).
Senter et al., "Novel photocleavable protein crosslinking reagents and their use in the preparation of antibody-toxin conjugates", Photochem. Photobiol., 42:231-237, (1985).
Sequenom Advances the Industrial Genomics Revolution with the Launch of Its DNA MassArray Automated Process Line, Press Release: Sep. 28, 1998, http://www.sequenom.com/pressrelease.htm.
Sequenom and Gemini Identify Genes Linked to Cardiovascular Disease, Press Release: Nov. 28, 2000, http://www/sequenom.com/ir/ir_prs.asp.
Sequenom Announces Publication of Results From Large-Scale SNP Study With the National Cancer Institute, Press Release: Jan. 16, 2001, http://www/sequenom.com/ir/ir_prs.asp.
Sequenom Completes Design of More Than 400,000 SNP Assays; Mass EXTENDTM Assay Portfolio Covers Majority of SNPs in the Public Domain, Press Release; Oct. 10, 2000, http://www/sequenom.com/ir/ir_prs.asp.
Sequenom, Application Notes from company website: "SNP Discovery Using theMassArray System", http://www. sequenom.com/Assets/pdfs/appnotes/SNP_Discovery_Application_Note.pdf (accessed on Jun. 29, 2004).
Sequenom: Technologies and Tools, located at http://www.sequenom-san.com/tech/tools.html, dated Aug. 29, 1999.
Shchepinov et al., "Matrix-induced fragmentation of P3'-N5'-phosphoroamidate containing DNA: high-throughput MALDI-TOF analysis of genomic sequence polymorphisms", Nucleic Acids Res. 29(18):3864-3872 (2001).
Sheng et al., "Tagged probe interval graphs," Journal of Combinatorial Optimization. 2001 vol. 5, pp. 133-142.
Shriver et al., "Ethnic-Affiliation Estimation by Use of Population-Specific DNA Markers", Am. J. Hum. Genet., 60:957-964 (1997).
Siegert et al., "Matrix-Assisted Laser desorption/Ionization Time-of-Flight Mass Spectrometry for the detection of Polymerase Chain Reaction Containing 7-Deazapurine Moieties", Anal. Biochem., 243:55-65, (1996).
Simoncsits et al., "New rapid gel sequencing method for RNA", Nature, 269: 833-836 (1977).
Siuzdak, G., "The emergence of mass spectrometry in biochemical research", Proc. Natl. Acad. Sci, U.S.A., 91(24): 11290-11297 (1994).
Smith, D. B. and K. S. Johnson, "Single-step purification of polypeptides expressed in *Escherichia coli* as fusions with glutathione S-transferase", Gene, 67: 31-40 (1988).
Smith, L.M., "Sequence from spectrometry: A realistic prospect", Nature Biotechnology, 14:1084-1085, (1996).
Sommer et al., Biotechniques, 12(1):82-87 (1992).
SpectroCHIP BioArray Product Advertisement.

Springer, B. et al., "Two-laboratory collaborative study on identification of mycobacteria: molecular versus phenotypic methods", J. Clin, Microbiol., 34(2):296-303 (1996).

Srinivasan et al., "Matrix-assisted Laser Desorption/Ionization Time-of-flight Mass Spectrometry as a Rapid Screening Method to Detect Mutations Causing Tay-Sachs Disease," Rapid Communications in Mass Spectrometry, 11:1144-1150, (1997).

Stanssens et al., Genomic Res., 14:126-133 (2004).

Stevens, A., "Pyrimidine-specific cleavage by an endoribonuclease of *Saccharomyces cerevisiae*", J. Bacteriol., 1641): 57-62 (1985).

Stomakhin et al., "DNA sequence analysis by hybridization with oligonucleotides microchips;MALDI mass spectrometry identificaiton of 5mers contiguously stacked to microchip oligonucleotides," Nucleic Acids Res. Mar 1, 2000;28(5):1193-1198.

Stults, J. T. et al., "Simplification of high-energy collision spectra of peptides byamino-terminal derivatization", Anal. Chem., 65(13): 1703-1708 (1993).

Sugisaki, H. and Kanazawa, S., "New restriction endonucleases from *Flavobacterium okeanokoites* (Fokl) and *Micrococcus luteus* (Mlul)", Gene, 16:73-78, (1981).

Szybalski et al., "Class-IIS restriction enzymes—a review", Gene, 100:13-26, (1991).

Takio et al., "Primary structure of the regulatory subunit of type II CAMP-dependent protein kinase from bovine cardiac muscle," Proc. Natl. Acad. Sci. USA 79: 2544-25489 (1982).

Tammen et al., "Proteolytic cleavage of glucagon-like peptide-1 by pancreatic β cells and by fetal calf serum analyzed by mass spectrometry", J. Cromatogr. A, 852:285-295, (1999).

Tang et al., "Chip-based genotyping by mass spectrometry", Proc. Natl. Acad. Sci. USA, 96:10016-10020, (1999).

Tang et al., "Matrix-assisted laser desorption/ionization mass spectrometry of immobilized duplex DNA probes", Nucl. Acids Res., 23(16):3126-3131, (1995).

Tang et al., Int. J. Mass. Spectrometry, 226(1):37-54 (2003).

Taranenko et al., "Laser desorption mass spectrometry for point mutation detection," Genetic Analysis: Biomolecular Engineering, 13:87-94, (1996).

Tautz, D., "Hyperyariability of simple sequences as a general source forpolymorphic DNA markers..", Nucleic Acids Res., 17(16): 6463-6471 (1989).

The International SNP Map Working Group, "A Map of human genome sequencevariation containing 1.42 million single nucleotide polymorphisms", Nature,409(6822): 928-933 (2001).

Thompson, J.N., "Fitting robots with white coats", Laboratory Automation and Information Management, 31:173-193, (1996).

Tost et al., Nucl. Acid Res., 31:C50 (2003).

Uracil-DNA Glycosylase (UDG), product description. New England Biolabs. http://circuit.neb.com/neb/products/mod_enzymes/280.html, (Dec. 21, 2000).

Uracil-DNA Glycosylase, product description. Roche Molecular Biochemicals Catalog Version 3, Nov. 1999 http:/biochem.roche.com/pack-insert/1269062a.pdf, (Dec. 21, 2000).

van den Boom et al., "Combined amplification and sequencing in a single reaction using two DNA polymerase with differential incorporation rates for dideoxynucleotides", J. Biochem. Biophys. Methods, 35:69-79, (1997).

van den Boom et al., "Forward and Reverse DNA Sequencing in a Single Reaction", Anal. Biochem., 256:127-129, (1998).

van den Boom et al., Int. J. Mass Spectrom., 238(2):173-188 (2004).

Vanfleteren, J.R. et al., "Peptide Mapping and Microsequencing of ProteinsSeparated by SDS-PAGE After Limited In Situ Acid Hydrolysis", BioTechniques,12(4): 550-557 (1992).

Vath, J. E. et al., "Method for the derivatization of organic compounds at the sub-nanomole level with reagent vapor", Fresenius' Zeitschrfl fur analytische Chemie,331: 248-252 (1988).

Vaughan et al., "Glycosylase mediated polymorphism detection (GMPD)—anovel process for genetic analysis", Genetic Analysis: Biomolecular Engineering, 14:169-175, (1999).

von Wintzingerode, F. et al., "Base-specific fragmentation of amplified 16S rRNAgenes analyzed by mass spectrometry: A tool for rapid bacterial identification",Proc. Natl. Acad. Sci. U.S.A., 99(10): 7039-7044 (2002).

von Wintzingerode, F. et al., "Phylogenetic Analysis of an anaerobic,Trichlorobenzene-Transforming Microbial Consortium", Appl. Environ. Mcrobiol.,65(1): 283-286 (1999).

Wada et al., "Detection of Single-nucleotide Mutations Including Substitutions and Deletions by Matrix-assisted Laser Desorption/Ionization Time-of-flight Mass Spectrometry," Rapid Communications in Mass Spectrometry, 11:1657-1660, (1997).

Wada, J. Mass Spectrometry, 33:187-192 (1998).

Waga et al., "Reconstitution of Complete SV40 DNA Replication with Purified Replication Factors", J. Biol. Chem., 269(14)10923-10934, (1994).

Wagner, D. S. et al., "Derivatization of Peptides to Enhance Ionization Effiencyand Control Fragmentation During Analysis by Fast Atom Bombardment TandemMass Spectrometry", Biol. Mass Spectrom., 20(7): 419-425 (1991).

Wain-Hobson, S. et al., "Nucleotide sequence of the AIDS virus, LAV", Cell, 40:9-17 (1985).

Wang et al., 'Allene Y9 and Y10: low-temperature measurements of line intensity', J. Mol. Spectrosc., 194(20):256-268, (1999).

Wang et al., Science, 280:1077-1082 (1998).

Weber, J.L and P.E. May, "Abundant class of human DNA polymorphisms whichcan be typed using the polymerase chain reaction", Am. J. Hum. Genet., 44: 388-396 (1989).

Weiler et al., "Hybridisation based DNA screening on peptide nucleic acid (PNA) oligomer arrays", Nucl. Acids Res., 25:2792-2799, (1997).

Weissenbach et al., Nature, 359(6358):794-801 (1992).

Wilson, G.G. and Murray, N.E., "Restriction and Modification Systems", Annu. Rev. Genet., 25:585-627, (1991).

Yasuda et al., "Genetic Polymorphisms Detectable in Human Urine: Their Application to Forensic Individualization." Japanese Journal of Legal Medicine 91. 407-41 6 (1997).

Yates, J. Mass Spec., 33:1-19 (1998).

Yen et al., Optically controlled ligand delivery, 1, "Synthesis of water-soluble copolymers containing photocleavable bonds", Makromol. Chem., 190:69-82, (1989).

Yule, A., "Amplification-Based Diagnosis Target TB", Bio/Technology, 12: 1335?1337 (1994).

Zaia, J. and K. Biemann, "Comparison of Charged Derivatives for High EnergyCollision-Induced Dissociation Tandem Mass Spectrometry", J. Am. Soc. MassSpectrom., 6(5): 428-436 (1995).

Zaia, J., in: Protein and Peptide Analysis by Mass Spectrometry, J. R. Chapman (ed.), pp. 29-41, Humana Press, Totowa, N.J., (1996).

Zhou, Guo-Hua et al., "Quantitative detection of single nucleotide polymorphisms for a pooled sample by a bioluminometric assay coupled with modified primer extension reaction (BAMPER), Nucleic Acids Research, (2001) 1-11, 29(19 e93), Oxford University Press.

Zuliani, G. and H.H. Hobbs, "Tetranucleotide repeat polymorphism in the LPLgene", Nucleic Acids Res., 18(16): 4958 (1990).

U.S. Appl. No. 11/997,402, filed Oct. 14, 2008, van den Boom.

Aoki E. et al., "Methylation status of the pI51NK4B gene in hematopoietic progenitors and peripheral blood cells in myelodysplastic syndromes", Leukemia 14(4):586-593 (2000).

Asimakopoulos FA et al., "ABL 1 methylation is a distinct molecular event associated with clonal evolution of chronic myeloid leukemia" Blood 94(7):2452-2460 (1999).

Bair and Tibshirani, PloS Biol 2:E108 (2004).

Bullinger L. et al. N Engl J Med 350:1605-16 (2004).

Chan et al., Oncogene 22:924-934 (2003).

Chen et al., Analytical Biochemistry, 1996, vol. 239, p. 61-69.

Colella et al. Biotechniques. Jul. 2003;35(1):146-50.

Costello et al., Nature Gent., 24:132-138 (2000).

Dohner et al. J Clin Oncol 20:3254-61 (2002).

Dupont JM, Tost J, Jammes H, and Gut IG. Anal Biochem, Oct 2004; 333(1): 119-27.

Fajkusova L. et al., "Detailed Mapping of Methylcytosine Positions at the CpG Island Surrounding the Pa Promoter at the bcr-abl Locus in CML Patients and in Two Cell Lines, K562 and BV173" Blood Cells Mol. Dis. 26(3):193-204 (2000).

Feinberg, AP Nat Genet 27:9-10 (2001).

Frigola et al. Nat Genet. May 2006;38(5):540-9.

Frohling et al. Blood 100:4372-80 (2002).

Gebhard et al. Cancer Res. Jun 15, 2006;66(12):6118-28.
Genebank Accession No. NM_153620.
Genebank Accession No. AB025106.
Genebank Accession No. AB040880.
Genebank Accession No. BC013998.
Genebank Accession No. NM_001031680.
Genebank Accession No. NM_001394.
Genebank Accession No. NM_001614.
Genebank Accession No. NM_003998.
Genebank Accession No. NM_004350.
Genebank Accession No. NM_004360.
Genebank Accession No. NM_005522.
Genebank Accession No. NM_005766.
Genebank Accession No. NM_033317.
Issa JP, Nat Rev Cancer 4:988-93 (2004).
Kaneko et al., Gut 52:641-646 (2003).
Laird, P.W. Nature Reviews Cancer 3, 253-266 (2003).
Litz C. E. et al., "Methylation status of the major breakpoint cluster region in Philadelphia chromosome negative leukemias" Leukemia 6(1):35-41 (1992).
Nosaka, K. et al., "Increasing methylation of the CDKN2A gene is associated with the progression of adult T-cell leukemia", Cancer Res. 60(4):1043-1048 (2000).
Puskas et al. Genome Research, 1995, vol. 5, p. 309-311.
Schuette et al. Journal of Parmaceutical and Biomedical Analysis, 1995, vol. 13, p. 1195-1203.
Strathdee, et al., Am. J. Pathol. 158:1121-1127 (2001).
Tooke N and Pettersson M. IVDT. Nov. 2004; 41.
Toyota, M. et al., Blood 97:2823-9 (2001).
Uhlmann, K. et al. Electrophoresis 23:4072-4079 (2002).
Valk PJ et al. N Engl J Med 350:1617-28 (2004).

* cited by examiner

Figure 1(B)

```
1.........11........21........31........41........51........
GGGTTTGGGAGAGTTTGTGAGGTCGTTTATCGTTTGTTAGTAGAGTGCGTTCGCGAGTCG
61........71........81........91........101.......111.......
TAAGTATAGTTCGGTAATATGCGGTTTTAGATAGGAAAGTGGTCGCGAATGGGATCGGG
121.......131.......141........151.......161.......171.......
GTGTTTAGCGGTTGTGGGATTTTGTTTTGCGGAAATCGCGGTGACGAGTATAAGTTCGG
181.......191.......201.......211.......221.......231.......
TTAATTGGATGGGAATCGGTTTGGGGGGTTGGTATCGCGTTTATTAGGGGGTTTGCGGTA
241.......251.......261.......271.......281.......291.......
TTTTTTTTTGTTTTTAGTATTTTATTTTTATTTTTAGGAACGTGAGGTTTGAGTCGTG
301.......311.......321.......331........341........351.......
ATGGTGGTAGGAAGGGGTTTTTTGTGTTATTCGAGTTTTTAGGGATTCGTAGTTGGTTTT
361.......371.......381.......391.......401.......411.......
TAGTTATGTGTAAAGTATGTGTAGGGCGTTGGTAGGTAGGGAGTAGTAGGTATGGT
```

```
1.........11........21........31........41........51........
GGGTTTGGGAGAGTTTGTGAGGTTGTTTATTGTTTGTTAGTAGAGTGTGTTTGTGAGTTG
61........71........81........91........101.......111.......
TAAGTATAGTTTGGTAATATGTGGTTTTAGATAGGAAAGTGGTTGTGAATGGGATTGGG
121.......131.......141.......151.......161.......171.......
GTGTTTAGTGGTTGTGGGATTTTGTTTTGTGGAAATTGTGGTGATGAGTATAAGTTTGG
181.......191.......201.......211.......221.......231.......
TTAATTGGATGGGAATTGGTTTGGGGGGTTGGTATTGTGTTTATTAGGGGGTTTGTGGTA
241.......251.......261.......271.......281.......291.......
TTTTTTTTTGTTTTTAGTATTTTATTTTTATTTTTAGGAATGTGAGGTTTGAGTTGTG
301.......311.......321.......331.......341.......351.......
ATGGTGGTAGGAAGGGGTTTTTTGTGTTATTTGAGTTTTTAGGGATTTGTAGTTGGTTTT
361.......371.......381.......391.......401.......411.......
TAGTTATGTGTAAAGTATGTGTAGGGTGTTGGTAGGTAGGGAGTAGTAGGTATGGT
```

Figure 1(C)I

| Molecular Mass in Da | CpG island position | Cleavage product type | Cleavage product composition and origin |
|---|---|---|---|
| 653.41 | OOMR | MAIN | 5OH-AC-3p @447 |
| 669.41 | OOMR | MAIN | 5OH-GC-3p @227; 5OH-GC-3p @169; 5OH-GC-3p @116; 5OH-GC-3p @63 |
| 932.60 | OOMR | MAIN | 5OH-TTC-3p @431 |
| 1236.8 | OOMR | MAIN | 5OH-TTTC-3p @434 |
| 1277.81 | OOMR | ANCH | 5OH-GTTC-3p @59 |
| 1535.07 | 1 | LAST | 5OH-TAAAT-3OH @450 |
| 1648.03 | 2 | MAIN | 5OH-GAGTC-3p @65 |
| 1993.24 | 3 | MAIN | 5OH-GGTGAC-3p @171 |
| 2215.41 | 4 | ANCH | 5OH-GTTTATC-3p @35 |
| 2306.45 | 5 | MAIN | 5OH-GGAAATC-3p @162 |
| 3260.05 | 6 | ANCH | 5OH-GGTAATATGC-3p @83 |
| 3301.07 | 7 | MAIN | 5OH-GAATGGGATC-3p @118 |
| 3623.03 | 8 | ANCH | 5PPP-GGGAGAAGGC-3p @0 |
| 3893.46 | 9 | ANCH | 5OH-GAGTATAAGTTC-3p @177 |
| 3941.46 | 10 | ANCH | 5OH-GGGGTGTTTAGC-3p @128 |
| 4197.66 | 11 | ANCH | 5OH-GTAAGTATAGTTC-3p @70 |
| 4574.86 | 12* | ANCH | 5OH-GTGAGGTTTGAGTC-3p @294 |
| 5167.26 | 13* | ANCH | 5OH-GAGTTTTTAGGGATTC-3p @343 |
| 5512.47 | 14 | ANCH | 5OH-GTTTGTTAGTAGAGTGC-3p @42 |
| 5832.66 | 15 | ANCH | 5OH-GTTTATTAGGGGGTTTGC-3p @229 |
| 6211.9 | 16 | MAIN | 5OH-GGTTAATTGGATGGGAATC-3p @189 |
| 6234.88 | 17 | MAIN | 5OH-GGTTTGGGGGGTTGGTATC-3p @208 |
| 7106.46 | 18 | MAIN | 5OH-GGTTGTGGGGATTTTGTTTTGC-3p @140 |
| 7494.71 | 19 | MAIN | 5OH-GGTTTTTAGATAGGAAAGTGGTC-3p @93 |
| 8192.12 | 20 | MAIN | 5OH-TGGGTTTGGGAGAGTTTGTGAGGTC-3p @10 |
| 9870.16 | OOMR | MAIN | 5OH-GTTGGTAGGTAGGGAGTAGTAGGTATGGTC-3p @398 |
| 11366.1 | OOMR | MAIN | 5OH-GTGATGGTGGTAGGAAGGGGTTTTTTGTGTTATTC-3p @308 |
| 12616.9 | OOMR | MAIN | 5OH-GTAGTTGGTTTTTAGTTATGTGTAAAGTATGTGTAGGGC-3p @359 |
| 14763.4 | OOMR | MAIN | 5OH-GGTATTTTTTTTTGTTTTTTAGTATTTTATTTTTATTTTTTAGGAAC-3p @247 |

Figure 1 (C) II

| Molecular Mass in Da | CpG island position | Cleavage product type | Cleavage product composition and origin |
|---|---|---|---|
| 324.208 | OOMR | MAIN | 5OH-C-3p @449; 5OH-C-3p @430 |
| 524.192 | OOMR | ACYC | 5PPP-G-3OH @0 |
| 653.417 | OOMR | MAIN | 5OH-AC-3p @447 |
| 869.401 | OOMR | ACYC | 5PPP-GG-3OH @0 |
| 932.601 | OOMR | MAIN | 5OH-TTC-3p @431 |
| 1214.61 | OOMR | ACYC | 5PPP-GGG-3OH @0 |
| 1236.8 | OOMR | MAIN | 5OH-TTTC-3p @434 |
| 1889.03 | A | DBLC | 5PPP-GGGAGAAGGC-3p @0 |
| 2547.45 | B | ACYC | 5PPP-GGGAGAA-3OH @0 |
| 2889.83 | C | MAIN | 5OH-TATAGTGTC-3p @438      derived from PCR primer tag |
| 2892.66 | C | ACYC | 5PPP-GGGAGAAG-3OH @0 |
| 3237.87 | D | ACYC | 5PPP-GGGAGAAGG-3OH @0 |
| 3623.03 | E | MAIN | 5PPP-GGGAGAAGGC-3p @0      derived from PCR primer tag |
| 135810 | OOMR | MAIN | 5OH-TGGGTTTGGGAGAGTTTGTGAGGTTGTTTATTGTTTGTTAGT AGAGTGTGTTTGTGAGTTGTAAGTATAGTTTGGTAATATGTGGTT TTTAGATAGGAAAGTGGTTGTGAATGGGATTGGGGTGTTTAGTGG TTGTGGGGATTTTGTTTTGTGGAAATTGTGGTGATGAGTATAAGTT TGGTTAATTGGATGGGAATTGGTTTGGGGGGTTGGTATTGTGTTTA TTAGGGGGTTTGTGGTATTTTTTTTTGTTTTTTAGTATTTTATTTTTA TTTTTTAGGAATGTGAGGTTTGAGTTGTGATGGTGGTAGGAAGGGG TTTTTTGTGTTATTTGAGTTTTTAGGGATTTGTAGTTGGTTTTTAGTT ATGTGTAAAGTATGTGTAGGGTGTTGGTAGGTAGGGAGTAGTAGGT ATGGTAGC-3p @10 |

Cleavage product characterization legend:
MAIN = regular cleavage product
OOMR = out of mass range (molecular mass either too low or too high to be detected within the automated data acquisition)
DBLC = double charged molecular ion species (at half mass of parent molecular ion)
ACYC = Abortive cycling (incomplete transcription products generated during the first 10 nt of transcription)

US 7,608,394 B2

METHODS AND COMPOSITIONS FOR PHENOTYPE IDENTIFICATION BASED ON NUCLEIC ACID METHYLATION

RELATED APPLICATIONS

This application is a continuation-in-part of U.S. provisional patent application No. 60/556,632 to Mathias Ehrich and Dirk Van den Boom filed 26 Mar. 2004, entitled "BASE SPECIFIC CLEAVAGE OF METHYLATION-SPECIFIC AMPLIFICATION PRODUCTS IN COMBINATION WITH MASS ANALYSIS;". These applications are related to subject matter in U.S. application Ser. No. 10/272,665 to Andreas Braun, Christian Jurinke and Dirk van den Boom, filed Oct. 15, 2002, entitled "METHODS FOR GENERATING DATABASES AND DATABASES FOR IDENTIFYING POLYMORPHIC GENETIC MARKERS."

FIELD OF THE INVENTION

The present invention relates to diagnostic applications in the field of medicine and biotechnology. More specifically to methods and compositions for identification of an organism, tissue or cell phenotype based on the methylation state of nucleic acids.

BACKGROUND

Genetic information is stored not only in the sequential arrangement of four nucleotide bases, but also in covalent modification of selected bases (see, e.g., Robertson et al., *Nature Rev. Genet.* 1:11-19 (2000)). One of these covalent modifications is methylation of cytosine nucleotides, particularly cytosines adjacent to guanine nucleotides in "CpG" dinucleotides. Covalent addition of methyl groups to cytosine within CpG dinucleotides is catalyzed by proteins from the DNA methyltransferase (DNMT) family (Amir et al., *Nature Genet.* 23:185-88 (1999); Okano et al., *Cell* 99:247-57 (1999)). In the human genome, CpG dinucleotides are generally under represented, and many of the CpG dinucleotides occur in distinct areas called CpG islands. A large proportion of these CpG islands can be found in promoter regions of genes. The conversion of cytosine to 5'-methylcytosine in promoter associated CpG islands has been linked to changes in chromatin structure and often results in transcriptional silencing of the associated gene. Transcriptional silencing by DNA methylation has been linked to mammalian development, imprinting and X-Chromosome inactivation, suppression of parasitic DNA and numerous cancer types (see, e.g., Li et al., *Cell* 69:915-26 (1992); Okano et al., *Cell* 99:247-57 (1999)). Detected changes in the methylation status of DNA can serve as markers in the early detection of neoplastic events (Costello et al., Nature Genet. 24:132-38 (2000)).

Studies demonstrating the practical use of DNA methylation analysis in a clinical environment are scarce. This is due, at least in part, to the technical limitations facing DNA methylation research. A few DNA methylation analysis techniques have been used, but each method has its limitations. See, for example, U.S. Pat. No. 6,214,556 directed to methods for producing complex DNA methylation fingerprints. The methods of this patent amplify fragments of genomic DNA that have been treated with bisulfite using with degenerated oligonucleotides or oligonucleotide that are complimentary to adaptor oligonucleotides that have been ligated to the fragmented genomic DNA. Methods such as these are prone to false positive results and are limited in accurate methylation assessment to a single cytosine position per analysis. Often times they require large amounts of high quality genomic DNA and are labor intensive.

Since DNA methylation has a variety diagnostic uses, there is a need for reliable, cost effective, high throughput DNA methylation analysis tools and methods to evaluate potential methylated sites, to associate methylation sites with disease, and to develop prognostic methylation markers. Therefore it is an object herein to provide methylated nucleotide identification methods, and products therefor.

BRIEF DECRIPTION OF THE DRAWINGS

FIG. 1: (A) displays mass signals generated by cytosine specific cleavage of the forward transcript of the IGF2/H19 region (upper spectral analysis is the methylated template; lower spectral analysis is the non-methylated template). (B) shows the IGF2/H19 RNA transcript sequence wherein each CpG sequence is methylated (upper sequence) and the same RNA transcript sequence where none of the CpG sequences (lower sequence). (C) shows the cleavage products of mass signals generated by cytosine specific cleavage of the forward transcript of IGF2/H19 in both the methylated (I) and non-methylated (II) transcript sequences.

Figure 2:
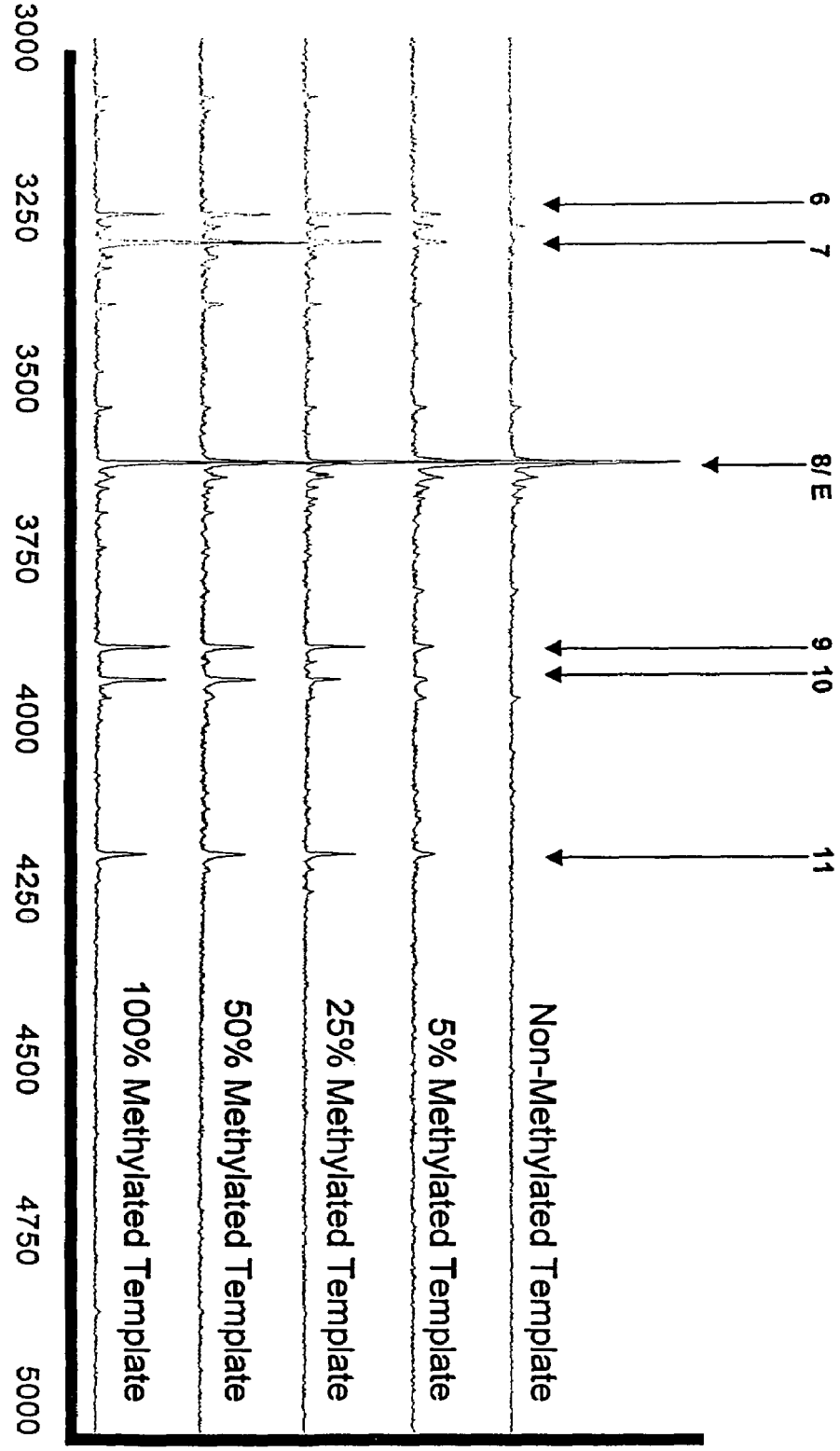

FIG. 2: is an overlay of mass signal patterns generated by cytosine specific cleavage of the forward transcript of the IGF2/H19 region.

Figure 3:
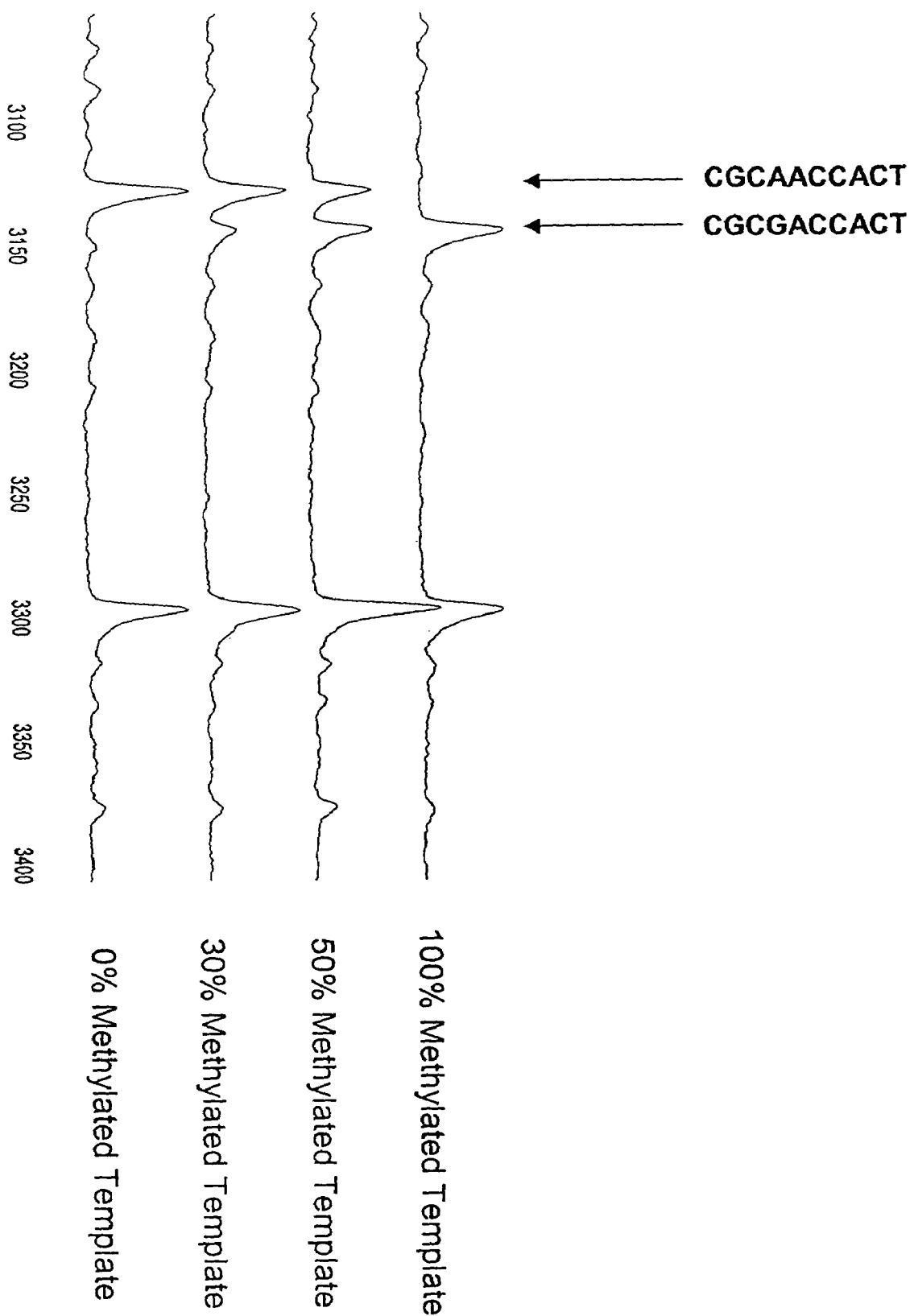

FIG. 3: is an overlay of mass spectra generated by uracil specific cleavage of the reverse transcript of the IGF2/H19 region.

Figure 4:
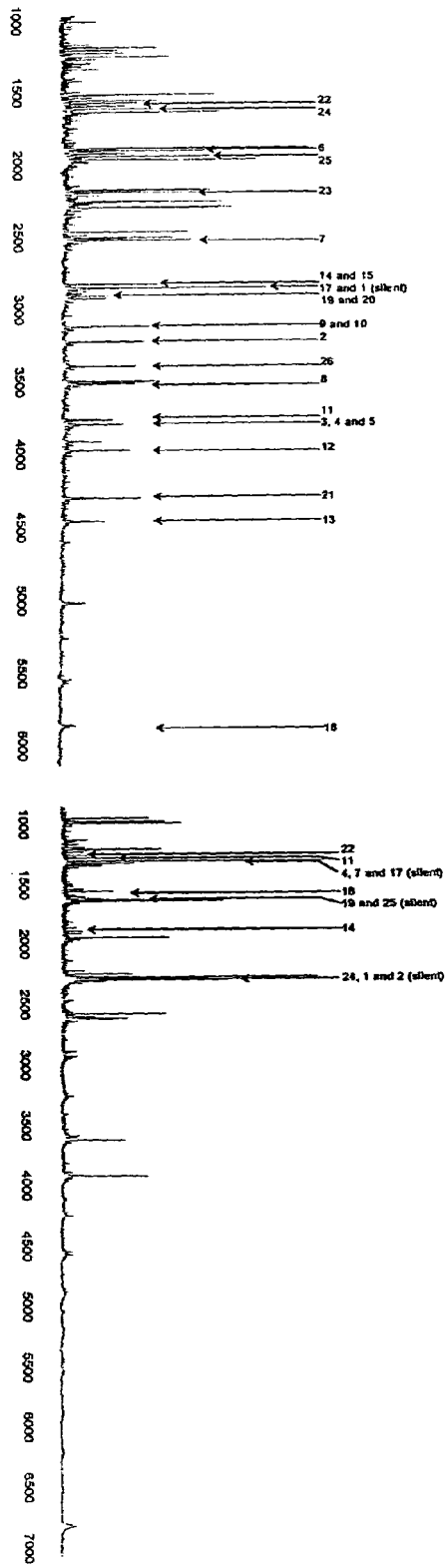
Figure 4:
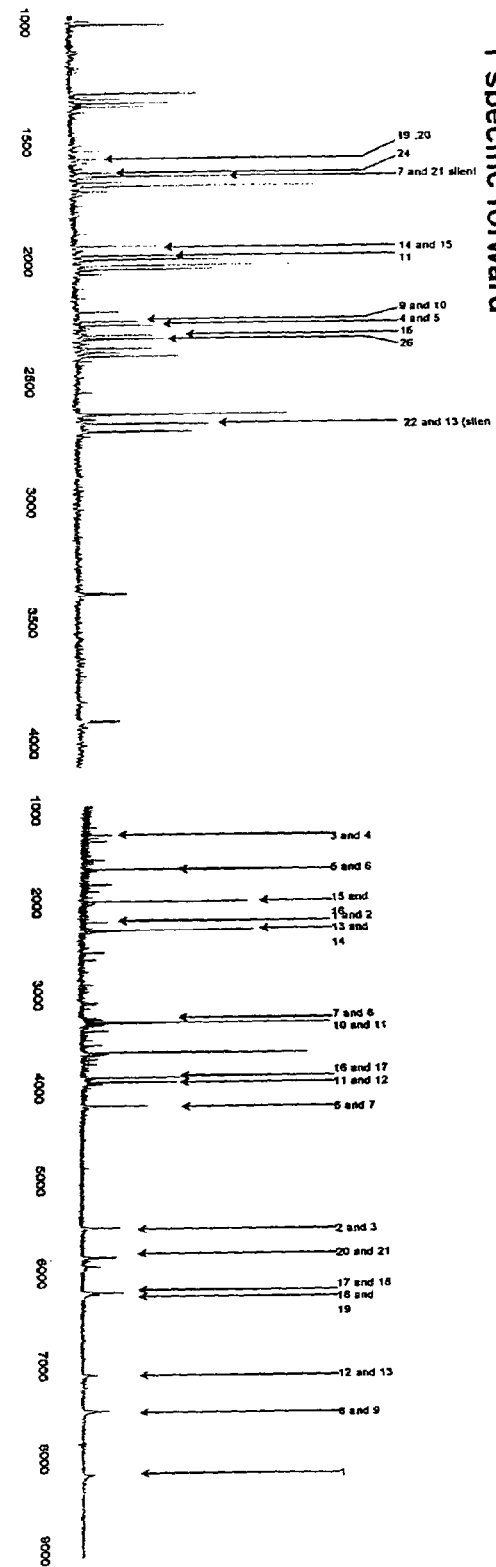

FIG. 4: depicted are mass spectra representing all four base-specific cleavage reactions of the IGF/H19 amplicon. Numbers correspond to the CpG positions within this target region. Arrows point at the mass signals that indicate the presence of a methylated Cytosine at the marked position. All methylated CpG's in the selected region can be identified by one or more mass signals.

Figure 5:
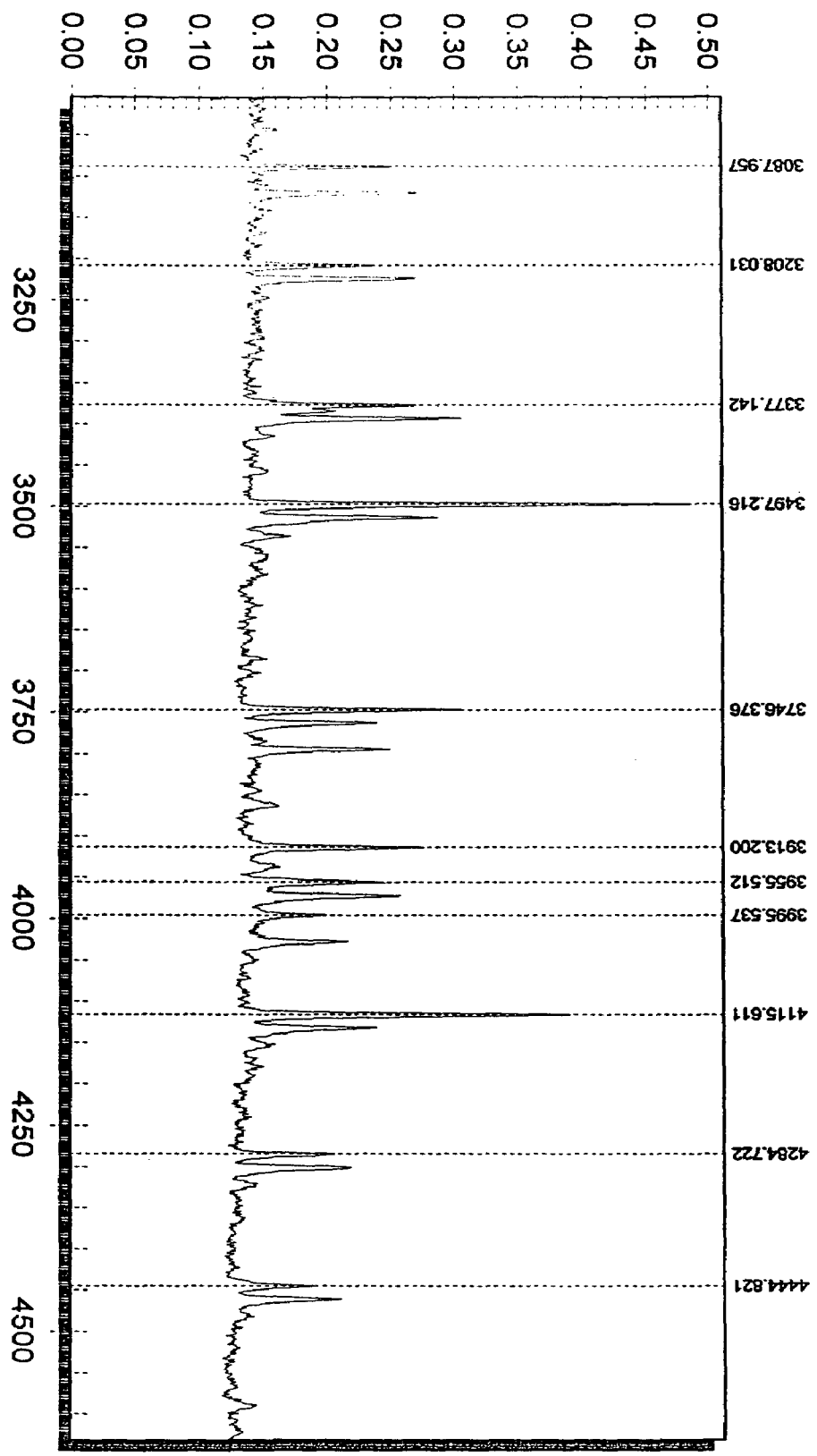

FIG. 5: depicted are mass spectra generated by uracil specific cleavage of the reverse transcript of the IGF2/H19 region. Genomic DNA was used for amplification. Dotted lines mark the position of mass signals representing non-methylated CpG's. Signals with 16 Dalton shift (or a multitude thereof) represent methylation events. The area-under-the-curve ratio of methylated versus non-methylated template approximates to 1, as one expects for hemi-methylated target regions.

Figure 6:
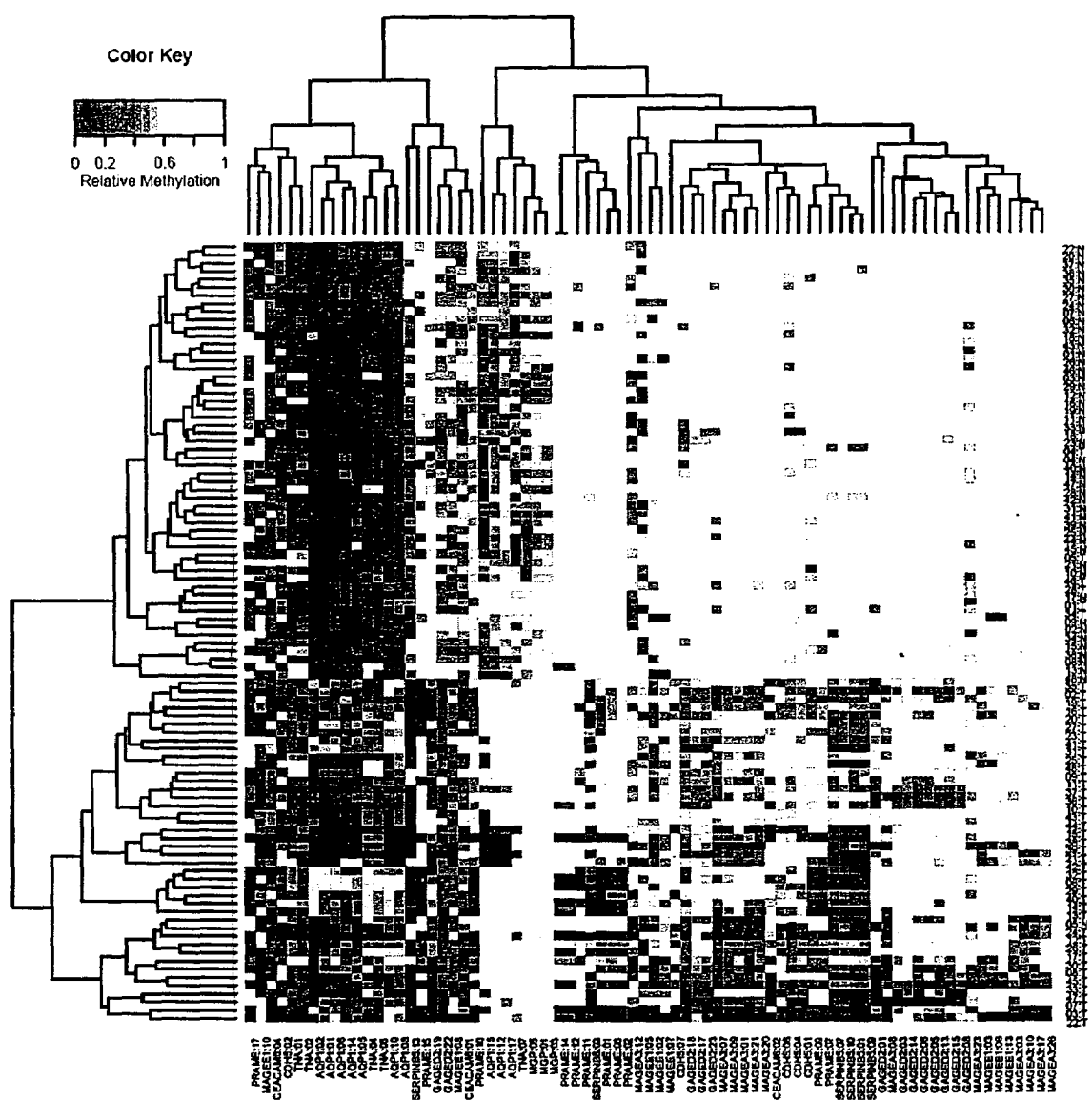

FIG. 6: Show the results of a two-way hierarchical cluster analysis of the relative methylation of 76 CpG fragments (columns) measured on 96 tissue samples from 48 lung cancer cases (rows). Tissue samples are identified on the right vertical axis as the patient number (1-48) and the tissue type (N=normal, T=tumor). CpG fragments are identified at the bottom horizontal axis as the gene and the fragment number within the gene. The relative methylation of each fragment within each sample is presented in the central image plot with values ranging from zero (black or dark grey) to one (white or light grey). Note that missing values are represented as grey.

Figure 7:
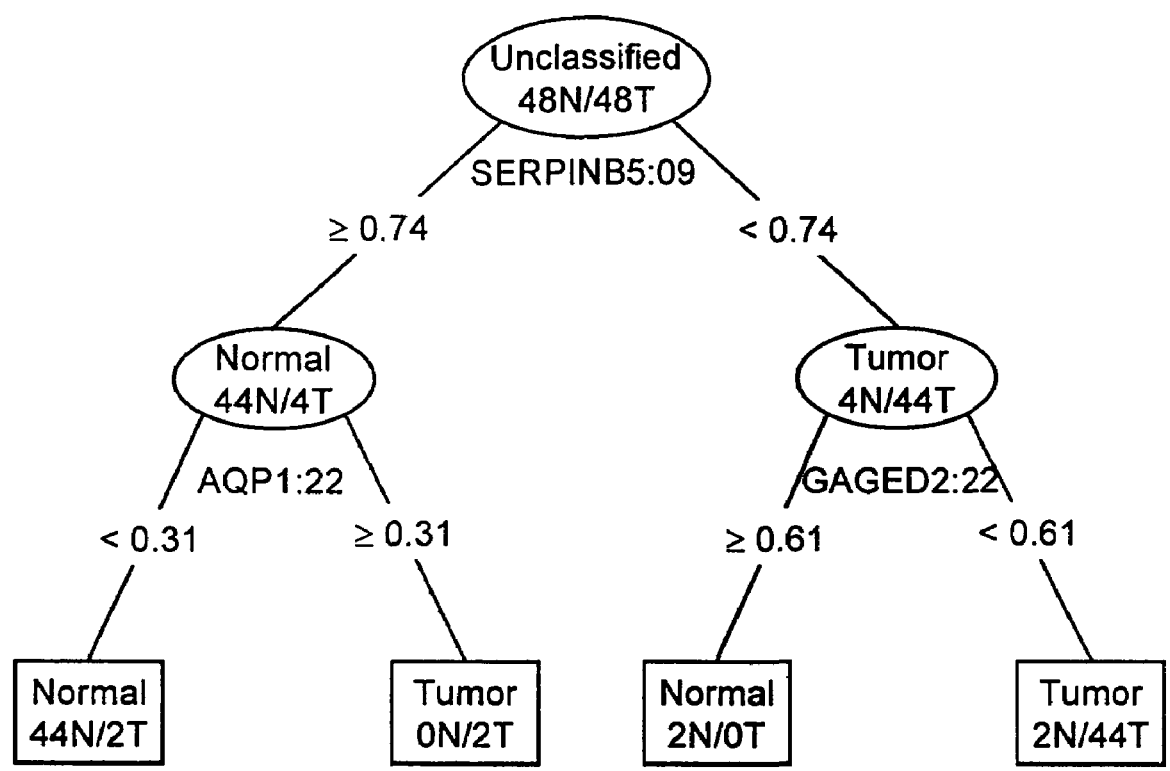

FIG. 7: Is a tree-based classifier constructed to use relative CpG fragment methylation to discriminate normal from tumor tissue. Internal nodes are represented as ovals and terminal nodes as rectangles. The numbers of normal and tumor samples are indicated within each node. The CpG fragment that best discriminates the normal from tumor tissues within each internal node is indicated below the node, as are the selected relative methylation values. For example, unclassified samples (root node) are optimally discriminated by dividing them according to relative methylation values for fragment 9 of the SERPINB5 gene. Here, 44 tissues with values greater than 0.74 were normal and 44 tissues with values less than 0.74 were tumors.

SUMMARY

The present invention provides a method for identifying an unknown phenotype of a tissue or cell that correlates with changes in the methylation state of the tissue or cell comprising, treating a nucleic acid sample from said tissue or cell with a reagent that modifies unmethylated cytosine to produce uracil, amplifying a nucleic acid target gene region using at least one primer that hybridizes to a strand of the nucleic acid target gene region producing amplified nucleic acids, determining the characteristic methylation state of the nucleic acid target gene region by base specific cleavage and identification of methylation sites of the amplified nucleic acids; and comparing the ratio of methylated cytosine to unmethylated cytosine for each of the methylation sites of the characteristic methylation state of the sample from the tissue or cell nucleic acid to the ratio of methylated cytosine to unmethylated cytosine for each of the methylation sites of a tissue or cell nucleic acid sample of the same type having a known phenotype thereby identifying the unknown phenotype.

In preferred aspects of the present invention this method may be utilized to detect the presence or absence of a disease in a tissue or cell that correlates with changes in the methylation state of said tissue or cell, classify the susceptibility of a tissue or cell to a disease wherein said disease is correlated with changes in the methylation state of said tissue or cell or predict the probability of a subjects survival wherein said survival is correlated with changes in the methylation state of said subjects tissue or cell.

In one embodiment the unknown phenotype of a tissue or cell that correlates with changes in the methylation state of said tissue or cell is a disease state. Preferably the disease state is a cancer, a cardiovascular disease (CVD), a central nervous system disease (CNS), a metabolic disease, aging, morbidity, osteoarthritis, an infection or a drug response. If the disease state is cancer it is preferably a lung cancer, a gastrointestinal cancer, a genitourinary tract cancer, breast cancer, a liver cancer, a bone cancer, cancers of the nervous system, a gynecological cancer, a hematologic cancer skin cancer or an adrenal gland cancer. When the cancer is a gastrointestinal cancer it is preferably esophagus squamous cell carcinoma, esophagus adenocarcinoma, esophagus leiomyosarcoma, esophagus lymphoma, stomach carcinoma, stomach lymphoma, stomach leiomyosarcoma, pancreas ductal adenocarcinoma, pancreas insulinoma, pancreas glucagonoma, pancreas gastrinoma, pancreas carcinoid tumors, pancreas vipoma, small bowel adenocarcinoma, small bowel lymphoma, small bowel carcinoid tumors, small bowel Karposi's sarcoma, small bowel lieomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, and large bowel leiomyoma.

When the cancer is a genitourinary tract cancer it is preferably kidney adenocarcinoma, kidney nephroblastoma, kidney lymphoma, kidney leukemia, bladder and urethra squamous cell carcinoma, bladder and urethra transitional cell carcinoma, bladder and urethra adenocarcinoma, prostate addenocarcinoma, prostate sarcoma, testis seminoma, testis teratoma, testis embryonal carcinoma, testis teratocarcinoma, testis choriocarcinoma, testis sarcoma, testis interstitial cell carcinoma, testis fibroma, testis fibroadenoma, testis adenomatoid tumors, or testis lipoma.

When the cancer is a liver cancer it is preferably a liver hepatoma, liver hepatocelluar carcinoma, liver cholangiocarcinoma, liver hepatoblastoma, liver angiosarcoma, liver hepatocellular adenoma, and liver hemangioma.

When the cancer is a bone cancer it is preferably a bone osteogenic sarcoma, bone fibrosarcoma, bone malignant fibrous histiocytoma, bone chondrosarcoma, Ewing's sarcoma, bone malignant lymphoma, bone multiple myeloma, bone malignant giant cell tumor chordoma, bone osteochronfroma, bone benign chondroma, bone chondroblastoma, bone chondromyofibroma, bone osteoid osteoma, and bone giant cell tumor.

When the cancer is a cancer of the nervous system it is preferably skull osteoma, skull hemangioma, skull granuloma, skull xanthoma, skull osteitis, skull defomians, meningioma, meningiosarcoma, bliomatosis, brain astrocytoma, brain medulloblastoma, brain glioma, brain ependymoma, brain germinoma, brain glioblastoma multiform, brain oligodendroglioma, brain schwannoma, brain retinoblastoma, brain congenital tumors, spinal cord neurofibroma, spinal cord memingioma, spinal cord glioma, and spinal cord sarcoma.

When the cancer is a gynocological cancer it is preferably a uterus endometrial carcinoma, cervical carcinoma, pre-tumor cervical dysphasia, ovarian carcinoma, serous cystadenocarcinoma, mucinous cystadenocarcinoma, unclassified ovarian carcinoma, ovarian granulosa-thecal cell tumors, SertoliLeydig tumors, ovarian dysgerminoma, ovarian malignant teratoma, vulva squamous cell carcinoma, vulva intaepithelial carcinoma, vulva adenocarcinoma, vulva fibrosarcoma, vulva melanoma, vagina clear cell carcinoma, vagina squamous cell carcinoma, botryoid sarcoma, and fallopian tube carcinoma.

When the cancer is a hematologic cancer it is a blood myeloid leukemia, blood acute lymphoblastic leukemia, blood chronic lymphocytic leukemia, blood myeloproliferative diseases, blood multiple myeloma, blood myelodysplasic syndrome, Hodgkin's disease and non-Hodgkin's lymphoma.

When the cancer is a skin cancer it is preferably a skin malignant melanoma, skin basal cell carcinoma, skin squamous cell carcinoma, skin Karposi's sarcoma, skin moles dysplasic nevi, skin lipoma, skin angioma, dematofibroma and skin keloids, psoriasis.

When the cancer is a lung cancer it is preferably a lung squamous cell carcinoma, lung undifferentiated small cell carcinoma, lung undifferentiated large cell carcinoma, lung adenocarcinoma, alveolar carcinoma, bronchial adenoma, lung sarcoma, lung lymphoma, lung chondromatous hanlartoma and lung inesothelioma.

When the disease is a metabolic disease it is preferably diabetes.

In another embodiment the reagent that modifies unmethylated cytosine to produce uracil is bisulfite.

In yet another embodiment the nucleic acid target gene is IGF2/H19, CADHERIN13, MAGEA3, PRAME, MGP, MAGEE1, CEACAM6, GAGED2, SerpinB5, TNA, AQP1, CDH5, DAPK1, MGMT, CDKN2A, RASSF1, CACNA2D2, TACSTD1, SDK2, ADAMTS8, GJB2, ESAM, FGG CpG1, SELENBP1, MAGEA4, EDNRB I2, CLIC3, PAGE5 FOSB, ZFP36, GPC3, IGSF4, STEAP, CAV1, IGF2R, PLAU, PBP, CLIC5, ROHDBT2, JUP, ABCC11, RODH, S100A2, CDH3, WIF-1, GAGE1B or MAGEA1. More specifically, the nucleic target gene region is chr16:82397485-82400484, chrX:149686099-149687598, chr22:21225987-21227486, chr12:14559868-15319242, chrX:137726468-140726467, chr19:46710046-47160045, chrX:51057294-51590627, chr3:44796503-44976502, chr7:30456743-30861742, chr16:66026768-66269767, chr18:60861193-60996192, chr9:83666822-83667821, chr10:131194125-131195124, chr9:21964618-21966117, chr3:50228037-50233099, chr3:50314945-50476944, chr2:47552926-47554425, chr17:71816325-71902844, chr11:130330360-130335359, chr5:180082544-180084043, chr13:19689358-19699482, chr11:124654685-124668369 chr4:155933296-156048654, chr1:148082308-148159211, chrX:148774790-148904569, chr13:77351803-77621802, chr9:133327587-133337586, chrX:53684992-54018324, chr19:50645115-50648489, chr19:44572554-44573553, chrX:131064581-131065580, chr11:115408779-115410278, chr7:89380761-89382260, chr7:115704514-115706013, chr6:160222309-160223808, chr10:75562090-75563589, chr12:118355527-118357026, chr6:45983175-45986466, chr8:22676411-22677910, chr17:39851715-39852714 chr16:48015318-48016317, chr12:56859865-56886864, chr1:150353913-150383912, chr16:68413396-68414895, chr12:65231587-65233086, chrX:48140000-48350000 or chrX:149994325-150102324.

In another embodiment the at least one primer that hybridizes to a strand of said nucleic acid target gene may have the sequence GGGTTTTGATTTTGATTTTTGTTATAG (SEQ ID NO.: 14), TTTGTTTTTGGTTGGGTAATTTTTG (SEQ ID NO.: 25), GGGTTTGTTTTTAGAAGAGAAAATGG (SEQ ID NO.: 13), ATATTTTTGGAAAAAGGAGAGTGGG (SEQ ID NO.: 17), GGGATTTTTTGTGTGGTGTTGATAG (SEQ ID NO.: 23), GGGATTTGGGAAGGAGTATAGGATAG (SEQ ID NO.: 27), TGGAGGTTTTTTGGAAGTTGTGTAG (SEQ ID NO.: 30), GGGTGTTTTTTGGTAGAGAGGTTTT (SEQ ID NO.: 38), TATTTAGAGGAGGTTTGTGTGGTGTG (SEQ ID NO.: 41), TTTTGAGGTAGAGGGTGAGGAGTAG (SEQ ID NO.: 42), AGGCTGTTAGTTTTTATTTTATTTTAAT (SEQ ID NO.: 48), TTGTTGATTTATTTGGGAAGTTGGTT (SEQ ID NO. 1), GTTAGGAATGTGGTTTTGGGGATT (SEQ ID NO.: 2), GTTGGTTTGGGGGTTTTGATTAG (SEQ ID NO.: 3), TGTTTTTTAAATTTTTTGGAGGGAT (SEQ ID NO.: 4), GTTGTTTTTTGGTTGTTTTTTT (SEQ ID NO.: 5), GGGGTTTGAAGATTTTGTTTTGTTTTAT (SEQ ID NO.: 9), GGAGGGGAGTTTATTTATTTTTTTAATTTT (SEQ ID NO.: 10), TTGGTGATAGTTAGGTAGGTGGAAGTTT (SEQ ID NO.: 18), GAGGTTTTTAGTTTTATTTGTAGGT (SEQ ID NO.: 20), TTGGGGTTTTTTGAGAGTAGGTAGGT (SEQ ID NO.: 33), GGTTTTTGGGTTTTTAGAGTTTTT (SEQ ID NO.: 39), GGGAGGGAAATTATGGTTTTTTTG (SEQ ID NO.: 46), GGAGTTGGGAATTTTAAGGTAGGTGA (SEQ ID NO.: 11), AGGGAAGAAGTGATTTGGTTGATG (SEQ ID NO.: 15), TTTTGGTTTGAGGGGGTTGTATTTA (SEQ ID NO.: 19), GGGAGTTGTAGTTTAGTTAGTTAGGGAGTA (SEQ ID NO.: 34), GGTTGGGAGTTTTGATAAGGGGTAT (SEQ ID NO.: 35), TGGAGTGGGTAAGATTATTGTAAGTATGAT (SEQ ID NO.: 36), GGATTTGTAGGTTGGGGTTTTTT (SEQ ID NO.: 6), TTGTTTTTGGGGTTTTGTTTTTATTTT (SEQ ID NO.: 7), GGTAGTGGTTTTGAGGAGTAAGAGA (SEQ ID NO.: 8), TTGGGTAAATTTTAAGATTGTTTTTA (SEQ ID NO.: 22), GGTTTGTAGTTGGTTTGGAGGTTT (SEQ ID NO.: 26), GTATAGAGGGGTGTGGTGTTTTTG (SEQ ID NO.: 28), TTTGTTTTTGTTGTAGTTGTTGTTGTT (SEQ ID NO.: 29), GGGATTTTTTGTATTGGGGTAGGTT (SEQ ID NO.: 31), GGTTTTTGAGTTTGTAAGAAGTGGA (SEQ ID NO.: 37), GGTTTGAGAGATTAGTGTTTTAGATGTTTA (SEQ ID NO.: 44), GGGAGGTTGGAGTTTAGTAGTAG (SEQ ID NO.: 45), GTGAGGGTGGTTTTAAAGAGATTAG (SEQ ID NO.: 47), GAAAGGGTTTGGAAAGTTAAAAGTATTG (SEQ ID NO.: 21), TGGGAAGTTAAGGTAGGTGGATTATTT (SEQ ID NO.: 24), TTGTTTTGGGATTGTTGTTGTTTTG (SEQ ID NO.: 32), ATTGAGGAGGTTGAGGAGTGTATTG (SEQ ID NO.: 43), TTGTAGTTTTTTTAGTTAGGGTTGTTTT (SEQ ID NO.: 40), AGGGTTAGAGTAAGAGAGGGTTTTGGA (SEQ ID NO.: 12), or TTTAAGGAGGGTTGAGGGTTTTTAAG (SEQ ID NO.: 16).

In still another embodiment the at least one primer that hybridizes to a strand of said nucleic acid target gene may have the sequence ACAAAATCCAATTCCACCCCTAC (SEQ ID NO.: 62), TAATACCCCCTACTAACCCCAAAC (SEQ ID NO.: 73), ATCAAACTCAACAATTCAACCTTCC (SEQ ID NO.: 61), TCAAAACCCTCACCCTAAAAACTAAC (SEQ ID NO.: 65), CAAAAATAAAAACATTTCCCAAAATCAC (SEQ ID NO.: 71), ACCCTCCTTCCTCCCTAATTATAACC (SEQ ID NO.: 75), AAAAAATCACCAACCCTACTACCCC (SEQ ID NO.: 78), CCTTTCTTAACATTTACAATCTTCTTAAAC (SEQ ID NO.: 86), TAAACAACAACCCCAATATAACAACC (SEQ ID NO.: 89), CACTACCAACAAACCCAAACAAAC (SEQ ID NO.: 90), AGGCTAACCACTATCTCCCCTCAAAAAA (SEQ ID NO.: 96), AAACTAAAAACTCTCTCCTCCTCCC (SEQ ID NO.: 49), TCAATCTCCAATCCTTTTAAAAAAAA (SEQ ID NO.: 50), CCTTTTCCTATCACAAAAATAATCC (SEQ ID NO.: 51), AAAAAAAACCATACTTTCCCTATAACACCA (SEQ ID NO.: 52), ATCCCTACACCCAAATTTCCATTAC (SEQ ID NO.: 53), TCTACCTACAACTTCCCCAACAAC (SEQ ID NO.: 57), ACCTCTTAATCCCCTCCCTATTATACC (SEQ ID NO.: 58), CCTCCTCTCCCTAAACCCAAAATAA (SEQ ID NO.: 66), AAAAACTCCCTAACTCAACC (SEQ ID NO.: 68), AAAACAAACCAAACCCATCCACTAA (SEQ ID NO.: 81), TCTTCAATCCTTAAAAAAATACCTATTTCT (SEQ ID NO.: 87), AATTCTAAAACCTCCTCTTCCCCCT (SEQ ID NO.: 94), CCTCCAAAACTACAACTAACTCCTC (SEQ ID NO.: 59), ACTCCTAACCTCAAATAATCCACCC (SEQ ID NO.: 63), AAAACCCTCACATTTCTCCAAACAA (SEQ ID NO.: 67), TCAAAACCTAAAAACAAACAAAAAAAA (SEQ ID NO.: 82), ACCACAAAAAACAAAACCCAAAAAA (SEQ ID NO.: 83), TACCAAAAAAACCACTCTACAAACCTA (SEQ ID NO.: 84), CAATCAAATTTCCAAATCTTAATTCC (SEQ ID NO.: 54), TCACCTCCAAATCACCAAACTAATCTA (SEQ ID NO.: 55), CCCTCCAAACTATAAACCAATAAAC (SEQ ID NO.: 56), CCCAAAACATCCCCAAACTTATCTA (SEQ ID NO.: 70), ACTTCCTATAAATCCCTAACTCTCCCC (SEQ ID NO.: 74), CTATCCCAACCCTTCCCTATTAATC (SEQ ID NO.: 76), TAAAATTCCTACCTCCAACTTTCCC (SEQ ID NO.: 77), ACCAAACTCCCCAACTATCTCTCTC (SEQ ID NO.: 79), AACAACCACAACCTACTCTATCCC (SEQ ID NO.: 85), CTTTACCAAAACCAACTCTATCTCC (SEQ ID NO.: 92), AAACCAAAACCCAAAAACTAAC (SEQ ID NO.: 93), TAAATTACTACCTTAACCAAAATCC (SEQ ID NO.: 95), ATCATCAATAAACCCCATCCAAATC (SEQ ID NO.: 69), ACTCCCTCATAAAATTCTCACCAATATC (SEQ ID NO.: 72), ACCCCTTCCTCCTTAACCCTTTATC (SEQ ID NO.: 80), AAAAACCCCATAACTACAAAAAAAA (SEQ ID NO.: 91) CCAAAAATCTCTAAATACCCTTCTCC (SEQ ID NO.: 88), TTCATTTCACAACTTCAACCCCTAAA (SEQ ID NO.: 60), or CAAAAATCTAAAAACAACCCAAACTAAA (SEQ ID NO.: 64).

In yet another embodiment the primer sequence further comprises a promoter sequence. In a preferred embodiment the promoter sequence is obtained from a T7 promoter, a SP6 promoter or a T3 promoter. If the promoter is a T7 promoter it may have the sequence: 5'-CAGTAATACGACTCACTAT-AGGGAGA-3' (SEQ ID NO.: 97

In a preferred embodiment where the nucleic acid target gene region is the IGF2/H19 the primers may have the sequences: 5'-CAGTAATACGACTCACTATAGG-GAGAAGGCTGTTAGTTTTTATTTTATTTTTAA-3' (SEQ ID NO.: 99), 5'-AGGAAGAGAGAACCACTATCTCCCCT-CAAAAAA-3' (SEQ ID NO.: 100), 5'-AGGAAGAGAGGT-TAGTTTTTATTTTATTTTTAAT-3' (SEQ ID NO.: 101) or 5'-CAGTAATACGACTCACTATAGGGAGAAG-GCTAACCACTATCTCCCCTCAAAAAA-3' (SEQ ID NO.: 102).

In another aspect of the present invention a data structure of a nucleic acid target gene region for identifying an unknown phenotype of a tissue or cell that correlates with changes in the methylation state of said tissue or cell is provided comprising, a first data set providing the methylation state of at least one known phenotype of a healthy tissue or cell, a second data set providing the methylation state of said at least one known phenotype of said tissue or cell in said first data set that is diseased and a third data set providing a comparison of said first and second data sets. In addition either the first data set or the second data set of the data structure may provide the methylated/unmethylated ratio for each methylation site of a nucleic acid target gene region of said healthy tissue or cell.

In another embodiment of this aspect of the invention the third data set is a representation of said first and second data sets as a hierarchical cluster.

In other embodiments data sets comprising the characteristic methylation state of a nucleic acid, nucleic acid target gene region or gene obtained by any of the methods described herein is provided. A characteristic methylation state of a nucleic acid target region determined by spectral analysis of base-specifically cleaved amplified nucleic acid target gene region that has been treated with a reagent that modifies unmethylated cytosine to produce uracil is provided. A characteristic methylation state of a nucleic acid target gene region identified by any of the methods described herein is provided, as well as the characteristic methylation state of a nucleic acid target gene or nucleic acid target gene regions listed above identified by any of the methods described herein is provided.

In yet another aspect of the present invention a method is provided for identifying at least one CpG island region in a nucleic acid having a characteristic methylation state that correlates with an unknown phenotype of an organism, tissue or cell comprising the steps of providing a first CpG island region of the nucleic acid; identifying or discovering at least a second CpG island region within a region spanning about 5 Kb 5' of the first CpG island region and about 5 Kb 3' of the first CpG island region in the nucleic acid including the first CpG island region; and determining if at least one of the at least a second CpG island region has a characteristic methylation state that correlates with the unknown phenotype of the organism, tissue or cell.

DETAILED DESCRIPTION OF THE INVENTION

Unless defined otherwise, all technical and scientific terms used herein have the same meaning as is commonly understood by one of skill in the art to which the invention(s) belong. All patents, patent applications, published applications and publications, GENBANK sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, a "nucleic acid target gene region" is a nucleic acid molecule that is examined using the methods disclosed herein. A nucleic acid target gene region includes a segment of genomic DNA of a desired gene, a segment of mitochondrial DNA of a desired gene or RNA of a desired gene and a segment of RNA of a desired gene. In the context of methods for phenotype identification, the invention provides methods for identifying the methylation state of a nucleic acid target gene region and/or the methylation state of a nucleotide locus, a nucleic acid target gene region can also refer to an amplified product of a nucleic acid target gene region, including an amplified product of a treated nucleic acid target gene region, where the nucleotide sequence of such an amplified product reflects the methylation state of the nucleic acid target gene region. One skilled in the art would recognize that the size or length of the nucleic acid target gene region may vary depending on the limitation, or limitations, of the equipment used to perform the analysis. The nucleic acid target gene region may comprise more than one gene of interest, at least one gene of interest or a portion of a gene of interest. Correspondingly a sequential or non-sequential series of nucleic acid target gene regions may be analyzed and exploited to map an entire gene or genome. The intended target will be clear from the context or will be specified.

As used herein, a "nucleic acid target gene molecule" is a molecule comprising a nucleic acid sequence of the nucleic acid target gene region. The nucleic acid target gene molecule may contain less than 10%, less than 20%, less than 30%, less than 40%, less than 50%, greater than 50%, greater than 60%, greater than 70% greater than 80%, greater than 90% or up to 100% of the sequence of the nucleic acid target gene region.

As used herein, the "methylation state" of a nucleic acid target gene region refers to the presence or absence of one or more methylated nucleotide bases or the ratio of methylated cytosine to unmethylated cytosine for a methylation site in a nucleic acid target gene region. For example, a nucleic acid target gene region containing at least one methylated cytosine is considered methylated (i.e. the methylation state of the nucleic acid target gene region is methylated). A nucleic acid target gene region that does not contain any methylated nucleotides is considered unmethylated. Similarly, the methylation state of a nucleotide locus in a nucleic acid target gene region refers to the presence or absence of a methylated nucleotide at a particular locus in the nucleic acid target gene region. For example, the methylation state of a cytosine at the 7th nucleotide in a nucleic acid target gene region is methylated when the nucleotide present at the $7^{th}$ nucleotide in the nucleic acid target gene region is 5-methylcytosine. Similarly, the methylation state of a cytosine at the 7th nucleotide in a nucleic acid target gene region is unmethylated when the nucleotide present at the 7th nucleotide in the nucleic acid target gene region is cytosine (and not 5-methylcytosine). Correspondingly the ration of methylated cytosine to unmethylated cytosine for a methylation site or sites can provide a methylation state of a nucleic acid target gene region.

As used herein, a "characteristic methylation state" refers to a unique, or specific data set comprising the location of at least one, a portion of the total or all of the methylation sites of a nucleic acid, a nucleic acid target gene region or a gene of a sample obtained from an organism, a tissue or a cell.

As used herein, "methylation ratio" refers to the number of instances in which a molecule or locus is methylated relative to the number of instances the molecule or locus is unmethylated. Methylation ratio can be used to describe a population of individuals or a sample from a single individual. For example, a nucleotide locus having a methylation ratio of 50% is methylated in 50% of instances and unmethylated in 50% of instances. Such a ratio can be used, for example, to describe the degree to which a nucleotide locus or nucleic acid region is methylated in a population of individuals. Thus, when methylation in a first population or pool of nucleic acid molecules is different from methylation in a second population or pool of nucleic acid molecules, the methylation ratio of the first population or pool will be different from the methylation ratio of the second population or pool. Such a ratio also can be used, for example, to describe the degree to which a nucleotide locus or nucleic acid region is methylated in a single individual. For example, such a ratio can be used to describe the degree to which a nucleic acid target gene region of a group of cells from a tissue sample are methylated or unmethylated at a nucleotide locus or methylation site.

As used herein, a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring, however, for purposes herein, thymine is not considered a methylated nucleotide when present in DNA since thymine is a typical nucleotide base of DNA. Typical nucleoside bases for DNA are thymine, adenine, cytosine and guanine. Typical bases for RNA are uracil, adenine, cytosine and guanine. Correspondingly a "methylation site" is the location in the target gene nucleic acid region where methylation has, or has the possibility of occuring. For example a location containing CpG is a methylation site wherein the cytosine may or may not be methylated.

As used herein, a "methylation site" is a nucleotide within a nucleic acid, nucleic acid target gene region or gene that is susceptible to methylation either by natural occurring events in vivo or by an event instituted to chemically methylate the nucleotide in vitro.

As used herein, a "methylated nucleic acid molecule" refers to a nucleic acid molecule that contains one or more methylated nucleotides that is/are methylated.

As used herein "CpG island" refers to a G:C-rich region of genomic DNA containing a greater number of CpG dinucleotides relative to total genomic DNA. A CpG island may be about 200 base pairs in length, where the G:C content of the region is at least 50% and the ratio of observed CpG frequency over expected frequency is 0.6; typically a CpG island can be at least 500 base pairs in length, where the G:C content of the region is at least 55% and the ratio of observed CpG frequency over expected frequency is 0.65. The observed CpG frequency over expected frequency can be calculated according to the method provided in Gardiner-Garden et al., J. Mol. Biol. 196:261-281 (1987). For example, the observed CpG frequency over expected frequency could be calculated according to the formula:

$$R=(A \times B)/(C \times D)$$

where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence.

As used herein, a first nucleotide that is "complementary" to a second nucleotide refers to a first nucleotide that base-pairs, under high stringency conditions to a second nucleotide. An example of complementarity is Watson-Crick base pairing in DNA (e.g., A to T and C to G) and RNA (e.g., A to U and C to G). Thus, for example, G base-pairs, under high stringency conditions, with higher affinity to C than G base-pairs to G, A or T, and, therefore, when C is the selected nucleotide, G is a nucleotide complementary to the selected nucleotide.

As used herein, "treat", "treating" or grammatical variations thereof, refers to the process of exposing an analyte, typically a nucleic acid molecule, to conditions under which physical or chemical analyte modification or other chemical reactions (including enzymatic reactions) can occur. For example, treating a nucleic acid target gene molecule with a reagent that modifies the nucleic acid target gene molecule as a function of its methylation state may include adding a reagent such as bisulfite or an enzyme such as cytosine deaminase to a solution containing the nucleic acid target gene region. In treating the nucleic acid target gene with bisulfite any unmethylated nucleotide, such as any unmethylated C nucleotide, present in the nucleic acid target gene molecule can be chemically modified, such as deaminated; however, if the nucleic acid target gene molecule contains no unmethylated selected nucleotide, such as no unmethylated C nucleotide, then a nucleic acid target gene molecule treated with such a reagent may not be chemically modified. In another example, treating a nucleic acid target gene molecule under fragmentation or cleavage conditions can include adding a cleavage reagent such as RNase T1, such that in selected nucleic acid target gene molecules, such as nucleic acid target gene molecules containing G nucleotides, cleavage can occur. Cleavage, however, need not occur, such as with nucleic acid target gene molecules not containing G nucleotides, cleavage with RNase T1 may not occur. In another example, treating a nucleic acid target gene molecule under nucleic acid synthesis conditions can include adding a DNA or RNA polymerase and NTPs, such that nucleic acid synthesis can occur if, for example, a primer is hybridized to a nucleic acid target gene molecule, however, no nucleic acid synthesis is necessary if, for example, no primer is hybridized to a nucleic acid target gene molecule.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary.

As used herein, "specifically hybridizes" refers to preferential hybridization under nucleic acid synthesis conditions of a probe, or primer, to a nucleic acid molecule having a sequence complementary to the probe or primer compared to hybridization to a nucleic acid molecule not having a complementary sequence. For example, specific hybridization includes the hybridization of a probe to a target nucleic acid sequence that is complementary to the probe.

As used herein, "nucleotide synthesis conditions" in the context of primer hybridization refer to conditions in which a primer anneals to the nucleic acid molecule to be amplified. Exemplary nucleotide synthesis conditions are 10 mM TrisHCl pH 8.3, 1.5 mM MgCl, 50 mM KCl, 62° C. Other exemplary nucleotide synthesis conditions are 16.6 mM ammonium sulfate, 67 mM Tris pH 8.8, 6.7 mM MgCl, 10 mM 2-mercaptoethanol, 60° C. Those of skill in the art are familiar with parameters that affect hybridization; such as temperature, probe or primer length and composition, buffer composition and pH, and salt concentration can readily adjust these parameters to achieve specific hybridization of a nucleic acid to a target sequence.

As used herein, "complementary base pairs" refer to Watson-Crick base pairs (e.g., G to C and A to T in DNA and G to C and A to U in RNA) or the equivalent thereof when non-natural or atypical nucleotides are used. Two nucleic acid strands that are complementary contain complementary base pairing. A probe is not complementary when mismatches such as G-T, G-A, C-T or C-A arise when a probe or primer hybridizes to a nucleic acid target gene molecule.

As used herein "substantially complementary" refers to primers that are sufficiently complementary to hybridize with nucleic acid target gene molecules having a desired sequence under nucleic acid synthesis conditions. Primers should have sufficient complementarity to hybridize to a desired nucleic acid target gene molecule and permit amplification of the nucleic acid target gene molecule. For example, a primer used in the methods disclosed herein can be 100% complementary with the nucleic acid target gene molecule desired to be amplified. In another example, a primer can have 1, 2, 3, or more mismatches, provided that the primer can be used to amplify at least one nucleic acid target gene molecule desired to be amplified. For example, a nucleic acid target gene molecule can have three cytosine nucleotides in the region with which a primer hybridizes; when only one of the three C nucleotides are methylated, treatment with bisulfite can convert the two unmethylated C nucleotides to U nucleotides, and a primer 100% complementary to a nucleic acid target gene molecule having three C nucleotides can still hybridize to a nucleic acid target gene molecule having only one C nucleotide, such that the nucleic acid target gene molecule having only one C nucleotide can still be amplified.

As used herein "nucleic acid" refers to polynucleotides such as deoxyribonucleic acid (DNA) and ribonucleic acid (RNA). The term also includes, as equivalents, derivatives, variants and analogs of either RNA or DNA made from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil.

As used herein, "mass spectrometry" encompasses any suitable mass spectrometric format known to those of skill in the art. Such formats include, but are not limited to, Matrix-Assisted Laser Desorption/Ionization, Time-of-Flight (MALDI-TOF), Electrospray (ES), IR-MALDI (see, e.g., published International PCT application No. 99/57318 and U.S. Pat. No. 5,118,937), Ion Cyclotron Resonance (ICR), Fourier Transform and combinations thereof.

As used herein, the phrase "mass spectrometric analysis" refers to the determination of the mass to charge ratio of atoms, molecules or molecule fragments.

As used herein, a "reference nucleic acid molecule" refers to a nucleic acid molecule known to be methylated or unmethylated, or a nucleic acid molecule in which the methylation state of one or more nucleotide loci of the nucleic acid molecule is known. A reference nucleic acid can be used to calculate or experimentally derive reference masses. A reference nucleic acid used to calculate reference masses is typically a nucleic acid containing a known sequence with known methylated nucleotide loci. A reference nucleic acid used to experimentally derive reference masses can have, but is not required to have, a known sequence or known methylated nucleotide loci; methods such as those disclosed herein or otherwise known in the art can be used to identify a reference nucleic acid as methylated even when the reference nucleic acid does not have a known sequence.

As used herein, a "correlation" between a nucleic acid target gene molecule and a reference, including a "correlation" between a nucleotide locus in a nucleic acid target gene molecule and a nucleotide locus in a reference, refers to a similarity or identity of the methylation state of a nucleic acid target gene molecule or nucleotide locus to that of a reference, such that the nucleic acid target gene molecule and the reference are expected to have at least one undefined locus with the same methylation state. For example, when the methylation state of fewer than all nucleotide loci of a nucleic acid target gene molecule have been identified, and when there is a correlation between a reference nucleic acid and a nucleic acid target gene, one or more of the unidentified loci of the nucleic acid target gene molecule can be expected to have the same methylation state as the corresponding nucleotide locus in the reference.

As used herein, the term "correlates" as between a specific phenotype of a sample and the changes in methylation state of a nucleic acid target gene region refers to an identifiable connection between a particular phenotype of a sample and its methylation state.

As used herein, "nucleic acid synthesis" refers to a chemical or biochemical reaction in which a phosphodiester bond is formed between one nucleotide and a second nucleotide or an oligonucleotide. Nucleic acid synthesis can include enzymatic reactions such as DNA replication reactions such as PCR or transcription, or chemical reactions such as solid phase synthesis. Nucleic acid synthesis conditions refers to conditions of a nucleic acid molecule-containing solution in which nucleotide phosphodiester bond formation is possible. For example, a nucleic acid target gene molecule can be contacted with a primer, and can be treated under nucleic acid synthesis reactions, which can include, for example, PCR or transcription conditions, and, when the primer hybridizes to the nucleic acid target gene molecule, nucleotides can be synthesized onto the primer, that is, nucleotides can be enzymatically added via phosphodiester linkage to the 3' end of primer, however, when no primer is hybridized to the nucleic acid target gene molecule, it is possible that no nucleotides are synthesized onto the primer.

As used herein, "amplifying" refers to increasing the amount of a nucleic acid molecule or a number of nucleic acid molecules. Amplification may be performed by one or more cycles of polymerase chain reaction (PCR). Based on the 5' and 3' primers that are chosen the region or regions of the nucleic acid molecule or nucleic acid molecules to be amplified may be selected. Amplification can be by any means known to those skilled in the art, including use of the PCR, transcription, and other such methods.

As used herein, "specifically amplifying" refers to increasing the amount of a particular nucleic acid molecule based on one or more properties of the molecule. For example, a nucleic acid molecule can be specifically amplified using specific hybridization of one or more primers to one or more regions of the nucleic acid molecule in PCR. Typically, specifically amplifying includes nucleic acid synthesis of a nucleic acid target gene molecule where a primer hybridizes with complete complementarity to a nucleotide sequence in the nucleic acid target gene molecule.

As used herein a "primer" is a polynucleotide such as DNA or RNA that because of its specific nucleotide sequence is able to hybridize to a template nucleic acid, whereupon an enzyme can catalyze addition of one or more nucleotides to the 3' hydroxyl group of the primer thorough formation of a phosphoester or phosphodiester bond in a nucleotide synethesis reaction such as transcription or DNA replication.

As used herein, a "methylation specific primer" or "methylation state specific primer" refers to a primer that can specifically hybridize with a nucleic acid target gene region or a methylation-specific reagent-treated nucleic acid target gene molecule in accordance with the methylation state of the nucleic acid target gene molecule. For example, a nucleic acid target gene molecule can be treated with a methylation-specific reagent, resulting in a change in the nucleotide sequence of the nucleic acid target gene molecule as a function of the methylation state of the nucleic acid target gene molecule; and a methylation state specific primer can specifically hybridize to the treated methylated nucleic acid target gene molecule, without hybridizing to a treated unmethylated nucleic acid target gene molecule or without hybridizing to a treated, differently methylated nucleic acid target gene molecule. In another example, a nucleic acid target gene molecule can be treated with a methylation-specific reagent, resulting in a change in the nucleotide sequence of the nucleic acid target gene molecule as a function of the methylation state of the nucleic acid target gene molecule and a methylation state specific primer can specifically hybridize to the treated unmethylated nucleic acid target gene molecule, without hybridizing to a treated methylated nucleic acid target gene molecule or without hybridizing to a treated, differently unmethylated nucleic acid target gene molecule. Methylation specific primers that hybridize to a nucleic acid target gene molecule then can serve as primers for subsequent nucleotide synthesis reactions, such as PCR.

As used herein, an "amplified product" or "amplified nucleic acid" is any product of a nucleotide synthesis reaction using a nucleic acid target gene molecule as the template. Thus, a single-stranded nucleic acid molecule complementary to the treated nucleic acid target gene molecule and formed in the first amplification step is an amplified product. In addition, products of subsequent nucleotide synthesis reactions, which contain the same sequence as the treated nucleic acid target gene molecule, or the complement thereof, are amplification products. An amplification product can be a single-stranded nucleic acid molecule or a double-stranded nucleic acid molecule.

As used herein, "fragmentation" or "cleavage" refers to a procedure or conditions in which a nucleic acid molecule, such as a nucleic acid target gene molecule or amplified product thereof, is severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid target gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid target gene molecule or the portion of an amplified product thereof containing the corresponding nucleotide sequence of a nucleic acid target gene molecule. For example, it is within the scope of the present methods, compounds and compositions, that an amplified product can contain one or more nucleotides more than the amplified nucleotide region of the nucleic acid target gene sequence (e.g., a primer can contain "extra" nucleotides such as a transcriptional initiation sequence, in addition to nucleotides complementary to a nucleic acid target gene molecule, resulting in an amplified product containing "extra" nucleotides or nucleotides not corresponding to the amplified nucleotide region of the nucleic acid target gene molecule). In such an example, the fragments or cleaved products corresponding to the nucleotides not arising from the nucleic acid target gene molecule will typically not provide any information regarding methylation in the nucleic acid target gene molecule. One skilled in the art can therefore understand that the fragments of an amplified product used to provide methylation information in the methods provided herein are fragments containing one or more nucleotides arising from the nucleic acid target gene molecule, and not fragments containing nucleotides arising solely from a sequence other than that in the nucleic acid target gene molecule. Accordingly, one skilled in the art will understand the fragments arising from methods, compounds and compositions provided herein to include fragments arising from portions of amplified nucleic acid molecules containing, at least in part, nucleotide sequence information from or based on the representative nucleic acid target gene molecule.

As used herein, "base specific cleavage" refers to selective cleavage of a nucleic acid at the site of a particular base (e.g., A, C, U or G in RNA or A, C, T or G in DNA) or of a particular base type (e.g., purine or pyrimidine). For example, C-specific cleavage refers to cleavage of a nucleic acid at every C nucleotide in the nucleic acid.

As used herein, the phrase "non-specifically cleaved", in the context of nucleic acid cleavage, refers to the cleavage of nucleic acid target gene molecule at random locations throughout, such that various cleaved fragments of different size and nucleotide sequence content are randomly generated. Cleavage at random locations, as used herein, does not require absolute mathematical randomness, but instead only a lack of sequence-based preference in cleavage. For example, cleavage by irradiative or shearing means can cleave DNA at nearly any position, however, such methods can result in cleavage at some locations with slightly more frequency than other locations. Nevertheless, cleavage at nearly all positions with only a slight sequence preference is still random for purposes herein. Non-specific cleavage using the methods described herein can result in the generation of overlapping nucleotide fragments.

As used herein, the phrase "statistically range in size" refers to the size range for a majority of the fragments generated using cleavage methods known in the art or disclosed herein, such that some of the fragments can be substantially smaller or larger than most of the other fragments within the particular size range. An example of such a statistical range in sizes of fragments is a Poisson distribution. For example, the statistical size range of 12-30 bases also can include some oligonucleotides as small as 1 nucleotide or as large as 300 nucleotides or more, but these particular sizes statistically occur relatively rarely. In some embodiments, there is no limit to the statistical range of fragments. In other embodiments, a statistical range of fragments can specify a range such that 10% of the fragments are within the specified size range, where 20% of the fragments are within the specified size range, where 30% of the fragments are within the specified size range, where 40% of the fragments are within the specified size range, where 50% of the fragments are within the specified size range, where 60% or more of the fragments are within the specified size range, where 70% or more of the fragments are within the specified size range, where 80% or more of the fragments are within the specified size range, where 90% or more of the fragments are within the specified size range, or where 95% or more of the fragments are within the specified size range.

As used herein, the phrase "set of mass signals" or a "mass peak pattern" refers to two or more mass determinations made for each of two or more nucleic acid fragments of a nucleic acid molecule. A "mass pattern" refers to two or more masses corresponding to two or more nucleic acid fragments of a nucleic acid molecule.

As used herein, a "subject" includes, but is not limited to, an animal, plant, bacterium, virus, parasite and any other organism or entity that has nucleic acid. Among animal subjects are mammals, including primates, such as humans.

As used herein, "normal", when referring to a nucleic acid molecule or sample source, such as an individual or group of individuals, refers to a nucleic acid molecule or sample source that was not selected according to any particular criterion, and generally refers to a typical nucleotide sequence of a nucleic acid molecule or health condition of a sample source (e.g., one or more healthy subjects or one or more subjects that do not a disease). For example, a normal methylation state of a particular nucleotide locus can be the wild type methylation state of the nucleotide locus. In another example, a group of normal subjects can be a group of subjects not having a particular phenotype (such as a disease).

As used herein, a "phenotype" refers to a set of parameters that includes any distinguishable trait of an organism. A phenotype can be physical traits and/or mental traits, such as emotional traits.

As used herein, a "methylation" or "methylation state" correlated with a disease, disease outcome or outcome of a treatment regimen refers to a methylation state of a nucleic acid target gene region or nucleotide locus that is present or absent more frequently in subjects with a known disease, disease outcome or outcome of a treatment regimen, relative to the methylation state of a nucleic acid target gene region or nucleotide locus than otherwise occur in a larger population of individuals (e.g., a population of all individuals).

As used herein, a "data processing routine" refers to a process, that can be embodied in software, that determines the biological significance of acquired data (i.e., the ultimate results of an assay or analysis). For example, the data processing routine can make a genotype determination based upon the data collected. In the systems and methods herein, the data processing routine also can control the instrument and/or the data collection routine based upon the results determined. The data processing routine and the data collection routines can be integrated and provide feedback to operate the data acquisition by the instrument, and hence provide assay-based judging methods.

As used herein, a "plurality of genes" or a "plurality of nucleic acid target gene molecules" includes at least two, five, 10, 25, 50, 100, 250, 500, 1000, 2,500, 5,000, 10,000, 100,000, 1,000,000 or more genes or nucleic acid target gene molecules. A plurality of genes or nucleic acid target gene molecules can include complete or partial genomes of an organism or even a plurality thereof. Selecting the organism type determines the genome from among which the gene or nucleic acid target gene molecules are selected.

As used herein, "sample" refers to a composition containing a material to be detected. Samples include "biological samples", which refer to any material obtained from a living source, for example, an animal such as a human or other mammal, a plant, a bacterium, a fungus, a protist or a virus or a processed form, such as amplified or isolated material. The biological sample can be in any form, including a solid material such as a tissue, cells, a cell pellet, a cell extract, a biopsy, or feces, or a biological fluid such as urine, whole blood, plasma, serum, interstitial fluid, peritoneal fluid, lymph fluid, ascites, sweat, saliva, follicular fluid, breast milk, non-milk breast secretions, cerebral spinal fluid, seminal fluid, lung sputum, amniotic fluid, exudate from a region of infection or inflammation, a mouth wash containing buccal cells, synovial fluid, or any other fluid sample produced by the subject. In addition, the sample can be solid samples of tissues or organs, such as collected tissues, including bone marrow, epithelium, stomach, prostate, kidney, bladder, breast, colon, lung, pancreas, endometrium, neuron, muscle, and other tissues. Samples can include organs, and pathological samples such as a formalin-fixed sample embedded in paraffin. If desired, solid materials can be mixed with a fluid or purified or amplified or otherwise treated. Samples examined using the methods described herein can be treated in one or more purification steps in order to increase the purity of the desired cells or nucleic acid in the sample, Samples also can be examined using the methods described herein without any purification steps to increase the purity of desired cells or nucleic acid. In particular, herein, the samples include a mixture of matrix used for mass spectrometric analyses and a biopolymer, such as a nucleic acid.

As used herein, "array" refers to a collection of elements, such as nucleic acids. Typically an array contains three or more members. An addressable array is one in which the members of the array are identifiable, typically by position on a solid support. Hence, in general the members of the array will be immobilized to discrete identifiable loci on the surface of a solid phase. Arrays include a collection on elements on a single solid phase surface, such as a collection of nucleotides on a chip.

As use herein, the term "data set" refers to numerical values obtained from the analysis, such as by mass spectral analysis of the nucleic acid target gene region. These numerical values associated with analysis may be values such as peak height, area under the curve and molecular mass for example in the case of mass spectral analysis.

As used herein the term "data structure" refers to a combination of two or more data sets, applying one or more mathematical manipulations to one or more data sets to obtain one or more new data sets, or manipulating two or more data sets into a form that provides a visual illustration of the data in a new way. An example of a data structure prepared from manipulation of two or more data sets would be a hierarchical cluster.

The present invention provides a method for identifying an unknown phenotype of a tissue or cell that correlates with changes in the methylation state of the tissue or cell comprising; treating a nucleic acid sample from said tissue or cell with a reagent that modifies unmethylated cytosine to produce uracil; amplifying a nucleic acid target gene region using at least one primer that hybridizes to a strand of the nucleic acid target gene region producing amplified nucleic acids; determining the characteristic methylation state of the nucleic acid target gene region by base specific cleavage and identification of methylation sites of the amplified nucleic acids; and comparing the ratio of methylated cytosine to unmethylated cytosine for each of the methylation sites of the characteristic methylation state of the sample from the tissue or cell nucleic acid to the ratio of methylated cytosine to unmethylated cytosine for each of the methylation sites of a tissue or cell nucleic acid sample of the same type having a known phenotype thereby identifying the unknown phenotype.

In one preferred aspect of the present invention analysis of the DNA methylation of a nucleic acid target gene region is obtained by MALDI-TOF MS analysis of base-specific cleavage products derived from amplified nucleic acid target gene molecules. In general, a PCR amplification product is generated from bisulfite treated DNA, which is transcribed in vitro into a single stranded RNA molecule and subsequently cleaved base-specifically by an endoribonuclease. The conversion of cytosine to uracil during bisulfite treatment generates different base specific cleavage patterns that can be readily analysed by MALDI-TOF MS. These spectral analyses may be used to determine the ratio of methylated versus non-methylated nucleotide at each methylation site of the nucleic acid target gene region. One skilled in the art will recognise that the methylation state of any nucleic acid, nucleic acid target gene region or gene of interest may be determined using the methods of the present invention. In addition, one skilled in the art would recognise the importance of the location of CpG islands in identifying novel, unique or specific methylation states for diagnostic purposes. Correspondingly, the location of a CpG island in a nucleic acid of interest may indicate other CpG islands of significance located in and around, or in close proximity to, the initially identified CpG island. Consequently it would be reasonable that one skilled in the art would look to other areas in proximity to initially identified CpG island to locate other CpG islands of interest.

Identifying Nucleic Acid Target Gene Regions

Selecting nucleic acid target gene regions of interest that harbor potential methylated sites may be based on a variety of characteristics known or available to those skilled in the art regarding the target gene of interest. Selection criteria may include for example the gene's physiological role or function in a biological pathway related to the disease/phenotype of interest, existence of mutations effecting disease/phenotype or sequence polymorphisms conferring predisposition to disease/phenotype of interest. Selection may also be based on known expression status or sequence motifs binding specific proteins relevant to methylation of gene regions/chromosomal regions. One skilled in the art would recognize that a considerable amount of information may be obtained through publication of data and experiments that may provide key indications that the methylation state of a particular gene may be of importance for future diagnostic purposes that are the subject of the present invention.

Any type of disease condition that can be correlated with changes in the methylation state of a sample organism, tissue or cell can be analyzed with the methods of the present invention, some of these disease conditions include for example, cancer, cardiovascular disease (CVD), central nervous system disease (CNS), metabolic disease, aging, morbidity, osteoarthritis, infection and drug response. Of particular interest are cancer related diseases and include for example, lung cancer, breast cancer, prostate cancer, colon cancer, liver cancer, cancer of the central nervous system and thyroid cancer.

Metabolic disease such as type II diabetes has been regarded as a relatively distinct disease entity, but type II diabetes is often a manifestation of a much broader underlying disorder (Zimmet et al. *Nature* 414:782-787 (2001)), which may include metabolic syndrome (syndrome X), diabetes (e.g., type I diabetes, type II diabetes, gestational diabetes, autoimmune diabetes), hyperinsulinemia, hyperglycemia, impaired glucose tolerance (IGT), hypoglycemia, B-cell failure, insulin resistance, dyslipidemias, atheroma, insulinoma, hypertension, hypercoagulability, microalbuminuria, and obesity. Because of these manifestations diabetes is of particular interest.

Any nucleic acid, nucleic acid target gene region or gene may be have a potentially significant characteristic methylation state for diagnostic purposes. Consequently, any nucleic acid of interest may be analyzed using the method described herein, some examples of particular genes of interest include, CADHERIN13, DAPK1, MGMT, CDKN2A, RASSF1, FOSB, ZFP36, GPC3, CACNA2, TACSTD, FGG CpG1, GAGEB1, MGP, MAGEA3, SELENBP1, MAGEA1, MAGEE1, SDK2, MAGEA4, ADAMTS, ABCC11, IGSF4, CEACAM6, RODH, PRAME, STEAP, GAGED2, CAV1, IGF2R, SERPINB5, PLAU, S100A2, SCGB3A1, EDNRB I2, CLIC3, Page-5, PBP, TNA, GJB2, WIF-1, AQP-1, CDH5, CDH3, CLIC5, ROHDBT2, ESAM and JUP. Each gene may have particular regions of interest selected by a variety of methods including for example the presence of CpG islands. Particular regions of interest in the above listed genes include for example the following genome locations, chr16: 82397485-82400484, chr9:83666822-83667821, chr10: 131194125-131195124, chr9:21964618-21966117, chr3: 50228037-50233099, chr19:50645115-50648489, chr19: 44572554-44573553, chrX:131064581-131065580, chr3: 50314945-50476944, chr2:47552926-47554425, chr4: 155933296-156048654, chrX:48140000-48350000, chr12: 14559868-15319242, chrX:149686099-149687598, chr1: 148082308-148159211, chrX:149994325-150102324, chrX:137726468-140726467, chr17:71816325-71902844, chrX:148774790-148904569, chr11:130330360-130335359, chr16:48015318-48016317, chr11:115408779-115410278, chr19:46710046-47160045, chr12:56859865-56886864, chr22:21225987-21227486, chr7:89380761-89382260, chrX:51057294-51590627, chr7:115704514-115706013, chr6:160222309-160223808, chr18:60861193-60996192, chr10:75562090-75563589, chr1:150353913-150383912, chr5:180082544-180084043, chr13:77351803-77621802, chr9:133327587-133337586, chrX:53684992-54018324, chr12:118355527-118357026, chr3:44796503-44976502, chr13:19689358-19699482, chr12:65231587-65233086, chr7:30456743-30861742, chr16:66026768-66269767, chr16:68413396-68414895, chr6:45983175-45986466, chr8:22676411-22677910, chr11:124654685-124668369 and chr17:39851715-39852714.

Sample

The methods described herein can be applied to samples that contain nucleic acids, preferably a nucleic acid target gene region of interest, from any of a variety of sources, for any of a variety of purposes. Typically the methods used herein are used to determine information regarding a subject, or to determine a relationship between nucleic acid methylation and disease. The samples used in the methods described herein will be selected according to the purpose of the method to be applied. For example, samples can contain nucleic acid from a plurality of different organisms when a phenotype of the organisms is to be correlated with the presence or absence of a methylated nucleic acid molecule or nucleotide locus. In another example, samples can contain nucleic acid from one individual, where the sample is examined to determine the disease state or tendency toward disease of the individual. One skilled in the art can use the methods described herein to determine the desired sample to be examined.

A sample may be from any subject, including for example, animal, plant, bacterium, fungus, virus or parasite. Animal may include for example mammals, birds, reptiles, amphibians or fish. Preferably subject mammals are humans. A sample from a subject can be in any form that provides a desired nucleic acid to be analyzed, including a solid material such as a tissue, cells, a cell pellet, a cell extract, feces, or a biopsy, or a biological fluid such as urine, whole blood, serum, plasma, interstitial fluid, peritoneal fluid, lymph fluids, ascites, sweat, saliva, follicular fluid, breast milk, non-milk breast secretions, cerebral spinal fluid, seminal fluid, lung sputum, amniotic fluid, exudate from a region of infection or inflammation, a mouth wash containing buccal cells, synovial fluid, or any other fluid sample produced by the subject. In addition, the sample can be collected tissues, including bone marrow, epithelium, stomach, prostate, kidney, bladder, breast, colon, lung, pancreas, endometrium, neuron, and muscle. Samples can include tissues, organs, and pathological samples such as a formalin-fixed sample embedded in paraffin.

As one of skill in the art will recognize, some samples may be used directly in the methods provided herein. For example, samples can be examined using the methods described herein without any purification or manipulation steps to increase the purity of desired cells or nucleic acid molecules.

If desired, a sample may be prepared using known techniques, such as that described by Maniatis, et al. (*Molecular Cloning: A Laboratory Manual*, Cold Spring Harbor, N.Y., pp. 280-281 (1982)). For example, samples examined using the methods described herein can be treated in one or more purification steps in order to increase the purity of the desired cells or nucleic acid in the sample. If desired, solid materials may be mixed with a fluid.

Methods for isolating nucleic acid in a sample from essentially any organism or tissue or organ in the body, as well as from cultured cells are well known. For example, the sample can be treated to homogenize an organ, tissue or cell sample, and the cells may be lysed using known lysis buffers, sonication, electroporation and combinations thereof. Further purification can be performed as needed, as will be appreciated by those skilled in the art. In addition, sample preparation may include a variety of reagents, which can be included in subsequent steps. These include reagents such as salts, buffers, neutral proteins (e.g., albumin), detergents, and such reagents, which can be used to facilitate optimal hybridization or enzymatic reactions, and/or reduce non-specific or background interactions. Also, reagents that otherwise improve the efficiency of the assay, such as, for example, protease inhibitors, nuclease inhibitors and anti-microbial agents, can be used, depending on the sample preparation methods and purity of the nucleic acid target gene molecule.

Nucleic Acid Target Gene Molecule

The methods provided herein are used to determine methylation states, including whether a nucleic acid target gene molecule contains a methylated or unmethylated nucleotide and determination of methylation ratios (methylated versus unmethylated) for one or more methylation sites or groups of methylation sites. Thus, nucleic acid target gene molecules used in the methods provided herein include any nucleic acid molecule. One or more methods provided herein may be practiced to provide information regarding methylated nucleotides in the nucleic acid target gene molecule.

The methods provided herein permit any nucleic acid-containing sample or specimen, in purified or non-purified form, to be used. Thus, the process may employ for example, DNA or RNA, including messenger RNA, wherein DNA or RNA can be single stranded or double stranded.

The specific nucleic acid sequence to be examined, (i.e., the nucleic acid target gene molecule), may be a fraction of a larger molecule or may be present initially as a discrete molecule, so that the specific nucleic acid target gene molecule constitutes the entire nucleic acid component of a sample, It is not necessary that the nucleic acid target gene molecule to be examined be present initially in a pure form; it may be a minor fraction of a complex mixture, such as contained in whole organism DNA. The nucleic acid target gene molecule for which methylation status is to be determined may be an isolated molecule or part of a mixture of nucleic acid molecules.

The nucleic acid target gene molecule to be analyzed may include one or more protein-encoding regions of genomic DNA or a portion thereof. The nucleic acid target gene molecule can contain one or more gene promoter regions, one or more CpG islands, one or more sequences related to chromatin structure, or other regions of cellular nucleic acid. The nucleic acid target gene molecule can be methylated or unmethylated at individual nucleotides, such as cytosines; at small groups of nucleotides, such as cytosine-rich sequences, or at one or more CpG islands.

The length of the nucleic acid target gene molecule that may be used in the current methods may vary according to the sequence of the nucleic acid target gene molecule, the particular methods used for methylation identification, and the particular methylation state identification desired, but will typically be limited to a length at which fragmentation and detection methods disclosed herein can be used to identify the methylation state of one or more nucleotide loci of the nucleic acid target gene molecule.

In one embodiment, the nucleic acid target gene molecule is of a length in which the methylation state of two or more nucleotide loci can be identified. For example, a nucleic acid target gene molecule may be at least about 20, 25, 30, 35, 40, 50, 60, 70, 80, 90, 100, 120, 140, 160, 180, 200, 225, 250, 275, 300, 350, 400, 450, 500, 550, 600, 700, 800, 900, 1000, 1200, 1400, 1600, 1800, 2000, 2500 or 3000 bases in length. Typically, a nucleic acid target gene molecule will be no longer than about 10,000, 5000, 4000, 3000, 2500, 2000, 1500, 1000, 900, 800, 700, 600, 500, 450, 400, 350, 280, 260, 240, 220, 200, 190, 180, 170, 160, 150, 140, 130, 120, 110 or 100 bases in length.

A nucleic acid target gene molecule examined using the methods disclosed herein may contain one or more methylated nucleotides, but is not required to contain any methylated nucleotides. The methods disclosed herein may be used to identify whether or not a nucleic acid target gene molecule contains methylated or unmethylated nucleotides, to identify the nucleotide locus of a methylated or unmethylated nucleotide in the nucleic acid target gene molecule and to determine the ratio of methylated versus unmethylated nucleotides at one or more methylation sites.

A nucleotide that has been identified as methylated in genomic DNA is cytosine. Methylated cytosines can be present in any of a variety of regions of genomic DNA. The methods provided herein may be used to determine the methylation state of a cytosine in any of a variety of genomic DNA regions. For example, methylcytosine is commonly found in cytosine-guanine dinucleotides termed "CpG" dinucleotides. In one embodiment, the methylation state of a cytosine nucleotide in one or more CpG dinucleotides in the nucleic acid target gene molecule is identified. Such dinucleotides are enriched in some regions of the genome, where these enriched regions are termed CpG islands. CpG islands may be found near promoter regions for some genes, including promoter regions for tumor suppressor genes, oncogenes, developmental regulatory genes, and housekeeping genes. Thus, the methods disclosed herein can be used to identify whether a cytosine in a CpG dinucleotide in a nucleic acid target gene molecule is methylated where the CpG nucleotide is located in a gene promoter region, such as a tumor suppressor gene, oncogene, developmental regulatory gene, or housekeeping gene promoter region. The methods disclosed herein also may be used to identify whether a one or more cytosines in a CpG island in a nucleic acid target gene molecule are methylated.

The methods provided herein may be used to identify the methylation of a plurality of nucleotide loci. Accordingly, methylation of one or more, up to all, nucleotide loci of a large nucleic acid target gene region may be identified using the methods provided herein. For example, the methylation state of a plurality of nucleotide loci, up to all nucleotide loci of an entire CpG island may be identified using the methods provided herein.

Nucleic acid molecules can contain nucleotides with modifications, such as methylation, that do not change the nucleotide sequence of the nucleic acid molecule. Amplification of a nucleic acid molecule containing such a modified nucleotide can result in an amplified product complementary to the unmodified nucleotide, resulting in the amplified product not containing the information regarding the nucleotide modification. For example, the amplified product of a nucleic acid molecule containing a methylated cytosine will result in an amplified product containing either an unmodified guanine (for the complementary strand) or an unmodified cytosine at the location of the methylated cytosine. Reagents are known that can modify the nucleotide sequence of a nucleic acid target gene molecule according to the presence or absence of modifications in one or more nucleotides, where the modification itself does not change the nucleotide sequence. For example, bisulfite may be used in a process to convert unmethylated cytosine into uracil, thus resulting in a modification of the nucleotide sequence of a nucleic acid target gene molecule according to the presence of unmethylated cytosines in the nucleic acid target gene molecule.

In performing the methods disclosed herein, the nucleic acid target gene molecule is treated with a reagent that can modify the nucleic acid target gene molecule as a function of its methylation state. The treated nucleic acid target gene molecule can have a resulting sequence that reflects the methylation state of the untreated nucleic acid target gene molecule. In one embodiment, the reagent can be used to modify an unmethylated selected nucleotide to produce a different nucleotide. For example, the reagent may be used to modify unmethylated cytosine to produce uracil.

Reagents for Sequence Modification

A method for determining the methylation state of a nucleic acid molecule or nucleotide locus includes contacting a nucleic acid target gene molecule-containing sample with a reagent that can modify the nucleic acid target gene molecule nucleotide sequence as a function of its methylation state. A variety of reagents for modifying the nucleotide sequence of nucleic acid molecules are known in the art and can be used in conjunction with the methods provided herein. For example, a nucleic acid target gene molecule can be contacted with a reagent that modifies unmethylated bases but not methylated bases, such as unmethylated cytosines but not methylated cytosines, in such a manner that the nucleotide sequence of the nucleic acid target gene molecule is modified at the location of an unmethylated base but not at the location of the methylated base, such as at the location of an unmethylated cytosine but not at the location of a methylated cytosine. An exemplary reagent that modifies unmethylated bases but not methylated bases is sodium bisulfite, which modifies unmethylated cytosines but not methylated cytosines.

Methods for modifying a nucleic acid target gene molecule in a manner that reflects the methylation pattern of the nucleic acid target gene molecule are known in the art, as exemplified in U.S. Pat. No. 5,786,146 and U.S. patent publications 20030180779 and 20030082600.

In one embodiment, the reagent can be used to modify unmethylated cytosine to uracil. An exemplary reagent used for modifying unmethylated cytosine to uracil is sodium bisulfite. Sodium bisulfite (NaHSO) reacts with the 5,6-double bond of cytosine to form a sulfonated cytosine reaction intermediate which is susceptible to deamination, giving rise to a sulfonated uracil. The sulfonate group of the sulfonated uracil can be removed under alkaline conditions, resulting in the formation of uracil. Uracil is recognized as a thymine by DNA polymerase enzymes such as Taq polymerase, and, therefore, upon amplification of the nucleic acid target gene molecule using methods such as PCR, the resultant amplified nucleic acid target gene molecule contains thymine at positions where unmethylated cytosine occurs in the starting template nucleic acid target gene molecule, and the complementary strand contains adenine at positions complementary to positions where unmethylated cytosine occurs in the starting nucleic acid target gene molecule. Further, amplification methods such as PCR can yield an amplified nucleic acid target gene molecule containing cytosine where the starting nucleic acid target gene molecule contains 5-methylcytosine, and the complementary strand maintains guanine at positions complementary to positions where methylated cytosine occurs in the starting nucleic acid target gene molecule. Thus, in amplification methods such as PCR, cytosine in the amplified product can mark the location of 5-methylcytosine, and thymine in the amplified product can mark the location of unmethylated cytosine. Similarly, in the amplified product strands complementary to the treated nucleic acid target gene molecule, guanine can mark the location of 5-methylcytosine and adenine can mark the location of unmethylated cytosine.

Exemplary methods for bisulfite treatment of target DNA can include contacting denatured DNA with a bisulfite solution that also may contain urea and hydroquinone, and incubating the mix for 30 seconds at 95° C. and 15 minutes at 55° C., for 20 cycles. In one alternative method, the bisulfite treatment may be performed in agarose, and precipitation steps may be replaced with dialysis steps (U.S. Pat. No. 6,214,556 and Olek et al., *Nucl. Acids Res.* 24:5064-66 (1996)). Variations of bisulfite treatment of a nucleic acid target gene molecule are known in the art as exemplified in U.S. Pats. Nos. 5,786,146 and 6,214,556, U.S. patent publication 20030082600, Tost et al., *Nucl. Acids Res.* 37:e50 (2003), Olek et al., *Nucl. Acids Res.* 24:5064-66 (1996), and Grunau et al., *Nucl. Acids Res.* 29:e65 (2001).

In the methods provided herein, a methylation-specific reagent-treated nucleic acid target gene molecule can have a different nucleotide sequence compared to the nucleotide sequence of the nucleic acid target gene molecule prior to treatment. Since the methylation-specific reagent modifies the nucleotide sequence of a nucleic acid target gene molecule as a function of the methylation state of the nucleic acid target gene molecule, the treated nucleic acid target gene molecule will have a nucleotide sequence related to the nucleotide sequence of the untreated nucleic acid target gene molecule, which reflects the methylation state of the untreated nucleic acid target gene molecule.

Amplification of Treated Nucleic Acid Target Gene Molecule

The methods provided herein also may include a step of amplifying the treated nucleic acid target gene molecule using one or more primers. In one embodiment, at least one primer is a methylation specific primer. In another embodiment, the primer contains one or more nucleotides complementary to the nucleotide treated using the methylation-specific reagent. For example, bisulfite is cytosine specific; when bisulfite is used, a primer used in a method of identifying methylated nucleotides can contain one or more guanine nucleotides. The amplification methods can serve to selectively amplify nucleic acid target gene molecules complementary to the primers while not amplifying one or more other nucleic acid molecules in a nucleic acid sample.

Methylation-specific primers, which are also referred to herein as methylation state specific primers, are designed to distinguish between nucleotide sequences of treated nucleic acid target gene molecules based on the methylation state of one or more nucleotides in the untreated nucleic acid target gene molecule. For example, methylation specific primers may be designed to hybridize to a nucleotide sequence of a reagent-treated nucleic acid target gene molecule arising from a nucleic acid target gene molecule that contained methylated nucleotides in preference to hybridizing to a nucleotide sequence of a reagent-treated nucleic acid target gene molecule arising from a nucleic acid target gene molecule that contained unmethylated nucleotides. Correspondingly, methylation specific primers may be designed to hybridize to a nucleotide sequence of a reagent-treated nucleic acid target gene molecule arising from a nucleic acid target gene molecule that contained unmethylated nucleotides in preference to hybridizing to a nucleotide sequence of a reagent-treated nucleic acid target gene molecule arising from a nucleic acid target gene molecule that contained methylated nucleotides.

The primers used for amplification of the treated nucleic acid target gene molecule in the sample can hybridize to the treated nucleic acid target gene molecule under conditions in which a nucleotide synthesis reaction, such as PCR, can occur. Typically, two or more nucleotide synthesis reaction cycles are performed to produce sufficient quantities of nucleic acid target gene molecule for subsequent steps including fragmentation and detection. In methods of selectively amplifying a nucleic acid target gene molecule using a methylation specific primer, at least one primer used in the amplification method will be methylation specific. Preferably the primers used in the amplification method are not methylation specific.

Primers used in the methods disclosed herein are of sufficient length and appropriate sequence to permit specific primer extension using a nucleic acid target gene molecule template. The primers are typically designed to be complementary to each strand of the nucleic acid target gene molecule to be amplified. The primer can be an oligodeoxyribonucleotide, an oligoribonucleotide, or an oligonucleotide containing both deoxyribonucleotides and ribonucleotides, in some embodiments, a primer can contain one or more nucleotide analogs. The length of primer can vary, depending on any of a variety of factors, including temperature, buffer, desired selectivity and nucleotide composition. The primer can contain at least about 5, 8, 10, 15, 20, 25, 30, 40, 50, 60, 70 or 80 nucleotides, and typically contains no more than about 120, 110, 100, 90, 70, 60, 50, 40, 30, 20 or 10 nucleotides.

The oligonucleotide primers used herein can be prepared using any suitable method, such as conventional phosphotriester and phosphodiester methods or automated embodiments thereof. In one such automated embodiment, diethylphosphoramidites are used as starting materials and can be synthesized as described by Beaucage, et al., *Tetrahedron Letters* 22:1859-1862 (1981). Methods for synthesizing oligonucleotides on a solid support are known in the art, as exemplified in U.S. Pat. No. 4,458,066.

A primer used in accordance with the disclosed amplification and nucleic acid synthesis methods can specifically hybridize to a nucleic acid target gene molecule.

In methods provided herein, the nucleotide sequence of a nucleic acid target gene molecule can be modified as a function of the methylation state of the nucleic acid target gene molecule. Accordingly, the primer binding region of a methylation-specific reagent-treated nucleic acid target gene molecule that corresponds to a methylation state of a region of an untreated nucleic acid target gene molecule can be a primer binding region whose nucleotide sequence reflects the methylation state of that region in the untreated nucleic acid target gene molecule. For example, a region of an untreated nucleic acid target gene molecule that contains a methylcytosine at the 4th nucleotide and an unmethylated cytosine at the 7th nucleotide can be treated with bisulfite, which will convert the cytosine at the $7^{th}$ nucleotide to uracil without changing the methylcytosine at the $4^{th}$ nucleotide; thus, a primer binding region of the treated nucleic acid target gene molecule that corresponds to that region of the untreated nucleic acid target gene molecule will contain a cytosine at the 4th nucleotide and a uracil (or thymine) at the 7th nucleotide, and a primer complementary to such a primer binding region will contain an adenine at the locus complementary to the 4th nucleotide and a guanine at the locus complementary to the $7^{th}$ nucleotide.

The methylation specific primers may be used in methods to specifically amplify nucleic acid target gene molecules according to the methylation state of the nucleic acid target gene molecule, and to thereby selectively increase the amount of nucleic acid target gene in a sample. Methylation state specific amplification methods include one or more nucleic acid synthesis steps, using one or more methylation specific primers.

In accordance with the methods disclosed herein, a nucleic acid target gene sequence can serve as a template for one or more steps of nucleic acid synthesis. The nucleic acid synthesis step or steps can include primer extension, DNA replication, polymerase chain reaction (PCR), reverse transcription, reverse transcription polymerase chain reaction (RT-PCR), rolling circle amplification, whole genome amplification, strand displacement amplification (SDA), and transcription based reactions.

In one embodiment an amplification step can be performed that can amplify one or more nucleic acids without distinguishing between methylated and unmethylated nucleic acid molecules or loci. Such an amplification step can be performed, for example, when the amount of nucleic acid in a sample is very low and detection of methylated nucleic acid target gene molecules can be improved by a preliminary amplification step that does not distinguish methylated nucleic acid target gene molecules from unmethylated nucleic acid target gene molecules or other nucleic acids in the sample. Typically, such an amplification step is performed subsequent to treating the nucleic acid sample with a reagent that modifies the nucleotide sequence of nucleic acid molecules as a function of the methylation state of the nucleic acid molecules. Although this method does not distinguish according to methylation state, the primers used in such an amplification step nevertheless may be used to increase the amount of nucleic acid molecules of a particular nucleic acid target gene region to be examined relative to the total amount of nucleic acid in a sample. For example, primers can be designed to hybridize to a pre-determined region of a nucleic acid target gene molecule in order to increase the relative amount of that nucleic acid target gene molecule in the sample, but without amplifying the nucleic acid target gene molecule according to the methylation state of the nucleic acid target gene molecule. One skilled in the art may determine the primer used in such a preamplification, or amplification, step according to various known factors and including the desired selectivity of the amplification step and any known nucleotide sequence information.

In the methods of nucleic acid synthesis using a double-stranded nucleic acid molecule, the strands are first separated before any nucleic acid synthetic steps. Following strand separation, one or more primers can be hybridized to one or more treated single-stranded nucleic acid molecules to be amplified, and nucleotide synthesis can be performed to add nucleotides to each primer to form a strand complementary to the strand of the nucleic acid target gene molecule. In one embodiment, nucleic acid synthesis can be performed to selectively amplify one of two strands of a treated nucleic acid target gene molecule. In another embodiment, the step of synthesizing a strand complementary to each strand of a double-stranded treated nucleic acid target gene molecule is performed in the presence of two or more primers, such that at least one primer can hybridize to each strand and prime additional nucleotide synthesis.

In the methods of nucleic acid synthesis using a single-stranded nucleic acid molecule, a primer can be hybridized to the single-stranded nucleic acid molecule to be amplified, and nucleotide synthesis may be performed to add nucleotides to the primer to form a strand complementary to the single-stranded nucleic acid molecule. In one embodiment, the step of synthesizing a strand complementary to a single-stranded nucleic acid molecule is performed in the presence of two or more primers, such that one primer can hybridize to the nucleotide sequence of the strand of the nucleic acid target gene molecule, and one primer can hybridize to the synthesized complementary strand and prime additional nucleotide synthesis. For example, after synthesis of the complementary strand, PCR amplification of the nucleic acid molecule can be immediately performed without further manipulation of the sample.

In another embodiment, the step of synthesizing a strand complementary to a single-stranded nucleic acid molecule is performed separately from additional nucleotide synthetic reactions. For example, the complementary strand can be synthesized to form a double-stranded nucleic acid molecule, and the sample may be subjected to one or more intermediate steps prior to amplifying the double-stranded nucleic acid molecule. Intermediate steps may include any of a variety of methods of manipulating a nucleic acid sample, including increasing the purity of the nucleic acid molecule, removing excess primers, changing the reaction conditions (e.g., the buffer conditions, enzyme or reactants present in the sample), and other parameters. In one example, the sample may be subjected to one or more purification steps of the nucleic acid molecule. For example, the primer used to create the strand complementary to the nucleic acid molecule can contain a moiety at its 5' end that permits identification or isolation of the primer or of a nucleic acid into which the primer is incorporated. Such a moiety may be, for example, a bindable moiety such as biotin, polyhistidine, magnetic bead, or other suitable substrate, whereby contacting the sample with the binding partner of the bindable moiety may result in selective binding of nucleic acid molecule into which the primer has been incorporated. Such selective binding may be used to separate the nucleic acid molecule from sample impurities, thereby increasing the purity of the nucleic acid molecule. After performing one or more intermediate steps, such as purity enhancing steps, the nucleic acid molecule may be amplified according to the methods provided herein and as known in the art.

After formation of the strand complementary to the single-stranded nucleic acid target gene molecules, subsequent nucleic acid target gene molecule amplification steps may be performed in which the complementary strands are separated, primers are hybridized to the strands, and the primers have added thereto nucleotides to form a new complementary strand. Strand separation may be effected either as a separate step or simultaneously with the synthesis of the primer extension products. This strand separation may be accomplished using various suitable denaturing conditions, including physical, chemical, or enzymatic means, the word "denaturing" includes all such means. One physical method of separating nucleic acid strands involves heating the nucleic acid target gene molecule until it is denatured. Typical heat denaturation may involve temperatures ranging from about 80° C. to 105° C., for times ranging from about 1 to 10 minutes. Strand separation also may be accomplished by chemical means, including high salt conditions or strongly basic conditions. Strand separation also may be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling, *CSH-Quan tita rive Biology,* 43:63 (1978) and techniques for using RecA are reviewed in C. Radding, *Ann. Rev. Genetics* 16:405-437 (1982).

After each amplification step, the amplified product will be double stranded, with each strand complementary to the other. The complementary strands of may be separated, and both separated strands may be used as a template for the synthesis of additional nucleic acid strands. This synthesis may be performed under conditions allowing hybridization of primers to templates to occur. Generally synthesis occurs in a buffered aqueous solution, typically at about a pH of 7-9, such as about pH 8. Typically, a molar excess of two oligonucleotide primers can be added to the buffer containing the separated template strands. In some embodiments, the amount of target nucleic acid is not known (for example, when the methods disclosed herein are used for diagnostic applications), so that the amount of primer relative to the amount of complementary strand cannot be determined with certainty.

In an exemplary method, deoxyribonucleoside triphosphates dATP, dCTP, dGTP, and dTTP can be added to the synthesis mixture, either separately or together with the primers, and the resulting solution can be heated to about 90° C.-100° C. from about 1 to 10 minutes, typically from 1 to 4 minutes. After this heating period, the solution can be allowed to cool to about room temperature. To the cooled mixture can be added an appropriate enzyme for effecting the primer extension reaction (called herein "enzyme for polymerization"), and the reaction can be allowed to occur under conditions known in the art. This synthesis (or amplification) reaction can occur at room temperature up to a temperature above which the enzyme for polymerization no longer functions. For example, the enzyme for polymerization also may be used at temperatures greater than room temperature if the enzyme is heat stable. In one embodiment, the method of amplifying is by PCR, as described herein and as is commonly used by those of skill in the art. Alternative methods of amplification have been described and also may be employed. A variety of suitable enzymes for this purpose are known in the art and include, for example, *E. coli* DNA polymerase I, Klenow fragment of *E. coli* DNA polymerase I, T4 DNA polymerase, other available DNA polymerases, polymerase muteins, reverse transcriptase, and other enzymes, including thermostable enzymes (i.e., those enzymes which perform primer extension at elevated temperatures, typically temperatures that cause denaturation of the nucleic acid to be amplified).

Manipulation of Both Strands of a Nucleic Acid Target Gene Molecule

Methods of manipulating a nucleic acid target gene molecule subsequent to methylation based sequence modification treatment, such as amplification and fragmentation, may be performed using only one strand of the treated nucleic acid target gene molecule, or using both strands of the treated nucleic acid target gene molecule. For example, primers used for amplification steps may be complementary to only one strand of the treated nucleic acid target gene molecule, or may be complementary to both strands of the treated nucleic acid. Accordingly, amplification steps may be performed to create at least two different amplified double-stranded products, where both strands of the treated nucleic acid target gene molecule is amplified into separate double-stranded products.

Alternatively, amplification may be performed such that only one of the two strands of the treated nucleic acid target gene molecule is amplified. For example, when amplification is performed using at least one primer that is selective for the sequence of one of the two strands, the strand hybridized to the primer may be selectively amplified.

After one or more steps of amplification, the amplified products may be subjected to one or more manipulation steps prior to additional amplification steps or prior to cleavage steps. For example, amplified products can be subjected to one or more purification steps prior to additional amplification or prior to cleavage.

Methods for purifying nucleic acid molecules are known in the art and include precipitation, dialysis or other solvent exchange, gel electrophoresis, enzymatic degradation of impurities (e.g., protease treatment, or RNase treatment for a DNA nucleic acid target gene molecule sample), liquid chromatography including ion exchange chromatography and affinity chromatography, and other methods of specifically binding nucleic acid target gene molecules to separate them from impurities (e.g., hybridization, biotin binding). Purification steps also may include separating complementary strands of amplification products. One skilled in the art will know to select which, if any, purification steps to use according to desired level of purity and/or desired sample composition for subsequent amplification, modification or cleavage steps.

Methods for determining methylation in a nucleic acid target gene may include methods in which a single sample is treated in one or more steps, and then the single sample may be divided into two or more aliquots for parallel treatment in subsequent steps.

Amplified products may be split into two or more aliquots after amplification. For example, amplified products may be split into two or more aliquots after amplification but prior to cleaving the amplified products, amplified products may split into two or more aliquots after amplification and subjected to further steps such as one or more amplified product purification steps.

When amplified products are split into two or more aliquots prior to cleavage, different cleavage methods may be applied to each of the two or more aliquots. For example, a first nucleic acid target gene molecule aliquot may be base specifically fragmented with RNase A, while a second nucleic acid target gene molecule aliquot may be base specifically fragmented with Rnase T1. In another example, amplified nucleic acid target gene molecule may be split into four aliquots and each aliquot may be treated with a different base-specific reagent to produce four different sets of base specifically cleaved nucleic acid target gene molecule fragments. Separation into two or more aliquots permits different cleavage reactions to be performed on the same amplification product. Use of different cleavage reactions on the same amplification product is further described in the cleavage methods provided herein.

A sample may be divided into two or more aliquots in specifically amplifying different strands of a nucleic acid target gene molecule in different aliquots. For example, a treated nucleic acid target gene molecule can have non-complementary strands that can be separately treated with different primers such as different methylation state specific primers in separately amplifying the different strands in different aliquots. In another embodiment, complementary strands of an amplified nucleic acid target gene molecule can be separately amplified in different aliquots, according to the primers used in each aliquot. For example, a sample of amplified nucleic acid target gene molecules can be separated into two or more aliquots, where the forward strand is transcribed in a first set of aliquots and the reverse strand is transcribed in a second set of aliquots. As will be appreciated by one skilled in the art, a sample can be divided into any of a plurality of aliquots in which any combination of the parallel reactions described herein may be performed.

Fragmentation in Conjunction with Nucleotide Synthesis

Selective nucleotide synthesis also may be performed in conjunction with fragmentation. A nucleic acid target gene amplified through a plurality of nucleic acid synthesis cycles will utilize primers hybridizing to two separate regions of the nucleic acid target gene molecule. Fragmentation of a nucleic acid target gene molecule in the center region in between the two primer hybridization sites will prevent amplification of the nucleic acid target gene molecule. Hence selective fragmentation of the center region of nucleic acid molecules may result in selective amplification of a nucleic acid target gene molecule even if the primers used in the nucleic acid synthesis reactions are not selective.

In one example, the sample may be treated with fragmentation conditions prior to being treated with nucleic acid synthesis conditions, and prior to being treated with a reagent that modifies the nucleic acid target gene molecule sequence as a function of the methylation state of the nucleic acid target gene. In such an example, the fragmentation conditions may be selective for methylated or unmethylated nucleotides. For example, a sample can have added thereto a methylation sensitive endonuclease, such as HPAII, which cleaves at an unmethylated recognition site but not at a methylated recognition site. This results in a sample containing intact nucleic acid target gene molecules that are methylated at the recognition site and cleaved nucleic acid target gene molecules that are unmethylated at the recognition site. The sample then may be treated with nucleic acid synthesis conditions using primers designed so that only uncleaved nucleic acid target gene molecules are amplified. As a result of the cleavage, amplification will be selective for nucleic acid target gene molecules that are methylated at the recognition site.

In another example, the sample may be treated with fragmentation conditions prior to treatment with nucleic acid synthesis conditions, but subsequent to treatment with a reagent that modifies the nucleic acid target gene molecule sequence as a function of the methylation state of the nucleic acid target gene. For example, a sample can have added thereto an endonuclease that cleaves at a recognition site that includes a C nucleotide at a particular locus, but not a recognition site that contains a T or U nucleotide at that particular locus. Or vice versa, a sample can have added thereto an endonuclease that cleaves at a recognition site that includes a T or U nucleotide at a particular locus, but not a recognition site that contains a C nucleotide at that particular locus. The sample can first be treated with a reagent that modifies the nucleic acid target gene molecule sequence as a function of the methylation state of the nucleic acid target gene molecule, and then treated with such an endonuclease. The resulting sample will contain intact nucleic acid target gene molecules that have the desired methylation state at the recognition site and cleaved nucleic acid target gene molecules that have the undesired methylation state at the recognition site. The sample then can be treated with nucleic acid synthesis conditions using primers designed so that only uncleaved nucleic acid target gene molecules are amplified. As a result of the cleavage, amplification will be selective for nucleic acid target gene molecules that are methylated at the recognition site.

Transcription

Transcription of template DNA such as a nucleic acid target gene molecule, or an amplified product thereof, may be performed for one strand of the template DNA or for both strands of the template DNA. In one embodiment, the nucleic acid molecule to be transcribed contains a moiety to which an enzyme capable of performing transcription can bind; such a moiety may be, for example, a transcriptional promotor sequence.

Transcription reactions may be performed using any of a variety of methods known in the art, using any of a variety of enzymes known in the art. For example, mutant T7 RNA polymerase (T7 R&DNA polymerase; Epicentre, Madison, Wis.) with the ability to incorporate both dNTPs and rNTPs may be used in the transcription reactions. The transcription reactions may be run under standard reaction conditions known in the art, for example, 40 mM Tris-Ac (pH 7.51, 10 mM NaCl, 6 mM MgCl, 2 mM spermidine, 10 mM dithiothreitol, 1 mM of each rNTP, 5 mM of dNTP (when used), 40 nM DNA template, and 5 U/uL T7 R&DNA polymerase, incubating at 37° C. for 2 hours. After transcription, shrimp alkaline phosphatase (SAP) may be added to the cleavage reaction to reduce the quantity of cyclic monophosphate side products. Use of T7 R&DNA polymerase is known in the art, as exemplified by U.S. Pat. Nos. 5,849,546 and 6,107,037, and Sousa et al., EMBO J. 14:4609-4621 (1995), Padilla et al., Nucl. Acid Res. 27:1561-1563 (1999), Huang et al., Biochemistry 36:8231-8242 (1997), and Stanssens et al., Genome Res., 14:126-133 (2004).

In addition to transcription with the four regular ribonucleotide substrates (rCTP, rATP, rGTP and rUTP), reactions may be performed replacing one or more ribonucleoside triphosphates with nucleoside analogs, such as those provided herein and known in the art, or with corresponding deoxyribonucleoside triphosphates (e.g., replacing rCTP with dCTP, or replacing rUTP with either dUTP or dTTP). In one embodiment, one or more rNTPs are replaced with a nucleoside or nucleoside analog that, upon incorporation into the transcribed nucleic acid, is not cleavable under the fragmentation conditions applied to the transcribed nucleic acid.

In one embodiment, transcription is performed subsequent to one or more nucleic acid synthesis reactions, including one or more nucleic acid synthesis reactions using methylation specific primers. For example, transcription of an amplified product can be performed subsequent to amplification of a nucleic acid target gene molecule, including methylation specific amplification of the nucleic acid target gene molecule. In another embodiment, the treated nucleic acid target gene molecule is transcribed without any preceding nucleic acid synthesis steps.

Fragmentation of Nucleic Acid Molecules

The methods provided herein also include steps of fragmentation and/or cleavage of nucleic acid target gene molecules or amplified products. Any method for cleaving a nucleic acid molecule into fragments with a suitable fragment size distribution may be used to generate the nucleic acid fragments. Fragmentation of nucleic acid molecules is known in the art and may be achieved in many ways. For example, nucleic acid molecules composed of DNA, RNA, analogs of DNA and RNA or combinations thereof, can be fragmented physically, chemically, or enzymatically. In one embodiment, enzymatic cleavage at one or more specific cleavage sites can be used to produce the nucleic acid molecule fragments utilized herein. Typically, cleavage is effected after amplification such that once a sufficient quantity of amplified products is generated using the methods provided herein, the amplified products can be cleaved into two or more fragments.

In embodiments where restriction enzymes are used, depending on the number and type of restriction enzymes used and the particular reaction conditions selected, the average length of fragments generated may be controlled within a specified range. In particular embodiments, fragments of nucleic acid molecules prepared for use herein may range in size from the group of ranges including about 1-50 bases, about 2-40 bases, about 3-35 bases, and about 5-30 bases. Yet other size ranges contemplated for use herein include between about 50 to about 150 bases, from about 25 to about 75 bases, or from about 12-30 bases. In one particular embodiment, fragments of about 3 to about 35 bases are used. Generally, fragment size range will be selected so that the mass of the fragments can be accurately determined using the mass measurement methods described herein and known in the art; also in some embodiments, size range is selected in order to facilitate the desired desorption efficiencies in MALDI-TOF MS.

Base-specific fragmentation using nucleases is a preferred fragmentation method. Nucleic acid target gene molecules may be fragmented using nucleases that selectively cleave at a particular base (e.g., A, C, T or G for DNA and A, C, U or G for RNA) or base type (i.e., pyrimidine or purine). In one embodiment, RNases that specifically cleave 3 RNA nucleotides (e.g., U, G and A), 2 RNA nucleotides (e.g., C and U) or 1 RNA nucleotide (e.g., A), may be used to base specifically cleave transcripts of a nucleic acid target gene molecule. For example, RNase T1 cleaves ssRNA (single-stranded RNA) at G ribonucleotides, RNase U2 digests ssRNA at A ribonucleotides, RNase CL3 and cusativin cleave ssRNA at C ribonucleotides, PhyM cleaves ssRNA at U and A ribonucleotides, and RNAse A cleaves ssRNA at pyrimidine ribonucleotides (C and U). The use of mono-specific Rnases such as RNase T, (G specific) and RNase U, (A specific) is known in the art (Donis-Keller et al., Nucl. Acids Res. 4:2527-2537 (1977); Gupta and Randerath, Nucl. Acids Res. 4:1957-1978 (1977); Kuchino and Nishimura, Methods Enzymol. 180:154-163 (1989); and Hahner et al., Nucl. Acids Res. 25(10):1957-1964 (1997)). Another enzyme, chicken liver ribonuclease (RNase CL3) has been reported to cleave preferentially at cytidine, but the enzyme's proclivity for this base has been reported to be affected by the reaction conditions (Boguski et al., J. Biol. Chem. 255:2160-2163 (1980)). Reports also claim cytidine specificity for another ribonuclease, cusativin, isolated from dry seeds of *Cucumis sativus* L (Rojo et al., Planta 194:328-338 (1994)). Alternatively, the identification of pyrimidine residues by use of RNase PhyM (A and U specific) (Donis-Keller, H. Nucleic Acids Res. 8:3133-3142 (1980)) and RNase A (C and U specific) (Simoncsits et al., Nature 269:833-836 (1977); Gupta and Randerath, Nucl. Acids Res. 4:1957-1978 (1977)) has been demonstrated. Examples of such cleavage patterns are given in Stanssens et al., WO 00/66771.

script of a particular nucleic acid target gene molecule can be subjected to G-specific cleavage using RNAse T1; the transcript can be subjected to C-specific cleavage using dTTP in the transcription reaction, followed by digestion with RNAse A; and the transcript can be subjected to T-specific cleavage using dCTP in the transcription reaction, followed by digestion with RNAse A. These types of base specific cleavage patterns are exemplified below showing the theoretical cleavage products of a given nucleotide sequence TAACGCAT converted through bisulfite treatment to the sequence TAAACGTAT if methylated at the cytosine and to TAAATGTAT if not methylated.

|  | Non-methylated TAAATGTAT | Type of change | Methylated TAAACGTAT |
|---|---|---|---|
| RNAse A C specific cleavage | TAAATGTAT | Introduction of cleavage nucleotide | TAAAC GTAT |
| RNA se A T specific cleavage | T AAAT GT AT | Removal of cleavage nucleotide | T AAACGT AT |
| RNAse T1 G specific cleavage | TAAATG TAT | Mass Shift | TAAACG TAT |

Base specific cleavage reaction conditions using an RNase are known in the art, and can include, for example 4 mM Tris-Ac (pH 8.01, 4 mM KAc, 1 mM spermidine, 0.5 mM dithiothreitol and 1.5 mM MgCl.

In one embodiment, amplified product can be transcribed into a single stranded RNA molecule and then cleaved base specifically by an endoribonuclease. Treatment of the target nucleic acid, for example using bisulfite which converts unmethylated cytosine to uracil without modifying methylated cytosine, can be used to generate differences in base specific cleavage patterns that can be analyzed by mass analysis methods, such as mass spectrometry, and can be used for identification of methylated sites. In one embodiment, transcription of a nucleic acid target gene molecule can yield an RNA molecule that can be cleaved using specific RNA endonucleases. For example, base specific cleavage of the RNA molecule can be performed using two different endoribonucleases, such as RNAse T1 and RNAse A. RNAse T1 specifically cleaves G nucleotides, and RNAse A specifically cleaves pyrimidine ribonucleotides (i.e., cytosine and uracil residues). In one embodiment, when an enzyme that cleaves more than one nucleotide, such as RNAse A, is used for cleavage, non-cleavable nucleosides, such as dNTP's may be incorporated during transcription of the nucleic acid target gene molecule or amplified product. For example, dCTPs may be incorporated during transcription of the amplified product, and the resultant transcribed nucleic acid can be subject to cleavage by RNAse A at U ribonucleotides, but resistant to cleavage by RNAse A at C deoxyribonucleotides. In another example, dTTPs can be incorporated during transcription of the nucleic acid target gene molecule, and the resultant transcribed nucleic acid can be subject to cleavage by RNAse A at C ribonucleotides, but resistant to cleavage by RNAse A at T deoxyribonucleotides. By selective use of non-cleavable nucleosides such as dNTPs, and by performing base specific cleavage using RNases such as RNAse A and RNAse T1, base cleavage specific to three different nucleotide bases can be performed on the different transcripts of the same target nucleic acid sequence. For example, the tran- In another embodiment, the use of dNTPs, different RNAses, and both orientations of the nucleic acid target gene molecule can allow for six different cleavage schemes. For example, a double stranded nucleic acid target gene molecule can yield two different single stranded transcription products, which can be referred to as a transcript product of the forward strand of the nucleic acid target gene molecule and a transcript product of the reverse strand of the nucleic acid target gene molecule. Each of the two different transcription products can be subjected to three separate base specific cleavage reactions, such as G-specific cleavage, C-specific cleavage and T-specific cleavage, as described herein, to result in six different base specific cleavage reactions. The six possible cleavage schemes are listed below.

|  | Forward Primer | Reverse primer |
|---|---|---|
| RNAse T1 | G specific cleavage | G specific cleavage |
| RNAse A: dCTP | T specific cleavage | T specific cleavage |
| RNAse A: dCTP | C specific cleavage | C specific cleavage |

Use of four different base specific cleavage reactions can yield information on all four nucleotide bases of one strand of the nucleic acid target gene molecule. That is, by taking into account that cleavage of the forward strand can be mimicked by cleaving the complementary base on the reverse strand, base specific cleavage can be achieved for each of the four nucleotides of the forward strand by reference to cleavage of the reverse strand. For example, the three base-specific cleavage reactions can be performed on the transcript of the nucleic acid target gene molecule forward strand, to yield G-, C- and T-specific cleavage of the nucleic acid target gene molecule forward strand; and a fourth base specific cleavage reaction can be a T-specific cleavage reaction of the transcript of the nucleic acid target gene molecule reverse strand, the results of which will be equivalent to A-specific cleavage of the transcript of the nucleic acid target gene molecule forward strand. One skilled in the art will appreciate that base specific cleavage to yield information on all four nucleotide bases of one nucleic acid target gene molecule strand can be accomplished using a variety of different combinations of possible base specific cleavage reactions, including cleavage reactions listed above for RNases T1 and A, and additional cleavage reactions for forward or reverse strands and/or using non-hydrolyzable nucleotides can be performed with other base specific RNases known in the art or disclosed herein.

In one example, RNAse U2 can be used to base specifically cleave nucleic acid target gene molecule transcripts. RNAse U2 can base specifically cleave RNA at A nucleotides. Thus, by use of RNAses T1, U2 and A, and by use of the appropriate dNTPs (in conjunction with use of RNase A), all four base positions of a nucleic acid target gene molecule can be examined by base specifically cleaving transcript of only one strand of the nucleic acid target gene molecule. In some embodiments, non-cleavable nucleoside triphosphates are not required when base specific cleavage is performed using RNAses that base specifically cleave only one of the four ribonucleotides. For example, use of RNAse T1, RNase CL3, cusativin, or RNAse U2 for base specific cleavage does not require the presence of non-cleavable nucleotides in the nucleic acid target gene molecule transcript. Use of RNAses such as RNAse T1 and RNAse U2 can yield information on all four nucleotide bases of a nucleic acid target gene molecule. For example, transcripts of both the forward and reverse strands of a nucleic acid target gene molecule or amplified product can be synthesized, and each transcript can be subjected to base specific cleavage using RNAse T1 and RNAse U2. The resulting cleavage pattern of the four cleavage reactions will yield information on all four nucleotide bases of one strand of the nucleic acid target gene molecule. In such an embodiment, two transcription reactions can be performed: a first transcription of the forward nucleic acid target gene molecule strand and a second of the reverse nucleic acid target gene molecule strand.

Also contemplated for use in the methods are a variety of different base specific cleavage methods. A variety of different base specific cleavage methods are known in the art and are described herein, including enzymatic base specific cleavage of RNA, enzymatic base specific cleavage of modified DNA, and chemical base specific cleavage of DNA. For example enzymatic base specific cleavage, such as cleavage using uracil-deglycosylase (UDG) or methylcytosine deglycosylase (MCDG), are known in the art and described herein, and can be performed in conjunction with the enzymatic RNAse-mediated base specific cleavage reactions described herein.

Methods for using restriction endonucleases to fragment nucleic acid molecules are widely known in the art. In one exemplary protocol a reaction mixture of 20-50 ul is prepared containing; DNA 1-3 ug; restriction enzyme buffer 1×; and a restriction endonuclease 2 units for 1ug of DNA. Suitable buffers also are known in the art and include suitable ionic strength, cofactors, and optionally, pH buffers to provide optimal conditions for enzymatic activity. Specific enzymes may require specific buffers that are generally available from commercial suppliers of the enzyme. An exemplary buffer is potassium glutamate buffer (KGB). Hannish, J. and M. McClelland, "Activity of DNA modification and restriction enzymes in KGB, a potassium glutamate buffer," *Gene Anal. Tech* 5:105 (1988); McClelland, M. et al., "A single buffer for all restriction endonucleases," *Nucl. Acids Res.* 16:364 (1988). The reaction mixture is incubated at 37° C. for 1 hour or for any time period needed to produce fragments of a desired size or range of sizes. The reaction may be stopped by heating the mixture at 65° C. or 80° C. as needed. Alternatively, the reaction may be stopped by chelating divalent cations such as $Mg^{2+}$ with for example, EDTA.

DNAses also may be used to generate nucleic acid molecule fragments. Anderson, S., "Shotgun DNA sequencing using cloned Dnase I-generated fragments," *Nucl. Acids Res.* 9:3015-3027 (1981). DNase I (Deoxyribonuclease I) is an endonuclease that non-specifically digests double- and single-stranded DNA into poly- and mono-nucleotides.

Catalytic DNA and RNA are known in the art and can be used to cleave nucleic acid molecules to produce nucleic acid molecule fragments. Santoro, S. W. and Joyce, G. F. "A general purpose RNA-cleaving DNA enzyme," *Proc. Natl. Acad. Sci. USA* 94:4262-4266 (1997). DNA as a single-stranded molecule can fold into three-dimensional structures similar to RNA, and the 2'-hydroxy group is dispensable for catalytic action. As ribozymes, DNAzymes also can be made, by selection, to depend on a cofactor. This has been demonstrated for a histidine-dependent DNAzyme for RNA hydrolysis. U.S. Pat. Nos. 6,326,174 and 6,194,180 disclose deoxyribonucleic acid enzymes, catalytic and enzymatic DNA molecules, capable of cleaving nucleic acid sequences or molecules, particularly RNA.

Fragmentation of nucleic acid molecules may be achieved using physical or mechanical forces including mechanical shear forces and sonication. Physical fragmentation of nucleic acid molecules may be accomplished, for example, using hydrodynamic forces. Typically nucleic acid molecules in solution are sheared by repeatedly drawing the solution containing the nucleic acid molecules into and out of a syringe equipped with a needle. Thorstenson, Y. R. et al., "An Automated Hydrodynamic Process for Controlled, Unbiased DNA Shearing," Genome Research 8:848-855 (1998); Davison, P. F. Proc. Natl. Acad. Sci. USA 45:1560-1568 (1959); Davison, P. F. Nature 185:918-920 (1960); Schriefer, L. A. et al., "Low pressure DNA shearing: a method for random DNA sequence analysis," *Nucl. Acids Res.* 18:7455-7456 (1990). Shearing of DNA, for example with a hypodermic needle, typically generates a majority of fragments ranging from 1-2 kb, although a minority of fragments can be as small as 300 bp.

The hydrodynamic point-sink shearing method developed by Oefner et al., is one method of shearing nucleic acid molecules that utilizes hydrodynamic forces. Oefner, P. J. et al., "Efficient random subcloning of DNA sheared in a recirculating point-sink flow system," *Nucl. Acids Res.* 24(20): 3879-3886 (1996).

Nucleic acid molecule fragments also may be obtained by agitating large nucleic acid molecules in solution, for example by mixing, blending, stirring, or vortexing the solution. Hershey, A. D. and Burgi, E. *J. Mol. Biol,* 2:143-152 (1960); Rosenberg, H. S. and Bendich, A. *J. Am. Chem. Soc.* 82:3198-3201 (1960).

One suitable method of physically fragmenting nucleic acid molecules is based on sonicating the nucleic acid molecule. Deininger, P. L. "Approaches to rapid DNA sequence analysis," *Anal. Biochem.* 129:216-223 (1983).

Fragmentation of nucleic acid molecules also may be achieved using a nebulizer. Bodenteich, A., Chissoe, S., Wang, Y.-F. and Roe, B. A. (1994) In Adams, M. D., Fields, C. and Venter, J. C. (eds.) Automated DNA Sequencing and Analysis. Academic Press, San Diego, Calif. Nebulizers are known in the art and commercially available.

Another method for fragmenting nucleic acid molecule employs repeatedly freezing and thawing a buffered solution of nucleic acid molecules. The sample of nucleic acid molecules may be frozen and thawed as necessary to produce fragments of a desired size or range of sizes.

Nucleic acid molecule fragmentation also may be achieved by irradiating the nucleic acid molecules. Typically, radiation such as gamma or x-ray radiation will be sufficient to fragment the nucleic acid molecules.

Chemical fragmentation may be used to fragment nucleic acid molecules either with base specificity or without base specificity. Nucleic acid molecules may be fragmented by chemical reactions including for example, hydrolysis reactions including base and acid hydrolysis. An exemplary acid/base hydrolysis protocol for producing nucleic acid molecule fragments are known (see, e.g., Sargent et al., *Meth. Enz.* 152:432 (1988)).

Mass Spectrometry

When analyses are performed using mass spectrometry, such as MALDI, nanoliter volumes of sample can be loaded on chips. Use of such volumes can permit quantitative or semi-quantitative mass spectrometric results. For example, the area under the peaks in the resulting mass spectra are proportional to the relative concentrations of the components of the sample. Methods for preparing and using such chips are known in the art, as exemplified in U.S. Pat. No. 6,024,925, U.S. Publication 20010008615, and PCT Application No. PCT/US97/20195 (WO 98/20020); methods for preparing and using such chips also are provided in co-pending U.S. application Ser. Nos. 08/786,988, 09/364,774, and 09/297,575. Chips and kits for performing these analyses are commercially available from SEQUENOM under the trademark MassARRAY™. MassARRAY™ systems contain a miniaturized array such as a SpectroCHIP@ useful for MALDI-TOF (Matrix-Assisted Laser Desorption Ionization-Time of Flight) mass spectrometry to deliver results rapidly. It accurately distinguishes single base changes in the size of DNA fragments relating to genetic variants without tags.

In one embodiment, the mass of all nucleic acid molecule fragments formed in the step of fragmentation is measured. The measured mass of a nucleic acid target gene molecule fragment or fragment of an amplification product also can be referred to as a "sample" measured mass, in contrast to a "reference" mass which arises from a reference nucleic acid fragment.

In another embodiment, the length of nucleic acid molecule fragments whose mass is measured using mass spectroscopy is no more than 75 nucleotides in length, no more than 60 nucleotides in length, no more than 50 nucleotides in length, no more than 40 nucleotides in length, no more than 35 nucleotides in length, no more than 30 nucleotides in length, no more than 27 nucleotides in length, no more than 25 nucleotides in length, no more than 23 nucleotides in length, no more than 22 nucleotides in length, no more than 21 nucleotides in length, no more than 20 nucleotides in length, no more than 19 nucleotides in length, or no more than 18 nucleotides in length. In another embodiment, the length of the nucleic acid molecule fragments whose mass is measured using mass spectroscopy is no less than 3 nucleotides in length, no less than 4 nucleotides in length, no less than 5 nucleotides in length, no less than 6 nucleotides in length, no less than 7 nucleotides in length, no less than 8 nucleotides in length, no less than 9 nucleotides in length, no less than 10 nucleotides in length, no less than 12 nucleotides in length, no less than 15 nucleotides in length, no less than 18 nucleotides in length, no less than 20 nucleotides in length, no less than 25 nucleotides in length, no less than 30 nucleotides in length, or no less than 35 nucleotides in length.

In one embodiment, the nucleic acid molecule fragment whose mass is measured is RNA. In another embodiment the nucleic acid target gene molecule fragment who's mass is measured is DNA. In yet another embodiment, the nucleic acid target gene molecule fragment whose mass is measured contains one modified or atypical nucleotide (i.e., a nucleotide other than deoxy-C, T, G or A in DNA, or other than C, U, G or A in RNA). For example, a nucleic acid molecule product of a transcription reaction may contain a combination of ribonucleotides and deoxyribonucleotides. In another example, a nucleic acid molecule can contain typically occurring nucleotides and mass modified nucleotides, or can contain typically occurring nucleotides and non-naturally occurring nucleotides.

Prior to mass spectrometric analysis, nucleic acid molecules can be treated to improve resolution. Such processes are referred to as conditioning of the molecules. Molecules can be "conditioned," for example to decrease the laser energy required for volatilization and/or to minimize fragmentation. A variety of methods for nucleic acid molecule conditioning are known in the art. An example of conditioning is modification of the phosphodiester backbone of the nucleic acid molecule (e.g., by cation exchange), which can be useful for eliminating peak broadening due to a heterogeneity in the cations bound per nucleotide unit. In another example, contacting a nucleic acid molecule with an alkylating agent such as alkyloidide, iodoacetamide, P-iodoethanol, or 2,3-epoxy-1-propanol, can transform a monothio phosphodiester bonds of a nucleic acid molecule into a phosphotriester bond. Likewise, phosphodiester bonds can be transformed to uncharged derivatives employing, for example, trialkylsilyl chlorides. Further conditioning can include incorporating nucleotides that reduce sensitivity for depurination (fragmentation during MS) e.g., a purine analog such as N7- or N9-deazapurine nucleotides, or RNA building blocks or using oligonucleotide triesters or incorporating phosphorothioate functions which are alkylated, or employing oligonucleotide mimetics such as PNA.

For some applications, simultaneous detection of more than one nucleic acid molecule fragment may be performed. In other applications, parallel processing can be performed using, for example, oligonucleotide or oligonucleotide mimetic arrays on various solid supports. "Multiplexing" can be achieved by several different methodologies. For example, fragments from several different nucleic acid molecules can be simultaneously subjected to mass measurement methods. Typically, in multiplexing mass measurements, the nucleic acid molecule fragments should be distinguishable enough so that simultaneous detection of the multiplexed nucleic acid molecule fragments is possible. Nucleic acid molecule fragments may be made distinguishable by ensuring that the masses of the fragments are distinguishable by the mass measurement method to be used. This may be achieved either by the sequence itself (composition or length) or by the introduction of mass-modifying functionalities into one or more nucleic acid molecules.

In one embodiment, the nucleic acid molecule to be mass-measured contains attached thereto one or more mass-modifying moieties. Mass-modifying moieties are known in the art and may be attached to the 3' end or 5' end of a nucleic acid molecule fragment, may be attached to a nucleobase or to a sugar moiety of a nucleotide, or may be attached to or substitute for the phosphodiester linkage between nucleotides. A simple mass-modification may be achieved by substituting H for halogens like F, Cl, Br and/or I, or pseudohalogens such as SCN, NCS, or by using different alkyl, aryl or aralkyl moieties such as methyl, ethyl, propyl, isopropyl, t-butyl, hexyl, phenyl, substituted phenyl, benzyl, or functional groups such as $N_3$, $CH_2F$, $CHF_2$, $CF_3$, $Si(CH_3)_3$, $Si(CH_3)_2$, $(C_2H_5)$, $Si(CH_3)(C_2H_5)_2$, $Si(C_2H_5)_3$. Yet another mass-modification can be obtained by attaching homo- or heteropeptides through the nucleic acid molecule (e.g., detector (D)) or nucleoside triphosphates. One example useful in generating mass-modified species with a mass increment of 57 is the attachment of oligoglycines, e.g., mass-modifications of 74, 131, 188, 245 are achieved. Simple oligoamides also can be used, e.g., mass-modifications of 74, 88, 102, 116 . . . , are obtainable.

Mass-modifications also may include oligo/polyethylene glycol derivatives. The oligo/polyethylene glycols also can be monoalkylated by a lower alkyl such as methyl, ethyl, propyl, isopropyl, t-butyl and other suitable substituents. Other chemistries also can be used in the mass-modified compounds (see, e.g., those described in Oligonucleotides and Analogues, A Practical Approach, F. Eckstein, editor, IRL Press, Oxford, 1991).

Mass modifying moieties can be attached, for instance, to either the 5'-end of the oligonucleotide, to the nucleobase (or bases), to the phosphate backbone, to the 2'-position of the nucleoside (nucleosides), and/or to the terminal 3'-position. Examples of mass modifying moieties include, for example, a halogen, an azido, or of the type, XR, wherein X is a linking group and R is a mass-modifying functionality. A mass-modifying functionality can, for example, be used to introduce defined mass increments into the oligonucleotide molecule, as described herein. Modifications introduced at the phosphodiester bond such as with alpha-thio nucleoside triphosphates, have the advantage that these modifications do not interfere with accurate Watson-Crick base-pairing and additionally allow for the one-step post-synthetic site-specific modification of the complete nucleic acid molecule e.g., via alkylation reactions (see, e.g., Nakamaye et al., *Nucl. Acids Res.* 23:9947-9959(1988)). Exemplary mass-modifying functionalities are boron-modified nucleic acids, which can be efficiently incorporated into nucleic acids by polymerases (see, e.g., Porter et al., *Biochemistry* 34: 11963-11969 (1995); Hasan et al., *Nucl. Acids Res.* 24:2150-2157 (1996); Li et al. *Nucl. Acids Res.* 23:4495-4501 (1995)).

Furthermore, the mass-modifying functionality may be added so as to affect chain termination, such as by attaching it to the 3'-position of the sugar ring in the nucleoside triphosphate. For those skilled in the art, it is clear that many combinations can be used in the methods provided herein. In the same way, those skilled in the art will recognize that chain-elongating nucleoside triphosphates also can be mass-modified in a similar fashion with numerous variations and combinations in functionality and attachment positions.

Different mass-modified nucleotides may be used to simultaneously detect a variety of different nucleic acid fragments simultaneously. In one embodiment, mass modifications can be incorporated during the amplification process. In another embodiment, multiplexing of different nucleic acid target gene molecules may be performed by mass modifying one or more nucleic acid target gene molecules, where each different nucleic acid target gene molecule can be differently mass modified, if desired.

Additional mass measurement methods known in the art may be used in the methods of mass measurement, including electrophoretic methods such as gel electrophoresis and capillary electrophoresis, and chromatographic methods including size exclusion chromatography and reverse phase chromatography.

Using methods of mass analysis such as those described herein, information relating to mass of the nucleic acid target gene molecule fragments can be obtained. Additional information of a mass peak that can be obtained from mass measurements include signal to noise ratio of a peak, the peak area (represented, for example, by area under the peak or by peak width at half-height), peak height, peak width, peak area relative to one or more additional mass peaks, peak height relative to one or more additional mass peaks, and peak width relative to one or more additional mass peaks. Such mass peak characteristics may be used in the present methylation identification methods, for example, in a method of identifying the methylation state of a nucleotide locus of a nucleic acid target gene molecule by comparing at least one mass peak characteristic of an amplification fragment with one or more mass peak characteristics of one or more reference nucleic acids.

Methylation State Identification

Fragment measurements may be used to identify the methylation state of a nucleic acid target gene molecule or to identify the methylation state of a particular nucleotide locus of a nucleic acid target gene molecule. Fragment measurements may be used to identify whether or not a nucleic acid target gene molecule contains one or more methylated or unmethylated nucleotides, such as methylcytosine or cytosine, respectively; to determine the number of methylated or unmethylated nucleotides such as methylcytosine or cytosine, respectively, present in a nucleic acid target gene molecule, to identify whether or not a nucleotide locus, such as a cytosine locus, is methylated or unmethylated in a nucleic acid target gene molecule, to identify the nucleotide locus of a methylated or unmethylated nucleotide, such as methylcytosine or cytosine, respectively, in a nucleic acid target gene molecule; to determine the ratio of methylated nucleic acid target gene molecule relative to unmethylated nucleic acid target gene molecule in a sample, to determine the ratio of methylated nucleotide at a particular nucleotide locus on a nucleic acid target gene molecule relative to unmethylated nucleotide at that locus, and to provide redundant information to further confirm any of the determinations provided herein.

Disease-Related Discovery

In one embodiment, presence or absence of one or more methylated or unmethylated nucleotides may be identified as indicative of a disease state associated with methylated or unmethylated DNA, such as a neoplastic disease. In another embodiment, presence or absence of one or more methylated or unmethylated nucleotides may be identified as indicative of a normal, healthy or disease free state. In another embodiment, an abnormal ratio of methylated nucleic acid target gene molecules relative to unmethylated nucleic acid target gene molecules in a sample may be indicative of a disease state associated with methylated or unmethylated DNA, such as a neoplastic disease. For example, a relatively high number or a relatively low number of methylated nucleic acid target gene molecules compared to the relative amount in a normal individual may be indicative of a disease state associated with methylated or unmethylated DNA, such as a neoplastic disease. In another embodiment, an abnormal ratio of methylated nucleotide at a nucleotide locus relative to unmethylated nucleotide at a nucleotide locus in a nucleic acid target gene molecule can be indicative of a disease state associated with methylated or unmethylated DNA, such as a neoplastic disease. For example, a relatively high number or a relatively low number of methylated nucleotide loci compared to the relative amount in a normal individual can be indicative of a disease state associated with methylated or unmethylated DNA, such as a neoplastic disease.

Diseases associated with a modification of the methylation of one or more nucleotides include, for example: leukemia (Aoki E. et al., "Methylation status of the p15INK4B gene in hematopoietic progenitors and peripheral blood cells in myelodysplastic syndromes", *Leukemia* 14(4):586-593

(2000); Nosaka, K. et al., "Increasing methylation of the CDKN2A gene is associated with the progression of adult T-cell leukemia", *Cancer Res.* 60(4):1043-1048 (2000); Asimakopoulos F A et al., "ABL 1 methylation is a distinct molecular event associated with clonal evolution of chronic myeloid leukemia" *Blood* 94(7):2452-2460 (1999); Fajkusova L. et al., "Detailed Mapping of Methylcytosine Positions at the CpG Island Surrounding the Pa Promoter at the bcr-abl Locus in CML Patients and in Two Cell Lines, K562 and BV173" *Blood Cells Mol. Dis.* 26(3):193-204 (2000); Litz C. E. et al., "Methylation status of the major breakpoint cluster region in Philadelphia chromosome negative leukemias" *Leukemia* 6(1):35-41 (1992)), head and neck cancer (Sanchez-Cespedes M. et al. "Gene promoter hypermethylation in tumors and serum of head and neck cancer patients" *Cancer Res.* 60(4):892-895 (2000)), Hodgkin's disease (Garcia J. F. et al. "Loss of p16 protein expression associated with methylation of the p16INK4A gene is a frequent finding in Hodgkin's disease", *Lab Invest.* 79(12): 1453-1459 (1999)), gastric cancer (Yanagisawa Y. et al., "Methylation of the hMLH1 promoter in familial gastric cancer with microsatellite instability", *Int. J. Cancer* 85(1):50-53 (2000)), prostate cancer (Rennie P. S. et al., "Epigenetic mechanisms for progression of prostate cancer" *Cancer Metastasis Rev.* 17(4):401-409 (1998-99)), renal cancer (Clifford, S. C. et al., "Inactivation of the von Hippel-Lindau (VHL) tumor suppressor gene and allelic losses at chromosome arm 3p in primary renal cell carcinoma: evidence for a VHL-independent pathway in clear cell renal tumourigenesis" *Genes Chromosomes Cancer* 22(3):200-209 (1998), bladder cancer (Sardi, I. et al., "Molecular genetic alterations of c-myc oncogene in superficial and locally advanced bladder cancer" *Eur. Urol.* 33(4):424-430 (1998), breast cancer (Mancini, D. N. et al., "CpG methylation within the 5' regulatory region of the BRCAI gene is tumor specific and includes a putative CREB binding site" *Oncogene* 16(9): 1161-1169 (1998); Zrihan-Licht S. et al., "DNA methylation status of the MUC1 gene coding for a breast-cancer-associated protein" *Int. J. Cancer* 62(3):245-251 (1995); Kass, D. H. et al., "Examination of DNA methylation of chromosomal hot spots associated with breast cancer", *Anticancer Res.* 13(5A):1245-1251 (1993)), Burkitt's lymphoma (Tao, Q. et al., "Epstein-Barr virus (EBV) in endemic Burkitt's lymphoma: molecularanalysis of primary tumor tissue" *Blood* 91(4):1371-1381 (1998)), Wilms tumor (Kleymenova, E. V. et al., "Identification of a tumor-specific methylation site in the Wilms tumor suppressor gene" *Oncogene* 16(6):713-720 (1998)), Prader-Willi/Angelman syndrome (Zeschnigh et al. "Imprinted segments in the human genome: different DNA methylation patterns in the Prader-Willi/Angelman syndrome region as determined by the genomic sequencing method" *Human Mol. Genetics* (6)3:387-395 (1997); Fang P. et al., "The spectrum of mutations in UBE3A causing Angelman syndrome" *Human Mol. Genetics* 80:129-135 (1999)), ICF syndrome (Tuck-Muller et al., "CMDNA hypomethylation and unusual chromosome instability in cell lines from ICF syndrome patients" *Cytogenet Cell Genet.* 89(1-2):121-128 (2000)), dermatofibroma (Chen, T. C. et al., "Dermatofibroma is a clonal proliferative disease" *J. Cutan Pathol* 27(1): 36-39 (2000)), hypertension (Lee, S. D. et al., "Monoclonal endothelial cell proliferation is present in primary but not secondary pulmonary hypertension" *J. Clin. Invest.* 101(5): 927-934 (1998)), pediatric neurological disorders (Campos-Castello, J. et al., "The phenomenon of genomic "imprinting" and its implications in clinical neuropediatrics" *Rev. Neurol.* 28(1):69-73 (1999)), autism (Klauck, S. M. et al., "Molecular genetic analysis of the FMR-1 gene in a large collection of autistic patients" *Hum Genet* 100(2):224-229 (1997)), ulcerative colitis (Gloria, L. et al., "DNA hypomethylation and proliferative activity are increased in the rectal mucosa of patients with long-standing ulcerative colitis" *Cancer* 78(11): 2300-2306 (1996)), fragile X syndrome (Hornstra, I. K. et al., "High resolution methylation analysis of the FMR1 gene trinucleotide repeat region in fragile X syndrome" *Human Mol. Geneics* 2(10):1659-1665 (1993)), and Huntington's disease (Ferluga, J. et al., "Possible organ and age-related epigenetic factors in Huntington's disease and colorectal carcinoma", *Med. Hypotheses* 29(1):51-54 (1998)). Additional disease associated with the epigenetic state of DNA include low grade astrocytoma, anaplastic astrocytoma, glioblastoma, medulloblastoma, colon cancer, lung cancer, pancreatic cancer, endometrial cancer, neuroblastoma, headaches, sexual malfunction, primary myxedema, pernicious anemia, Addison's disease, myasthenia gravis, juvenile diabetes, idiopathic thrombocytopenic purpura, multiple sclerosis, rheumatoid arthritis, scleroderma, and other disorders such as CNS malfunctions, damage or disease, symptoms of aggression or behavioral disturbances, clinical, psychological and social consequences of brain damage, psychotic disturbances and personality disorders, dementia and/or associated syndromes, cardiovascular disease, malfunction and damage, malfunction, damage or disease of the gastrointestinal tract, malfunction, damage or disease of the respiratory system, lesion, inflammation, infection, immunity and/or convalescence, malfunction, damage or disease of the body as an abnormality in the developmental process, malfunction, damage or disease of the skin, the muscles, the connective tissue or the bones, endocrine and metabolic malfunction, damage or disease, and also can be associated with undesired drug interactions.

Disease-Related Analysis

Increased or decreased levels of methylation have been associated with a variety of diseases. Methylation or lack of methylation at defined positions can be associated with a disease or a disease-free state. The methods disclosed herein can be used in methods of determining the propensity of a subject to disease, diagnosing a disease, and determining a treatment regimen for a subject having a disease.

The methylation state of a variety of nucleotide loci and/or nucleic acid regions are known to be correlated with a disease, disease outcome, and success of treatment of a disease, and also may be used to distinguish disease types that are difficult to distinguish according to the symptoms, histologic samples or blood or serum samples. For example, CpG island methylator indicator phenotype (CIMP) is present in some types of ovarian carcinomas, but not in other types (Strathdee, et al., *Am. J. Pathol.* 158:1121-1127 (2001)). In another example, methylation may be used to distinguish between a carcinoid tumor and a pancreatic endocrine tumor, which may have different expected outcomes and disease treatment regimens (Chan et al., *Oncogene* 22:924-934 (2003)). In another example, *H. pylori* dependent gastric mucosa associated lymphoid tissue (MALT) lymphomas are characterized as having several methylated nucleic acid regions, while those nucleic acid regions in *H. pylori* independent MALT lymphomas are not methylated Kaneko et al., *Gut* 52:641-646 (2003)). Similar relationships with disease, disease outcome and disease treatment have been correlated with hypomethylation or unmethylated nucleic acid regions or unmethylated nucleotide loci.

Methods related to the disease state of a subject may be performed by collecting a sample from a subject, treating the sample with a reagent that modifies a nucleic acid target gene molecule sequence as a function of the methylation state of the nucleic acid target gene molecule, subjecting the sample to methylation specific amplification, then detecting one or more fragments that are associated with a disease or that are associated with a disease-free state. In another embodiment, the fragments are detected by measuring the mass of the nucleic acid target gene molecule or nucleic acid target gene molecule fragments. Detection of a nucleic acid target gene molecule or nucleic acid target gene molecule fragment can identify the methylation state of a nucleic acid target gene molecule or the methylation state of one or more nucleotide loci of a nucleic acid target gene molecule. Identification of the methylation state of a nucleic acid target gene molecule or the methylation state of one or more nucleotide loci of a nucleic acid target gene molecule can indicate the propensity of the subject toward one or more diseases, the disease state of a subject, or an appropriate or inappropriate course of disease treatment or management for a subject.

Combinations and Kits

In another embodiment, there are provided diagnostic systems, typically in combination or kit form, containing a reagent that modifies one or more nucleotides of the nucleic acid target gene molecule as a function of the methylation state of the nucleic acid target gene molecule, such as bisulfite; one or more methylation specific primers for specifically hybridizing to a reagent-treated nucleic acid target gene molecule, such as one or more methylation specific PCR primers; and one or more compounds for fragmenting amplified nucleic acid target gene molecule, such as RNases, including RNase A or RNase T1. A kit also may include the appropriate buffers and solutions for performing the methylation identification methods described herein. For example, a kit can include a glass vial used to contain milligram quantities of a primer or enzyme. A kit also may include substrates, supports or containers for performing the methylation identification methods, including vials or tubes, or a mass spectrometry substrate such as a Sequenom SpectroCHIP substrate.

EXAMPLES

Example 1

Bisulfite Treatment of a Nucleic Acid Target Gene Region

The protocol disclosed by Paulin, R. et al. in *Nucleic Acids Res.* 26:5009-5010, 1998 was utilized for bisulfite treatment of the nucleic acid target gene region. Briefly, in this protocol 2 ug of genomic DNA is digested with a restriction endonuclease (EcoR1), then denatured by the addition of 3 M sodium hydroxide and incubated for 15 min at 37° C. A 6.24 M urea/2 M sodium metabisulfite (4 M bisulfite) solution is prepared and added with 10 mM hydroquinone to the denatured DNA. The corresponding final concentrations are 5.36 M, 3.44 M and 0.5 mM respectively. The reaction is performed in a 0.5 ml tube overlaid with mineral oil. This reaction mix is repeatedly heated between 55° C. for 15 min and 95° C. for 30 s in a PCR machine (MJ Tetrad) for 20 cycles. DNA purification was done using the commercially available GENECLEAN kit from Q-biogene.

Example 2

PCR and In Vitro Transcription of a Nucleic Acid Target Gene Region

The IGF2/H19 region (Human Genome Chromosome 11:1,983,678-1,984,097) was PCR-amplified from bisulfite treated human genomic DNA using primers that incorporate the T7 [5'-CAG TAA TAC GAC TCA CTA TAG GGA GA] promoter sequence. Two sets of primers were designed to incorporate the T7 promoter sequence either to the forward (5'-CAG TAA TAC GAC TCA CTA TAG GGA GAA GGC TGT TAG TTT TTA TTT TAT TTT TAA T-3'; 5'-AGG AAG AGA GAA CCA CTA TCT CCC CTC AAA AAA-3') or to the reverse (5'-AGG AAG AGA GGT TAG TTT TTA TTT TAT TTT TAA T-3'; 5'-CAG TAA TAC GAC TCA CTA TAG GGA GAA GGC TAA CCA CTA TCT CCC CTC AAA AAA-3') strand. Alternatively we cloned the derived PCR product into a pGEM-T vector system (Promega, Madison, Wis.) and re-amplified from the cloned DNA. The PCR reactions were carried out in a total volume of 5 µl using 1 pmol of each primer, 40 µM dNTP, 0.1 U Hot Star Taq DNA polymerase (Qiagen, Valencia, Calif.), 1.5 mM $MgCl_2$ and buffer supplied with the enzyme (final concentration 1×). The reaction mix was pre-activated for 15 min at 95° C. The reactions were amplified in 45 cycles of 95° C. for 20 s, 62° C. for 30 s and 72° C. for 30 s followed by 72° C. for 3 min. Unincorporated dNTPs were dephosphorylated by adding 1.7 ul H2O and 0.3 U Shrimp Alkaline Phosphatase. The reaction was incubated at 37° C. for 20 min and SAP was then heat-inactivated for 10 minutes at 85° C.

Typically, two microliter of the PCR reaction were directly used as template in a 4-µl transcription reaction. 20 units of T7 R&DNA polymerase (Epicentre, Madison, Wis.) were used to incorporate either dCTP or dTTP in the transcripts. Ribonucleotides were used at 1 mM and the dNTP substrate at 2.5 mM; other components in the reaction were as recommended by the supplier. Following the in vitro transcription RNase A was added to cleave the in vitro transcript. The mixture was then further diluted with $H_2O$ to a final volume of 27 µl. Conditioning of the phosphate backbone prior to MALDI-TOF MS was achieved by the addition of 6 mg CLEAN Resin (Sequenom Inc., San Diego, Calif.). Further experimental details have been described elsewhere (ref. 29).

Example 3

Mass Spectral Measurements of Transcribed Nucleic Acid Target Gene Region

Conditioning of the phosphate backbone is achieved by the addition of 6 mg CLEAN Resin (Sequenom Inc., San Diego, Calif.) to the transcription sample. A 15 nl aliquot of the cleavage reaction is robotically dispensed onto a silicon chip preloaded with matrix (SpectroCHIP; Sequenom Inc., San Diego, Calif. Mass spectra are collected using a MassARRAY mass spectrometer (Bruker-SEQUENOM).

Example 4

Identification of Methylation Sites in IGF2/H19

The difference in the mass spectra results from a C-specific cleavage reaction of the forward transcript may be seen in FIG. 1. The mass spectrum derived from the methylated template shows signals corresponding to the expected methylation sites. In this spectra each mass signal represents at least two CpG sites (cleavage at the beginning of the fragment and at the end) and two cleavage products therefore represent each methylated CpG site. The non-methylated template creates a mass spectrum that is devoid of any sequence/methylation associated signals. FIG. 1(A) displays mass signals generated by cytosine specific cleavage of the forward transcript of the IGF2/H19 region (upper spectral analysis is the methylated template; lower spectral analysis is the non-methylated template). Methylation of the target sequence results in the generation of rCTP-containing transcripts; every methylated CpG is represented in the transcript by a cleavage site. Each of the cleavage products is labeled with a number, which indicates the CpG position in the template. These numbers can be cross-referenced with the cleavage products listed in FIG. 1(B). The non-methylated target sequence does not contain cytosine and therefore does not contain cleavage sites. Mass signals are labeled with letters and the corresponding explanations are listed in FIG. 1(B). A full list of expected cleavage products illustrates the predicted difference between methylated and non-methylated template. Predicted mass signals 12 and 13 are not found in the experimental spectrum, because the corresponding CpGs 23 and 24 are not methylated.

All masses below 1300 Da cannot be detected reliably in the chosen mass window. The mass signal labeled A is a doubly charged molecular ion E. Mass signals labeled B and D represent so called abortive cycling products. Mass signals labeled C and E are expected main signals generated by cleavage of the transcription product.

The reactions described above provide ideal mass signal patterns that are well suited to identify methylation in mixtures that contain methylated DNA in a fraction as low as 5%, without selective PCR amplification. FIG. 2 is an overlay of mass signal patterns generated by cytosine specific cleavage of the forward transcript of the IGF2/H19 region. In the depicted case, the template used for PCR amplification consisted of a mixture of methylated and non-methylated DNA. Mass spectra reveal increasing signal intensity of cleavage products with increasing amount of methylated template DNA. Methylation specific mass signals can be detected in mixtures containing as little as 5% methylated DNA.

Example 5

Statistical Methods

Base-specific cleavage reactions also can be used in determination of methylation ratios. For example, methylation induced C/T changes on the forward strand are represented as G/A changes on the complementary strand. These changes lead to a mass shift of 16 Da (G/A mass shift) or multiples thereof, when multiple CpGs are enclosed in one cleavage product. In reactions where methylation results in a mass shift of nucleic acid target gene molecule fragments, one fragment represents the methylated template and a second fragment represents the non-methylated template. The intensities of the measured masses of these fragments can be compared to determine the ratio of methylated vs. non-methylated nucleic acid target gene molecules. Also, the base composition of the measured fragments differs only by one or a few nucleotides, which assures equal desorption and ionization behavior during MALDI-TOF measurement. Methods for intensity estimation of mass measurements such as "area-under the peak" and "signal to noise" can yield similar results. Depending on the sequence of the nucleic acid target gene molecule, multiple signal pairs can be used in determining the ratio between signal intensities. This information can be used to assess the degree of methylation for each CpG site independently, or, if all CpG sites are methylated approximately to the same degree, to average the methylation content over the complete target region. A direct correlation between signal intensity ratios and the ratio of the deployed DNAs can be determined for ranges of 10%-90% of methylated template. If the ratio between methylated and non-methylated template is below 10% or exceeds 90%, the signals that represent the lower amount of template can still be detected, but the quantitation can be subject to higher error.

Relative methylation was compared between normal and tumor samples using the Wilcoxon signed-rank test, a non-parametric counterpart of the paired t-test. The two-way cluster analysis clustered tissue samples and CpG fragments based on Euclidean distances and complete linkage clusters (Kauffman, L. and P. J. Rouseeuw, Finding Groups in Data: An Introduction to Cluster Analysis, 1990 Wiley New York. p.xiv, 342). This was carried out using a modified version of the heatmap.2 function of the gregmisc package using the R statistical environment (R Development Core Team, R:A language and environment for Statistical Computing, 2003). The tree-based classifier was found using the recursive partitioning package rpart in R.

Example 6

Methylation Ratio Analysis

Determination of methylation ratios is enabled by a different base-specific cleavage reaction. Methylation induced C/T changes on the forward strand are represented as G/A changes on the reverse strand. Since we restricted our cleavage schemes to C- and T-specific cleavage, methylation events lead to a mass shift of 16 Da (G/A mass shift) or a multitude thereof when multiple CpGs are enclosed in one cleavage product. The signal pair shown in FIG. 3 demonstrates this. FIG. 3 is an overlay of mass spectra generated by uracil specific cleavage of the reverse transcript of the IGF2/H19 region. Cleavage products derived from the methylated template contain rGTP at every position where the Cytosine of the forward strand was methylated. In contrast, the bisulfite conversion of non-methylated Cytosine to Uracile results in incorporation of rATP on the reverse strand. This 16d difference between rGTP and rATP, or a multitude thereof when several CpGs are embedded in one cleavage product, can be detected unambiguously. The calculation of the area under the curve of mass signals specific for methylated and non-methylated template can be used to determine the ratio between methylated and non-methylated DNA used for amplification.

The cleavage product derived from the non-methylated template (CGCAACCACT) is detected at 3132 Da while its equivalent derived from the methylated template (CACAACCACT) can be found at 3148 Da.

Reactions where one signal represents the methylated template and a second signal represents the non-methylated template can be used to determine the ratio of methylated vs. non-methylated template by comparing their signal intensities. The nucleotide composition of the measured fragments differs only by a single nucleotide, which ensures equivalent desorption and ionization behavior during MALDI-TOF measurement. Depending on the reference sequence of the target region, multiple signal pairs are available for determining the ratio between signal intensities. This information can be used to assess the degree of methylation for each CpG site independently or, if all CpG sites are methylated approximately to the same degree, to average the methylation content over the complete target region.

A direct correlation can be seen between signal intensity ratios and the ratio of the deployed DNAs. The span of linearity of this correlation ranged from 10%-90% of methylated template. The average standard deviation of the investigated concentrations was approximately 3%, with higher standard deviations towards both ends of the scale. If the ratio between methylated and non-methylated template is below 10% or exceeds 90%, the signals that are representing the lower amount of template can still be detected, but the intensity of signal does not correlate exactly to the actual ratio anymore.

Example 7

Methylation Pattern Analysis of IGF2/H19

The capability of base specific cleavage to determine the methylation status of each and every CpG within a given target region was determined. As outlined above, the C-specific forward reaction incorporates a cleavage nucleotide for each methylated CpG within the amplicon. The resulting cleavage products represent the existence of two cleavage nucleotides (exception: first and last fragment) or in this case two methylated Cs. Given the current limitations of MALDI-TOF instrumentation, a practical mass window ranges from around 1000 Da to 10000 Da. In this mass window, cleavage products with a length around 4 to 30 nucleotides can be detected. When the distance between two methylated Cytosines becomes smaller or larger than this range, the resulting mass of the cleavage product might be too high or too low to be detected under standard conditions. The analysis of a single reaction still allows determining the methylation status of approximately 75% (depending on the reference sequence) of all CpG sites within the amplified nucleic acid molecule. To obtain information about all CpG sites, a set of four reactions were performed: C- and T-specific cleavage of the forward and reverse transcription product. This combination enables base-specific cleavage after each nucleotide (C-specific cleavage on the reverse strand equals G-specific cleavage on the forward strand; T-specific cleavage on the reverse strand equals A-specific cleavage on the forward strand). The combined information from these four cleavage reactions allows compilation of the exact methylation pattern. For the IGF2/H19 region described here, two reactions were sufficient to obtain the methylation status for each CpG site. However using four reactions provides the advantage of information redundancy. In this system 92% of all CpG sites were represented by more than one signal. This means that each methylation event is independently confirmed by more than one observation in one or more reactions. This redundancy is an important aspect in potential diagnostic use. FIG. 4 is a mass spectra representing all four base-specific cleavage reactions of the IGF/H19 amplicon. Numbers correspond to the CpG positions within this target region. Arrows point at the mass signals that indicate the presence of a methylated cytosine at the marked position. All methylated CpG's in the selected region were identified by one or more mass signals. Approximately 75% were identified by more than two mass signals.

The methylation pattern of the IGF2/H19 imprinted region in adult blood samples confirmed the segregation into methylated and non-methylated template strands reported by Vu et al. (*Genomics* 64(2):p. 29331-40, 1999). Out of the 24 clones we analyzed, 13 (54%) could be identified as methylated and 11 (46%) as non-methylated. No sequence changes were observed. Vu et al. (supra) showed by dideoxy sequencing of bisulfite treated DNA that 25 out of the 26 CpG sites within the amplicon are methylated. The only non-methylated CpG was found at position 470. Our results indicated a slightly different methylation pattern in the studied sample DNA, where all CpG sites were methylated. Our data also confirmed methylation of the CpNpG site at position 347. Due to the variability in individual methylation patterns, which have been observed by other authors, minor differences are anticipated.

The results demonstrate the capability of the method to discriminate methylated and non-methylated DNA nucleic acid target gene regions simultaneously and to reconstruct the exact methylation pattern. In order to support this contention, we analyzed bisulfite treated genomic DNA directly. The produced mass signal spectra showed signal patterns that are representative for the methylated template as well as those that are characteristic for the non-methylated template. The signal intensities for methylation-specific signals and non-methylation-specific signals were compared and the 50/50 ratio expected for hemi-methylated DNA, as in control blood samples, was confirmed. FIG. 5 is a mass Spectra generated by uracil specific cleavage of the reverse transcript of the IGF2/H19 region. Genomic DNA was used for amplification. Dotted lines mark the position of mass signals representing non-methylated CpG's. Signals with 16 Da shift (or a multitude thereof) represent methylation events. The area-under-the-curve ratio of methylated versus non-methylated template approximates to 1, as one expects for hemi-methylated nucleic acid target gene regions. This indicates an unbiased amplification of methylated and non-methylated template for the analyzed region and validates our semi-quantitative capabilities.

Example 8

Analysis of Methylation in Lung Cancer Biopsies

The degree of methylation of 11 promoter regions in 48 smoker-derived lung tumors, non-small cell lung cancer (NSCLC) and adjacent normal specimens. The patient collection consists of 22 females and 26 males, ages 45 to 83 years (median 68), 24 adenocarcinomas and 24 squamous cell carcinomas. The TNM Staging included 22 stage two, 16 stage three, and 10 stage four. DNA was extracted following a standard phenol/chloroform protocol. The analysis included the promoter regions of 47 genes that contain a total of 1426 CpG positions. Methylation status and quantitative assessment of the relative methylation was carried out for each CpG position according to the protocol described above. Of the 47 promoter regions analyzed, 11 were identified where the average relative methylation difference between normal and tumor tissues was greater than 10%.

The results of these 11 regions possessing 194 CpG positions measured were analyzed on 111 fragments. Two fragments showed no methylation (relative methylation=0). Of the remaining 109 fragments, 85 showed statistically significant relative methylation differences between normal and tumor tissues at the 0.05 level, 34 were significant at the $10^{-4}$ level, and 8 were significant at the $10^{-6}$ level. To explore the similarities and differences among tissue samples and CpG fragments, we carried out a two-way hierarchical cluster analysis (FIG. 6). The tissue samples formed two distinct clusters separating the normal from the tumor tissues. This result supports the hypothesis that the relative amount of methylated DNA can be used to differentiate between normal and neoplastic tissue.

The usefulness of the methylation ratio data was analyzed for classification using a tree-based procedure. The algorithm identified a decision tree with 5 nodes and 6 leaves. 94% of all samples were identified correctly with a misclassification rate for the remaining samples of 6% (see FIG. 7). Fragment 9 from SERPINB5 was the single-most important methylation site, providing over 90% classification accuracy.

Discussion

The interest in genomic methylation has fueled the development of several methods for assessment of cytosine methylation. Many of these techniques can only analyze a restricted set of CpG sites in their target regions and have to extrapolate the methylation status to the whole region (Cobra, MSP, restriction techniques, primer extension, PNA-MALDI TOF, Methylight and others). Issues with misinterpretation of the methylation status have been reported. Of particular importance are complications that arise for those methods restricted to selected CpGs specifically when their methylation within the examined genomic region is inconsistent. Other techniques assess several CpG sites at once by simultaneous hybridization of multiple oligonucleotides (e.g. Microarray, Primer extension) to amplification products of bisulfite treated DNA. Hybridization based techniques for methylation analyses are compromised by the effect of the bisulfite treatment. The degenerated nucleic acid code (reduction from four to mainly three bases) decreases the specificity of hybridization oligos. Due to the high density of CpG sites within CpG rich regions, the oligo length cannot be elongated arbitrarily without the incorporation of ambiguous bases (C/T).

The methods of the present invention provide a novel approach for DNA methylation analysis that employs base specific cleavage and MALDI-TOF analysis to overcome these limitations. Using a combination of four base specific cleavage reactions each CpG of a target region can be assessed individually and is represented by multiple indicative mass signals. The acquired information about the methylation status of the examined region is based on numerous independent observations. The redundancy of this information can be leveraged to achieve higher confidence in qualitative analysis, and to obtain highly accurate averages in quantitative analysis with small standard deviations. The present methods may be customized to meet individual needs in DNA methylation analysis: discovery of methylation in large stretches of genomic DNA with a single cleavage reaction; methylation ratio analysis, where fractions of methylated DNA are as low as 5% may be detected in mixtures of methylated and non-methylated template; methylation pattern analysis, where the methylation status of each CpG within a target region can be determined as a group or independently.

The general applicability of these methods have been demonstrated by reconstructing the described methylation sites for IGF2/H19 using cloned DNA as well as genomic DNA. The semi-quantitative assessment of methylation in larger target regions spanning multiple CpG sites was demonstrated and was able to accurately analyze methylation down to ratio's of approximately 5%. The large-scale analysis of methylation in NSCLC is a first implementation of the method for quantitative assessment of methylation ratios in a high-throughput format. Initial analysis of methylation ratios in a subset of 11 genes allowed unsupervised clustering of samples according to their histological status and enabled a classification of samples with a substantially lower misclassification rate than previous methods.

We claim:

1. A method for determining the susceptibility of a human subject to lung cancer, which comprises:
   a. identifying the methylation state of SerpinB5 methylation sites in a nucleic acid from the human subject by a process that comprises (i) amplifying the nucleic acid with polynucleotide primers having nucleotide sequences
   TGGAGGTTTTTTGGAAGTTGTGTAG (SEQ ID NO: 30) and
   AAAAAATCACCAACCCTACTACCCC (SEQ ID NO: 78)
   thereby generating an amplification product, and (ii) assessing the methylation sites in the amplification product; and
   b. determining the susceptibility of the subject to lung cancer based on the methylation state identified in (a).

2. The method of claim 1, wherein the nucleic acid is contacted with a reagent that modifies unmethylated cytosine to produce uracil.

3. The method of claim 2, wherein the reagent is bisulfite.

4. The method of claim 2, wherein the nucleic acid is amplified after it is contacted with the reagent.

5. The method of claim 4, wherein the sequence of the amplification product is determined.

6. The method of claim 1, wherein the methylation state is the percentage of methylated nucleotides in the nucleic acid.

7. A method for confirming the diagnosis of lung cancer in a human subject, which comprises:
   a. determining the methylation state of SerpinB5 methylation sites in a nucleic acid from a human subject diagnosed with lung cancer by a process that comprises (i) amplifying the nucleic acid with polynucleotide primers having nucleotide sequences
   TGGAGGTTTTTTGGAAGTTGTGTAG (SEQ ID NO: 30) and
   AAAAAATCACCAACCCTACTACCCC (SEQ ID NO: 78)
   thereby generating an amplification product, and (ii) assessing the methylation sites in the amplification product; and b. confirming the diagnosis of lung cancer based on the methylation state determined in (a).

8. The method of claim 7, wherein the nucleic acid is contacted with a reagent that modifies unmethylated cytosine to produce uracil.

9. The method of claim 8, wherein the reagent is bisulfite.

10. The method of claim 8, wherein the nucleic acid is amplified after it is contacted with the reagent.

11. The method of claim 10, wherein the sequence of the amplification product is determined.

12. The method of claim 7, wherein the methylation state is the percentage of methylated nucleotides in the nucleic acid.

* * * * *

SEQUENCE LISTING

```
<160> NUMBER OF SEQ ID NOS: 104

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
ttgttgattt atttgggaag ttggtt                                          26

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
gttaggaatg tggttttggg gatt                                            24

<210> SEQ ID NO 3
<211> LENGTH: 24
<212> TYPE: DNA
<213> ORGANISM: Artificial Sequence
<220> FEATURE:
<223> OTHER INFORMATION: Primer
```

<400> SEQUENCE: 3
gttggtttgg gggtttttga ttag                                    24

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
tgttttttaa attttttgga gggat                                   25

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5 gttgttttttt ggttgttttt tt                                     22

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ggatttgtag gttgggttt tttt                                     24

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7 ttgttttgg ggttttgttt ttatttt                                  27

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
ggtagtggtt ttgaggagta agaga                                   25

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
ggggtttgaa gattttgttt tgttttat                                28

<210> SEQ ID NO 10

```
<211> LENGTH: 30
<212> TYPE: DNA
<213> ORGANISM: Artificial Sequence
<220> FEATURE:
<223> OTHER INFORMATION: Primer

<400> SEQUENCE: 10 ggagggggagt ttatttattt ttttaatttt                                30

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
ggagttggga attttaaggt aggtga                                     26

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
agggttagag taagagaggg ttttgga                                    27

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
gggtttgttt ttagaagaga aaatgg                                     26

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
gggttttgat ttgattttt gttatag                                     27

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
agggaagaag tgattttggt tgatg                                      25

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
```
tttaaggagg gttgagggtt tttaag                                          26

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
atatttttgg aaaaaggaga gtggg                                           25

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
ttggtgatag ttaggtaggt ggaagttt                                        28

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
ttttggtttg aggggttgt attta                                            25

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
gaggttttta gttttatttg taggt                                           25

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
gaaagggttt ggaaagttaa aagtattg                                        28

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
ttgggtaaat tttaagatt gttttta                                          28

<210> SEQ ID NO 23
<211> LENGTH: 25
<212> TYPE: DNA

```
<213> ORGANISM: Artificial Sequence
<220> FEATURE:
<223> OTHER INFORMATION: Primer

<400> SEQUENCE: 23 gggattttttt gtgtggtgtt gatag                                    25

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
tgggaagtta aggtaggtgg attattt                                   27

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
tttgtttttg gttgggtaat ttttg                                     25

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
ggtttgtagt tggtttggag gttt                                      24

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
gggatttggg aaggagtata ggatag                                    26

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
gtatagaggg gtgtggtgtt ttttg                                     25

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
tttgtttttg ttgtagttgt tgttgtt                                   27
```

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
tggaggtttt ttggaagttg tgtag                                     25

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
gggatttttt gtattggggt aggtt                                     25

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
ttgttttggg attgttgttg ttttg                                     25

<210> SEQ ID NO 33
<211> LENGTH: 26
<212> TYPE: DNA
<213> ORGANISM: Artificial Sequence
<220> FEATURE:
<223> OTHER INFORMATION: Primer

<400> SEQUENCE: 33
ttggggtttt ttgagagtag gtaggt                                    26

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
gggagttgta gtttagttag ttagggagta                                30

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
ggttgggagt tttgataagg ggtat                                     25

<210> SEQ ID NO 36
<211> LENGTH: 30
<212> TYPE: DNA
<213> ORGANISM: Artificial Sequence
<220> FEATURE:

```
<223> OTHER INFORMATION: Primer

<400> SEQUENCE: 36
tggagtgggt aagattattg taagtatgat                                    30

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
ggtttttgag tttgtaagaa gtgga                                         25

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
gggtgttttt tggtagagag gtttt                                         25

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
ggtttttggg tttttagagt tttt                                          24

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
ttgtagtttt tttagttagg gttgtttt                                      28

<210> SEQ ID NO 41
<211> LENGTH: 26
<212> TYPE: DNA
<213> ORGANISM: Artificial Sequence
<220> FEATURE:
<223> OTHER INFORMATION: Primer

<400> SEQUENCE: 41
tatttagagg aggttttgtgt ggtgtg                                       26

<210> SEQ ID NO 42
<211> LENGTH: 25
<212> TYPE: DNA
<213> ORGANISM: Artificial Sequence
<220> FEATURE:
<223> OTHER INFORMATION: Primer

<400> SEQUENCE: 42
ttttgaggta gagggtgagg agtag                                         25
```

```
<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
attgaggagg ttgaggagtg tattg                                          25

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
ggtttgagag attagtgttt tagatgttta                                     30

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
gggaggttgg agtttagtag tag                                            23

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
gggagggaaa ttatggtttt ttttg                                          25

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
gtgagggtgg ttttaaagag attag                                          25

<210> SEQ ID NO 48
<211> LENGTH: 29
<212> TYPE: DNA
<213> ORGANISM: Artificial Sequence
<220> FEATURE:
<223> OTHER INFORMATION: Primer

<400> SEQUENCE: 48
aggctgttag tttttatttt atttttaat                                      29

<210> SEQ ID NO 49
<211> LENGTH: 25
<212> TYPE: DNA
<213> ORGANISM: Artificial Sequence
<220> FEATURE:
<223> OTHER INFORMATION: Primer
```

```
<400> SEQUENCE: 49
aaactaaaaa ctctctcctc ctccc                                          25

<210> SEQ ID NO 50
<211> LENGTH: 26
<212> TYPE: DNA
<213> ORGANISM: Artificial Sequence
<220> FEATURE:
<223> OTHER INFORMATION: Primer

<400> SEQUENCE: 50
tcaatctcca atc cttttaa aaaaaa                                        26

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
ccttttccta tcacaaaaat aatcc                                          25

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
aaaaaaaacc atactttccc tataacacca                                     30

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
atccctacac ccaaatttcc attac                                          25

<210> SEQ ID NO 54
<211> LENGTH: 26
<212> TYPE: DNA
<213> ORGANISM: Artificial Sequence
<220> FEATURE:
<223> OTHER INFORMATION: Primer

<400> SEQUENCE: 54
caatcaaatt tccaaatctt aattcc                                         26

<210> SEQ ID NO 55
<211> LENGTH: 27
<212> TYPE: DNA
<213> ORGANISM: Artificial Sequence
<220> FEATURE:
<223> OTHER INFORMATION: Primer

<400> SEQUENCE: 55
tcacctccaa atcaccaaac taatcta                                        27

<210> SEQ ID NO 56
<211> LENGTH: 25
```

```
<212> TYPE: DNA
<213> ORGANISM: Artificial Sequence
<220> FEATURE:
<223> OTHER INFORMATION: Primer

<400> SEQUENCE: 56
ccctccaaac tataaaccaa taaac                                              25

<210> SEQ ID NO 57
<211> LENGTH: 25
<212> TYPE: DNA
<213> ORGANISM: Artificial Sequence
<220> FEATURE:
<223> OTHER INFORMATION: Primer

<400> SEQUENCE: 57
tctacctaca acttccccca acaac                                              25

<210> SEQ ID NO 58
<211> LENGTH: 27
<212> TYPE: DNA
<213> ORGANISM: Artificial Sequence
<220> FEATURE:
<223> OTHER INFORMATION: Primer

<400> SEQUENCE: 58
acctcttaat cccctcccta ttatacc                                            27

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
cctccaaaac tacaactaac tcctc                                              25

<210> SEQ ID NO 60
<211> LENGTH: 26
<212> TYPE: DNA
<213> ORGANISM: Artificial Sequence
<220> FEATURE:
<223> OTHER INFORMATION: Primer

<400> SEQUENCE: 60
ttcatttcac aacttcaacc cctaaa                                             26

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
atcaaactca acaattcaac cttcc                                              25

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
```

-continued acaaaatcca attccacccc tac                                    23

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
actcctaacc tcaaataatc caccc                                  25

<210> SEQ ID NO 64
<211> LENGTH: 28
<212> TYPE: DNA
<213> ORGANISM: Artificial Sequence
<220> FEATURE:
<223> OTHER INFORMATION: Primer

<400> SEQUENCE: 64
caaaaatcta aaacaaccc aaactaaa                                28

<210> SEQ ID NO 65
<211> LENGTH: 26
<212> TYPE: DNA
<213> ORGANISM: Artificial Sequence
<220> FEATURE:
<223> OTHER INFORMATION: Primer

<400> SEQUENCE: 65
tcaaaaccct caccctaaaa actaac                                 26

<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66
cctcctctcc ctaaacccaa aataa                                  25

<210> SEQ ID NO 67
<211> LENGTH: 25
<212> TYPE: DNA
<213> ORGANISM: Artificial Sequence
<220> FEATURE:
<223> OTHER INFORMATION: Primer

<400> SEQUENCE: 67 aaaccctca catttctcca aacaa                                   25

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
aaaaactccc taactcaacc                                        20

<210> SEQ ID NO 69
<211> LENGTH: 25
<212> TYPE: DNA
<213> ORGANISM: Artificial Sequence

```
<220> FEATURE:
<223> OTHER INFORMATION: Primer

<400> SEQUENCE: 69
atcatcaata aacccatcc aaatc                                          25

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
cccaaaacat ccccaaactt atcta                                         25

<210> SEQ ID NO 71
<211> LENGTH: 28
<212> TYPE: DNA
<213> ORGANISM: Artificial Sequence
<220> FEATURE:
<223> OTHER INFORMATION: Primer

<400> SEQUENCE: 71
caaaaataaa aacatttccc aaaatcac                                      28

<210> SEQ ID NO 72
<211> LENGTH: 28
<212> TYPE: DNA
<213> ORGANISM: Artificial Sequence
<220> FEATURE:
<223> OTHER INFORMATION: Primer

<400> SEQUENCE: 72
actccctcat aaaattctca ccaatatc                                      28

<210> SEQ ID NO 73
<211> LENGTH: 24
<212> TYPE: DNA
<213> ORGANISM: Artificial Sequence
<220> FEATURE:
<223> OTHER INFORMATION: Primer

<400> SEQUENCE: 73 taatacccc tactaacccc aaac                                           24

<210> SEQ ID NO 74
<211> LENGTH: 27
<212> TYPE: DNA
<213> ORGANISM: Artificial Sequence
<220> FEATURE:
<223> OTHER INFORMATION: Primer

<400> SEQUENCE: 74
acttcctata aatccctaac tctcccc                                       27

<210> SEQ ID NO 75
<211> LENGTH: 26
<212> TYPE: DNA
<213> ORGANISM: Artificial Sequence
<220> FEATURE:
<223> OTHER INFORMATION: Primer

<400> SEQUENCE: 75
accctccttc ctccctaatt ataacc                                        26
```

<210> SEQ ID NO 76
<211> LENGTH: 25
<212> TYPE: DNA
<213> ORGANISM: Artificial Sequence
<220> FEATURE:
<223> OTHER INFORMATION: Primer

<400> SEQUENCE: 76
ctatcccaac ccttccctat taatc                                          25

<210> SEQ ID NO 77
<211> LENGTH: 25
<212> TYPE: DNA
<213> ORGANISM: Artificial Sequence
<220> FEATURE:
<223> OTHER INFORMATION: Primer

<400> SEQUENCE: 77
taaaattcct acctccaact ttccc                                          25

<210> SEQ ID NO 78
<211> LENGTH: 25
<212> TYPE: DNA
<213> ORGANISM: Artificial Sequence
<220> FEATURE:
<223> OTHER INFORMATION: Primer

<400> SEQUENCE: 78
aaaaaatcac caaccctact acccc                                          25

<210> SEQ ID NO 79
<211> LENGTH: 25
<212> TYPE: DNA
<213> ORGANISM: Artificial Sequence
<220> FEATURE:
<223> OTHER INFORMATION: Primer

<400> SEQUENCE: 79
accaaactcc ccaactatct ctctc                                          25

<210> SEQ ID NO 80
<211> LENGTH: 25
<212> TYPE: DNA
<213> ORGANISM: Artificial Sequence
<220> FEATURE:
<223> OTHER INFORMATION: Primer

<400> SEQUENCE: 80 acccttcct ccttaaccct ttatc                                           25

<210> SEQ ID NO 81
<211> LENGTH: 25
<212> TYPE: DNA
<213> ORGANISM: Artificial Sequence
<220> FEATURE:
<223> OTHER INFORMATION: Primer

<400> SEQUENCE: 81
aaaacaaacc aaacccatcc actaa                                          25

<210> SEQ ID NO 82
<211> LENGTH: 27
<212> TYPE: DNA
<213> ORGANISM: Artificial Sequence
<220> FEATURE:
<223> OTHER INFORMATION: Primer

<400> SEQUENCE: 82
tcaaaaccta aaacaaaca aaaaaaa                27

<210> SEQ ID NO 83
<211> LENGTH: 25
<212> TYPE: DNA
<213> ORGANISM: Artificial Sequence
<220> FEATURE:
<223> OTHER INFORMATION: Primer

<400> SEQUENCE: 83
accacaaaaa acaaaaccca aaaaa                 25

<210> SEQ ID NO 84
<211> LENGTH: 27
<212> TYPE: DNA
<213> ORGANISM: Artificial Sequence
<220> FEATURE:
<223> OTHER INFORMATION: Primer

<400> SEQUENCE: 84
taccaaaaaa accactctac aaaccta               27

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
aacaaccaca acctactcta tccc                  24

<210> SEQ ID NO 86
<211> LENGTH: 30
<212> TYPE: DNA
<213> ORGANISM: Artificial Sequence
<220> FEATURE:
<223> OTHER INFORMATION: Primer

<400> SEQUENCE: 86
cctttcttaa catttacaat cttcttaaac            30

<210> SEQ ID NO 87
<211> LENGTH: 30
<212> TYPE: DNA
<213> ORGANISM: Artificial Sequence
<220> FEATURE:
<223> OTHER INFORMATION: Primer

<400> SEQUENCE: 87
tcttcaatcc ttaaaaaaat acctatttct            30

<210> SEQ ID NO 88
<211> LENGTH: 26
<212> TYPE: DNA
<213> ORGANISM: Artificial Sequence
<220> FEATURE:
<223> OTHER INFORMATION: Primer

<400> SEQUENCE: 88
ccaaaaatct ctaaataccc ttctcc                26

<210> SEQ ID NO 89

```
<211> LENGTH: 26
<212> TYPE: DNA
<213> ORGANISM: Artificial Sequence
<220> FEATURE:
<223> OTHER INFORMATION: Primer

<400> SEQUENCE: 89
taaacaacaa ccccaatata acaacc                                          26

<210> SEQ ID NO 90
<211> LENGTH: 24
<212> TYPE: DNA
<213> ORGANISM: Artificial Sequence
<220> FEATURE:
<223> OTHER INFORMATION: Primer

<400> SEQUENCE: 90
cactaccaac aaacccaaac aaac                                            24

<210> SEQ ID NO 91
<211> LENGTH: 25
<212> TYPE: DNA
<213> ORGANISM: Artificial Sequence
<220> FEATURE:
<223> OTHER INFORMATION: Primer

<400> SEQUENCE: 91
aaaaacccca taactacaaa aaaaa                                           25

<210> SEQ ID NO 92
<211> LENGTH: 25
<212> TYPE: DNA
<213> ORGANISM: Artificial Sequence
<220> FEATURE:
<223> OTHER INFORMATION: Primer

<400> SEQUENCE: 92
ctttaccaaa accaactcta tctcc                                           25

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
aaaccaaaac ccaaaaacta ac                                              22

<210> SEQ ID NO 94
<211> LENGTH: 25
<212> TYPE: DNA
<213> ORGANISM: Artificial Sequence
<220> FEATURE:
<223> OTHER INFORMATION: Primer

<400> SEQUENCE: 94
aattctaaaa cctcctcttc ccct                                            25

<210> SEQ ID NO 95
<211> LENGTH: 25
<212> TYPE: DNA
<213> ORGANISM: Artificial Sequence
<220> FEATURE:
<223> OTHER INFORMATION: Primer

<400> SEQUENCE: 95
```

```
taaattacta ccttaaccaa aatcc                                    25

<210> SEQ ID NO 96
<211> LENGTH: 28
<212> TYPE: DNA
<213> ORGANISM: Artificial Sequence
<220> FEATURE:
<223> OTHER INFORMATION: Primer

<400> SEQUENCE: 96
aggctaacca ctatctcccc tcaaaaaa                                 28

<210> SEQ ID NO 97
<211> LENGTH: 26
<212> TYPE: DNA
<213> ORGANISM: Artificial Sequence
<220> FEATURE:
<223> OTHER INFORMATION: Primer

<400> SEQUENCE: 97
cagtaatacg actcactata gggaga                                   26

<210> SEQ ID NO 98
<211> LENGTH: 26
<212> TYPE: DNA
<213> ORGANISM: Artificial Sequence
<220> FEATURE:
<223> OTHER INFORMATION: Primer

<400> SEQUENCE: 98
cagtaatacg actcactata gggaga                                   26

<210> SEQ ID NO 99
<211> LENGTH: 54
<212> TYPE: DNA
<213> ORGANISM: Artificial Sequence
<220> FEATURE:
<223> OTHER INFORMATION: Primer

<400> SEQUENCE: 99
cagtaatacg actcactata gggagaaggc tgttagtttt tattttatttt ttaa   54

<210> SEQ ID NO 100
<211> LENGTH: 33
<212> TYPE: DNA
<213> ORGANISM: Artificial Sequence
<220> FEATURE:
<223> OTHER INFORMATION: Primer

<400> SEQUENCE: 100
aggaagagag aaccactatc tcccctcaaa aaa                           33

<210> SEQ ID NO 101
<211> LENGTH: 34
<212> TYPE: DNA
<213> ORGANISM: Artificial Sequence
<220> FEATURE:
<223> OTHER INFORMATION: Primer

<400> SEQUENCE: 101
aggaagagag gttagttttt attttatttt taat                          34

<210> SEQ ID NO 102
<211> LENGTH: 54
<212> TYPE: DNA
```

```
<213> ORGANISM: Artificial Sequence
<220> FEATURE:
<223> OTHER INFORMATION: Primer

<400> SEQUENCE: 102
cagtaatacg actcactata gggagaaggc taaccactat ctcccctcaa aaaa        54

<210> SEQ ID NO 103
<211> LENGTH: 416
<212> TYPE: DNA
<213> ORGANISM: Homo sapiens

<400> SEQUENCE: 103
gggtttggga gagtttgtga ggtcgtttat cgtttgttag tagagtgcgt tcgcgagtcg    60
taagtatagt tcggtaatat gcggttttta gataggaaag tggtcgcgaa tgggatcggg   120
gtgtttagcg gttgtgggga ttttgttttg cggaaatcgc ggtgacgagt ataagttcgg   180
ttaattggat gggaatcggt ttgggggggtt ggtatcgcgt ttattagggg gtttgcggta   240
tttttttttg tttttttagta ttttattttt atttttttagg aacgtgaggt ttgagtcgtg   300
atggtggtag gaaggggttt tttgtgttat tcgagttttt agggattcgt agttggtttt   360
tagttatgtg taaagtatgt gtagggcgtt ggtaggtagg gagtagtagg tatggt       416

<210> SEQ ID NO 104
<211> LENGTH: 416
<212> TYPE: DNA
<213> ORGANISM: Homo sapiens

<400> SEQUENCE: 104
gggtttggga gagtttgtga ggttgtttat tgtttgttag tagagtgtgt ttgtgagttg    60
taagtatagt ttggtaatat gtggttttta gataggaaag tggttgtgaa tgggattggg   120
gtgtttagtg gttgtgggga ttttgttttg tggaaattgt ggtgatgagt ataagtttgg   180
ttaattggat gggaattggt ttgggggggtt ggtattgtgt ttattagggg gtttgtggta   240
tttttttttg tttttttagta ttttattttt atttttttagg aatgtgaggt ttgagttgtg   300
atggtggtag gaagggggttt tttgtgttat ttgagttttt agggatttgt agttggtttt   360
tagttatgtg taaagtatgt gtagggtgtt ggtaggtagg gagtagtagg tatggt       416
```